United States Patent
Gong et al.

(10) Patent No.: US 10,660,860 B2
(45) Date of Patent: May 26, 2020

(54) THERAPEUTIC CATIONIC PEPTIDES AND UNIMOLECULAR NANOPARTICLES FOR EFFICIENT DELIVERY THEREOF

(71) Applicant: Wisconsin Alumni Research Foundation, Madison, WI (US)

(72) Inventors: Shaoqin Gong, Middleton, WI (US); Wei Xu, Middleton, WI (US); Yuyuan Wang, Madison, WI (US); Fabao Liu, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 15/892,140

(22) Filed: Feb. 8, 2018

(65) Prior Publication Data

US 2018/0235897 A1 Aug. 23, 2018

Related U.S. Application Data

(60) Provisional application No. 62/456,477, filed on Feb. 8, 2017.

(51) Int. Cl.
| | | |
|---|---|---|
| *A61K 38/10* | (2006.01) | |
| *A61K 38/16* | (2006.01) | |
| *C07K 7/08* | (2006.01) | |
| *A61K 9/51* | (2006.01) | |
| *A61K 38/00* | (2006.01) | |
| *C07K 17/06* | (2006.01) | |
| *A61K 47/59* | (2017.01) | |
| *A61K 47/60* | (2017.01) | |

(52) U.S. Cl.
CPC ............ *A61K 9/5146* (2013.01); *A61K 9/513* (2013.01); *A61K 38/005* (2013.01); *A61K 38/10* (2013.01); *A61K 47/595* (2017.08); *A61K 47/60* (2017.08); *C07K 7/08* (2013.01); *C07K 17/06* (2013.01)

(58) Field of Classification Search
None
See application file for complete search history.

(56) References Cited

U.S. PATENT DOCUMENTS

2013/0332133 A1* 12/2013 Horn .................. C12N 9/00
703/11

OTHER PUBLICATIONS

Bai, et al., "Simultaneous detection and quantification of mitochondrial DNA deletion(s), depletion, and over-replication in patients with mitochondrial disease," The Journal of Molecular Diagnostics, Nov. 2005, pp. 613-622, vol. 7, Issue 5.
Cardenas, et al., "Selective Vulnerability of Cancer Cells by Inhibition of CA (2) Transfer from Endoplasmic Reticulum to Mitochondria," Cell Reports, Mar. 2016, pp. 2313-2324, vol. 14, Issue 10.
Christofk, et al., "The M2 splice isoform of pyruvate kinase is important for cancer metabolism and tumour growth," Nature, Mar. 2008, pp. 230-233, vol. 452.
Clayton, et al., "Isolation of mitochondria from tissue culture cells," Cold Spring Harbor Protocols, 2014, pp. 1109-1112.
Ho, et al., "Phosphoenolpyruvate is a Metabolic Checkpoint of Anti-tumor T Cell Responses," Cell, Sep. 2015, pp. 1217-1228, vol. 162, Issue 6.
Lunt, et al., "Pyruvate kinase isoform expression alters nucleotide synthesis to impact cell proliferation," Molecular Cell, Jan. 2015, pp. 95-107, vol. 57, Issue 1.
Minn, et al., "Genes that mediate breast cancer metastasis to lung," Nature, Jul. 2005, pp. 518-524, vol. 436.
Sanchez, et al., "Genome-wide analysis of the human p53 transcriptional network unveils a lucRNA tumour suppressor signature," Nature Communications, 2014, pp. 1-13, vol. 5.
Wang, et al., "CARM1 methylates chromatin remodeling factor BAF155 to enhance tumore progression and metastasis," Cancer Cell, Jan. 2014, pp. 21-26, vol. 25, Issue 1.

* cited by examiner

*Primary Examiner* — Kevin S Orwig
(74) *Attorney, Agent, or Firm* — Foley & Lardner LLP

(57) ABSTRACT

Provided herein are peptides comprising an amino acid sequence having at least about 85% sequence identity to RYRPRAPIIAVT (SEQ ID NO: 1). These cationic peptides inhibit PKM2 methylation and may be used in the treatment of breast cancer and other diseases or conditions in which PKM2 is overexpressed. Such PKM2 peptides may be delivered to cancer cells using pH sensitive unimolecular nanoparticles comprising anionic polymers.

6 Claims, 68 Drawing Sheets

Specification includes a Sequence Listing.

MCF7

[sequence alignment images]
clone #10 ... +1
clone #18 ... +1 / -5 / -61 / +90

MDA-MB-231
clone #5 ... -2
clone #75 ... +2

MCF7

MDA-MB-231

MCF7

MDA-MB-231

| | | PKM2 ctrl | PKM2 mutant |
|---|---|---|---|
| Mitochondrial proteins | HSPA9(GRP75) | 9 | 7 |
| | SLC25A5 | 9 | 10 |
| | SLC25A6 | 8 | 9 |
| | SLC25A11 | 6 | 4 |
| | SLC25A3 | 4 | 2 |
| | VDAC2 | 3 | 2 |
| | HADHA | 3 | 1 |
| | VDAC1 | 2 | 1 |
| | SLC25A13 | 3 | 0 |
| | ATP5C1 | 2 | 0 |
| | NDUFS8 | 2 | 0 |
| Endoplasmic reticulum (ER) proteins | HSPA5(GRP78) | 13 | 5 |
| | Ins(1,4,5)P$_3$R1 | 8 | 0 |
| | Ins(1,4,5)P$_3$R2 | 10 | 2 |
| | Ins(1,4,5)P$_3$R3 | 14 | 1 |
| | VCP | 8 | 0 |

THERAPEUTIC CATIONIC PEPTIDES AND UNIMOLECULAR NANOPARTICLES FOR EFFICIENT DELIVERY THEREOF

CROSS REFERENCE TO RELATED APPLICATION

This application claims the benefit of and priority to U.S. Provisional Patent Application No. 62/456,477, filed on Feb. 8, 2017, the entire contents of which are incorporated herein by reference in their entireties.

GOVERNMENT RIGHTS

This invention was made with government support under CA196653 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 2, 2018, is named 032026-1365_SL.txt and is 19,319 bytes in size.

FIELD

The present technology relates generally to the field of cationic peptide drugs and peptide drug delivery systems. The compositions of such systems include a unimolecular nanoparticle and cationic peptide drug(s).

SUMMARY OF THE INVENTION

Metabolic reprogramming is a hallmark of cancer. The inventors have discovered that the key glycolytic enzyme, pyruvate kinase M2 (PKM2), but not the related isoform PKM1, is methylated by co-activator associated arginine methyltransferase 1 (CARM1). PKM2 methylation rewires macromolecules biosynthesis from oxidative phosphorylation to aerobic glycolysis in breast cancer cells as well as in hepatomas, rhabdomyosarcoms, lung cancer and Barrett's esophagus. By interacting with and suppressing the expression of inositol 1,4,5-trisphosphate receptors (IP3Rs), methylated PKM2 inhibits the influx of calcium from endoplasmic reticulum (ER) to mitochondria. Inhibition of PKM2 methylation generates metabolic vulnerability to IP3R-dependent mitochondria functions and provides a new target for cancer treatment. The present technology provides the first peptide inhibitors of PKM2 methylation.

In one aspect, the present technology provides cationic peptides that inhibit PKM2 methylation. The peptides include an amino acid sequence having at least about 85% sequence identity to RYRPRAPIIAVT (SEQ ID NO: 1), wherein the amino acid sequence does not vary at residues RPRAP (SEQ ID NO: 6), and wherein the peptide has a length of from 12 to 26 amino acids.

Peptide therapeutics, often exhibit excellent specificity and few side-effects related to off-target interactions. However, peptides, particularly cationic peptides, are often challenging to deliver in therapeutic amounts in vivo. Being charged, cationic peptides may have difficulty crossing cell membranes and may also be degraded in the bloodstream. In addition, depending on their size, peptide therapeutics may also be immunogenic. To mitigate these disadvantages, the inventors have designed a new delivery system for therapeutic cationic peptides.

In one aspect, the present technology provides a unimolecular nanoparticle comprising: a dendritic polymer having a molecular weight of 500 to 120,000 Da and terminating in hydroxyl, amino or carboxylic acid groups; anionic polymers attached to at least a majority of the terminating groups of the dendritic polymer, wherein each anionic polymer comprises a polymeric backbone attached to anionic functional groups and to weakly basic groups by a $C_2$-$C_{12}$ heteroalkyl group comprising 1 to 4 nitrogen atoms, wherein at least one anionic functional group is attached to the polymeric backbone through a pH sensitive linker, the molar ratio of anionic functional groups to weakly basic groups ranges from 1:1 to 10:1, and each anionic polymer has a molecular weight from about 1,000 to about 5,000 Da; and poly(ethylene glycol) attached to a plurality of anionic polymers and having a terminal group selected from a targeting ligand, OH, O-alkyl, $NH_2$, biotin, or a dye, wherein the terminal group of at least one poly(ethylene glycol) is having a molecular weight of about 1,000 to about 15,000 Da. In some embodiments, all of the anionic groups are attached to the polymeric backbone through the pH sensitive linker. In some embodiments, the unimolecular nanoparticle is loaded with a therapeutic cationic peptide as described herein.

In another aspect, the present technology provides methods of treating a disease or condition in which PKM2 is overexpressed (e.g., breast cancer) by administering an effective amount of a unimolecular nanoparticle loaded with an effective amount of a therapeutic cationic peptide, as described herein.

BRIEF DESCRIPTION OF THE DRAWINGS

(FIG. 1A) EdU incorporation assays in parental MCF7 and CARM1 KO cells (n=3). Cells were incubated with 10 µM EdU for 1 hour prior to flow cytometric analysis. (FIGS. 1B-1C) Basal OCR values normalized to cell numbers in parental MCF7 and CARM1 KO cells (FIG. 1B) or in parental MDA-MB-231 and CARM1 KO cells (FIG. 1C) (n=6). (FIGS. 1D-1E) Relative lactate production in parental MCF7 and CARM1 KO cells (FIG. 1D) or in parental MDA-MB-231 and CARM1 KO cells (FIG. 1E) (n=3). (FIG. 1F) Glucose uptake assays in parental MCF7 and CARM1 KO cells (n=3). Mean±SD, **p<0.01, ns: not significant (two-tailed t-test).

(FIG. 2A) Reciprocal co-immunoprecipitation of PKM2 and CARM1 in MCF7 cells followed by Western blot analysis. (FIG. 2B) Direct interaction of recombinant PKM1, PKM2, and PABP1 (positive control) proteins with CARM1 in GST pull-down assays. GST and GST-CARM1 were detected by anti-GST antibody, Flag-tagged PKM1, PKM2 and PABP1 were detected by anti-Flag antibody in Western blot, respectively. (FIGS. 2C-2D) Schematic showing truncations of PKM2 and in vitro interaction assays using full-length PKM and truncated proteins expressed by in vitro transcriptional and translational systems. (FIG. 2E) In vitro methylation assays using recombinant CARM1, GST-PKM1 or PKM2 protein in the presence of $^3$H-SAM. (FIG. 2F) In vitro methylation assays of PKM2 by CARM1 in the presence of FBP (100 µM) or TEPP-46 (1

μM). Histone proteins were used as negative controls. (FIG. 2G) In vitro methylation assays of PKM2 by PRMT family proteins.

(FIG. 3A) PDB structure of PKM2 tetramer (PDB ID: 3SRH) showing the positions of R445, 447 and 455 residues. Neither of the three R methylation sites is localized to the tetrameric interface. (FIG. 3B) Size exclusion chromatography and Western blot analyses of His-tagged PKM2 in the presence and absence of TEPP-46 treatment. Wild type PKM2 and PKM2 R445/447/455K mutant peaks are completely overlapped. (FIG. 3C) Size exclusion chromatography and Western blot analyses of His-tagged PKM1 and the corresponding R445/447/455K mutant. Mutations at R methylation sites do not alter PKM1 tetramer status.

(FIG. 4A) Schematic diagram of full-length PKM2 and its truncated derivatives. (FIG. 4B) Mapping of the methylation domain of PKM2 by CARM1 in in vitro methylation assays. (FIG. 4C) Identification of di-methylated R445, R47 and R455 by mass spectrometry in the in vitro methylated GST-PKM2 protein (SEQ ID NOS 60-62,respectively, in order of appearance). (4D) Schematic showing R→K mutations on GST-PKM2 protein. (FIG. 4E) In vitro methylation assays of PKM2 mutants relative to the wild type PKM2.

(FIG. 5A) Genomic DNA sequencing results of selected PKM2 KO clones shows frame-shifts in PKM2 specific exon, resulting in knockout of PKM2 in MCF7 and MDA-MB-231 cells (SEQ ID NOS 63-69, 63, 70, 63, and 71, respectively, in order of appearance). (FIG. 5B) The relative pyruvate kinase activity in parental and MCF7 PKM2 KO clones (n=3). (FIG. 5C) The relative pyruvate kinase activity in parental MCF7, MCF7 CARM1 KO, parental MDA-MB-231, or MAD-MB-231 CARM1 KO cells (n=3). (FIG. 5D) Cell growth measured by MTT assays in parental MCF7 and MCF7 cells overexpressing PKM1 (n=10). (FIG. 5E) Western blot analysis of PKM1 in MCF7 PKM2 KO or MDA-MB-231 PKM2 KO cells expressing ctrl shRNA or PKM1 shRNA (#1 and 2). (FIG. 5F) Cell growth measured by MTT assays in MCF7 PKM2 KO cells with ctrl shRNA or PKM1 shRNA (#1) knockdown. (FIG. 5G) Basal OCR values normalized to cell numbers in MCF7 PKM2 KO cells with ctrl shRNA or PKM1 shRNA (#1) knockdown. (FIG. 5H) Western blot analysis of methylated PKM2 in immunoprecipitated PKM2 from parental and CARM1 KO cells. (FIG. 5I) Colony formation assays in parental MCF7, PKM2 KO, PKM2$^{wt}$/shPKM1 and PKM2$^{mut}$/shPKM1 cells (n=3). (FIG. 5J) Cell apoptosis measured by Annexin V and propidium iodide (PI) staining in parental MCF7, PKM2 KO, PKM2$^{wt}$/shPKM1 and PKM2$^{mut}$/shPKM1 cells (n=3). Statistical significance was assessed using two-tailed t-test (FIGS. 5C and 5G) and ANOVA (FIGS. 5B, 5D, and 5F). Mean±SD, **p<0.01, ns: not significant.

(FIG. 7A) The ROS levels in parental MCF7, and MCF7 PKM2 KO cells. (FIG. 7O) Images of migrated MDA-MB-231 PKM2$^{mut}$/shPKM1 cells treated with glutathione. Statistical significance was assessed using two-tailed t-test (FIGS. 7A-7C, 7E, and 7G) and ANOVA (FIGS. 7D, 7F, 7H-7L, and 7N). Mean±SD, *p<0.05, **p<0.01.

(FIGS. 8A-8C) Measurement of mitochondrial membrane potential (ΔΨ) by incorporation of JC-1 dye (FIG. 8A) or TMRE dye (FIGS. 8B-8C) and analyses with flow cytometry. The ΔΨ was measured by incorporation of JC-1 (FIG. 8A) or TMRE dyes (FIG. 8B) in parental MCF7, PKM2 KO, PKM2$^{wt}$/shPKM1 and PKM2$^{mut}$/shPKM1 cells (n=3). Alternatively, the ΔΨ was measured by TMRE dye incorporation in parental MCF7, PKM2 KO and CARM1 KO cells (FIG. 8C) (n=3).

8N-8O) Western blot analysis of phosphorylated PDH and total PDH in MCF7 (FIG. 8N) or MDA-MB-231 (FIG. 8O) cells treated with DCA. (FIGS. 8P-8Q) Basal OCR (FIG. 8P) and lactate production (FIG. 8Q) normalized to the cell numbers in MCF7 or MDA-MB-231 cells treated with DCA. Statistical significance was assessed using two-tailed t-test (FIGS. 8H, 8P, and 8Q) and ANOVA (FIGS. 8B, 8C, and 8F-8I). Mean±SD, *p<0.05, p<0.01, *p<0.001.

(FIG. 9A) Mitochondrial membrane potential (ΔΨ) measured by the incorporation of TMRE dye in MDA-MB-231 cells. (FIG. 9B) Mitochondrial DNA (mtDNA) content in parental MCF7, PKM2 KO, PKM2$^{wt}$/shPKM1, and PKM2$^{mut}$/shPKM1 cells. (FIG. 9C) Representative images of parental MCF7, PKM2 KO, PKM2$^{wt}$/shPKM1, and PKM2$^{mut}$/shPKM1 cells treated with 3.5 μM IP3Rs inhibitor XeB for 24 hours. (FIG. 9D) Cell death measured by PI staining in parental MCF7, PKM2 KO, PKM2$^{wt}$/shPKM1, and PKM2$^{mut}$/shPKM1 cells treated with 3.5 μM XeB for 24 hours. (FIG. 9E) Representative images of parental MDA-MB-231, PKM2 KO, PKM2$^{wt}$/shPKM1 and PKM2$^{mut}$/shPKM1 cells after 5 μM XeB treatment for 24 hours. (FIG. 9F) Cell death measured by PI staining in parental MDA-MB-231, PKM2 KO, PKM2$^{wt}$/shPKM1 and PKM2$^{mut}$/shPKM1 cells after treatment with 5 μM XeB for 24 hours. n=3, mean±SD, *p<0.05, p<0.01, *p<0.001 (ANOVA).

(FIG. 10A) Western blot analyses of PKM1 and PKM2 in cytosolic and mitochondria fractions derived from parental MCF7 or PKM2 KO cells. VDAC and tubulin serve as mitochondria and cytoplasm markers, respectively. (FIG. 10N) The gating strategy of flow cytometry.

(FIG. 11A) Western blot analysis of IP3R1, IP3R3, p53 and HSPA9 in parental and PKM2 KO MCF7 or MDA-MB-231 cells. (FIGS. 11M-11N) Normalized basal OCR values in MCF7 (or MDA-MB-231) PKM2$^{wt}$/shPKM1 and PKM2$^{mut}$/shPKM1 cells with ctrl shRNA or IP3R3 shRNA knockdown (n=6). Statistical significance was assessed using two-tailed t-test (FIGS. 11H, 11I, 11K, and 11L) and ANOVA (FIGS. 11M and 11N). Mean±SD, *p<0.05, **p<0.01.

(FIG. 12A) Assessing the proportion of the endogenous methylated PKM2 by immunoprecipitation using the excess amount of methyl-PKM2 antibody. The amount of precipitated methyl-PKM2 is estimated by subtracting the PKM2 left in the flow-through (FT) fraction from the input following detection with PKM2 antibody. The Western blot bands were quantified using ImageJ software (right panel). (FIG. 12B) In vitro methylation assays showing the inhibitory effects of the methyl- or non-methyl PKM2 peptides on the methylation of PKM2 or a control histone H3 protein. (FIG. 12C) Illustration of the UMNP used for PKM2 peptide delivery. (FIG. 12D) Synthesis scheme of the multi-arm star block copolymer poly(amidoamine)-poly(aspartate diethyltriamine-aconitic acid-r-imidazole)-poly(ethylene glycol)-TAT (i.e PAMAM-PAsp(DET-Aco-r-Im)-PEG-TAT) (also referred to herein as polyamidoamine-poly(aspartyl-diethyltriamine-cis-aconitate/imidazole carboxylate)-poly(ethylene glycol)-TAT (i.e., PAMAM-P(Asp-DET-Aco/ICA)-PEG-TAT). (FIG. 12E) $^1$H NMR spectrum of the multi-arm star block copolymer PAMAM-PAsp(DET-Aco-r-Im)-PEG-TAT. The * represents the solvent residual peak. (FIG. 12F) Dynamic light scattering (DLS) histogram of the UMNPs.

(FIG. 12G) In vitro methylation assays showing the inhibitory effects of the methyl- or non-methyl PKM2 peptides encapsulated in the UMNPs on the methylation of PKM2 or a control histone H3 protein. (FIG. 12H) Western blot analysis of endogenous PKM2 methylation and the IP3R3 protein levels upon cellular uptake of UMNP-methyl peptide or UMNP-non-methyl peptide. (FIG. 12I) The relative pyruvate kinase activity of PKM2 in MDA-MB-231 cells treated with UMNP-methyl-peptide or UMNP-non-methyl-peptide (n=3). ns: not significant.

(FIG. 13A) The OCR curves in parental MCF7, PKM2 KO, PKM2$^{wt}$/shPKM1 and PKM2$^{mut}$/shPKM1 cells treated with oligomycin, FCCP, and rotenone/antimycin A (n=6). (FIG. 13B) Basal OCR and lactate production normalized to the cell numbers in parental MCF7, PKM2 KO, PKM2$^{wt}$/shPKM1 and PKM2$^{mut}$/shPKM1 cells. (FIG. 13C) Basal OCR and lactate production normalized to cell numbers in parental MDA-MB-231, PKM2 KO, PKM2$^{wt}$/shPKM1 and PKM2$^{mut}$/shPKM1 cells (n=6). (FIG. 13D) Western blot analysis of methyl-PKM2 in MCF7 cells treated with DMSO or TEPP-46. (FIG. 13E) The OCR curves in parental MCF7 cells treated with DMSO or TEPP-46 (n=6). (FIGS. 13F-13G) Basal OCR and lactate production normalized to cell numbers in MCF7 cells (FIG. 13F) or MDA-MB-231 (FIG. 13G) treated with DMSO or TEPP-46 (n=6). Statistical significance was assessed using two-tailed t-test (FIGS. 13F-13G) and ANOVA (FIGS. 13B-13C). Mean±SD, $*p<0.05$, $p<0.01$, $*p<0.001$.

(FIG. 14A) The chemical structure of the unique UMNP designed for delivery of the positively charged PKM2 peptides. (FIG. 14B) Measurement of peptide uptake efficiency delivered by UMNP in MDA-MB-231 cells using flow cytometry. Peptides were FAM-labelled. (FIGS. 14C-14D) Normalized basal OCR values in MCF7 (FIG. 14C) or MDA-MB-231 (FIG. 14D) cells treated with UMNP-methyl-peptide or UMNP-non-methyl peptide (n=6). (FIG. 14E) MTT assays of MCF7 cells non-treated (control), treated with UMNP-methyl peptide, or treated with UMNP-non-methyl-PKM2 peptide (n=10). (FIG. 14F) Cell migration measured by transwell assays in MDA-MB-231 cells treated with UMNP-methyl-peptide or UMNP-non-methyl-peptide. The relative migratory cell numbers are quantified (n=3). (FIG. 14G) Bioluminescence at the indicated time was measured in lung when mice (n=6) were treated with UMNP-methyl-peptide or UMNP-non-methyl-PKM2 peptide. (FIG. 14H) Representative bioluminescence images of nude mice treated with UMNP-methyl-peptide or UMNP-non-methyl-peptide on day 28. The color scale depicts the photon flux (photons per second) emitted from the lung. (FIG. 14I) The schematic diagram of energy homeostasis regulated by PKM2 methylation in cancer cells. The CARM1 methylates dimeric PKM2 which associates with IP3Rs to inhibit Ca$^{2+}$ influx from ER into mitochondria, thus PDH phosphorylation is increased and oxidative phosphorylation is decreased. Inhibition of PKM2 methylation by knocking out CARM1 or PKM2 or with a competitive PKM2 peptide increases IP3Rs expression, thus $[Ca^{2+}]_{mito}$ is increased, PDH is de-phosphorylated, and oxidative phosphorylation in mitochondria is increased. The cell survival becomes dependent on mitochondria calcium levels and is sensitive to IP3R inhibition. Statistical significance was assessed using two-tailed t-test (FIGS. 14C, 14D, and 14F) and ANOVA (FIGS. 14E and 14G). Mean±SD, $*p<0.05$, $p<0.01$, $*p<0.001$.

DETAILED DESCRIPTION

Figure 1A:
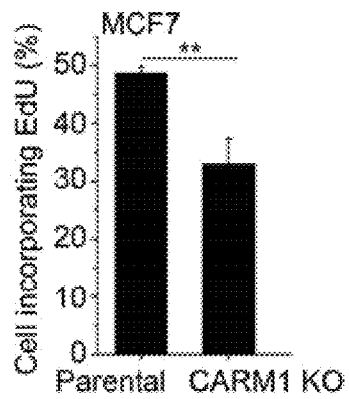
FIGS. 1A-1F shows CARM1 KO decreases EdU incorporation and increases OCR in MCF7 cells.

The following terms are used throughout as defined below. All other terms and phrases used herein have their ordinary meanings as one of skill in the art would understand.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context.

As used herein, the term "amino acid" refers to a C2-C14 chemical moiety having both an amino group (—NH$_2$) and a carboxyl group —COOH). In some embodiments, the amino acids are alpha-amino acids, which may have an L- or D-configuration. Unless indicated otherwise, naturally occurring amino acids (other than glycine) are L-alpha amino acids and are referred to herein by their names or single letter or three-letter abbreviation (e.g., arginine, R, Arg). However, D-amino acids may be substituted into non-critical positions within peptides disclosed herein to improve resistance to degradation by proteolytic enzymes.

As used herein, "about 85% sequence identity" will be understood to mean that about 85% of the subject sequence (e.g., of a peptide) are identical to those of the sequence to which it is being compared. "About 85%" shall be interpreted to mean that 85% of the number of residues shall be rounded up or down to the closest whole number of residues. For example, when applied to a peptide with 12 residues, "about 85%" shall refer to 10 residues (rounded down from 10.2). Likewise, "about 85%" applied to a 14 residue peptide shall refer to 12 residues (rounded up from 11.9). Terms such as "about 90%" and "about 95%" sequence identity shall be interpreted similarly. Hence, "about 90% sequence identity" of a 12 residue peptide shall refer to 11 identical residues, and "about 95% sequence identity" applied to a 26 residue peptide shall refer to 25 identical residues.

"Molecular weight" as used herein with respect to polymers refers to weight average molecular weights (Mw) and can be determined by techniques well known in the art including gel permeation chromatography (GPC). GPC analysis can be performed, for example, on a D6000M column calibrated with poly(methyl methacrylate) (PMMA) using triple detectors including a refractive index (RI) detector, a viscometer detector, and a light scattering detector, and dimethylformamide as the eluent.

The terms "cancer," "neoplasm," "tumor," "malignancy" and "carcinoma," used interchangeably herein, refer to cells or tissues that exhibit an aberrant growth phenotype characterized by a significant loss of control of cell proliferation. The methods and compositions of this disclosure apply to malignant, pre-metastatic, metastatic, and non-metastatic cells.

The term "therapeutic cationic peptide" refers to any therapeutic peptide having at least one amino acid bearing a positive charged side chain at physiological pH (e.g., 7.4) including but not limited to lysine, ornithine, and arginine. A therapeutic peptide is peptide of 2 or more amino acid residues that exerts a therapeutic effect when delivered at an effective amount to treat a subject suffering from or at risk of suffering from a disease, disorder or other medical condition.

The phrase "a targeted receptor" refers to a receptor expressed by a cell that is capable of binding a cell targeting ligand. The cell targeting ligand may be a "tumor cell targeting ligand." The receptor may be expressed on the surface of the cell or inside the cell. In some embodiments, the receptor may be located on the surface of the cell. In some embodiments, the receptor may be located on the surface of the cell and expressed in another part of the cell. The receptor may be a transmembrane receptor. Examples of such targeted receptors include EGFR, $\alpha_v\beta_3$ integrin, somatostatin receptor, folate receptor, prostate-specific membrane antigen, CD105, mannose receptor, estrogen receptor, and GM1 ganglioside.

The phrase "tumor cell targeting ligand" refers to a ligand that binds to "a targeted receptor" unique to or overexpressed by a cancer cell. The ligands may be capable of binding due to preferential expression of a receptor for the ligand, accessible for ligand binding, on the cancer cells. Examples of such ligands include GE11 peptide, anti-EGFR nanobody, cRGD ((cyclo (RGDfC)), KE108 peptide, octreotide, folic acid, prostate-specific membrane antigen (PSMA) aptamer, TRC105, a human/murine chimeric IgG1 monoclonal antibody, mannose, and cholera toxin B (CTB). Additional examples of such ligands include Rituximab, Trastuzumab, Bevacizumab, Alemtuzumab, Panitumumab, RGD, DARPins, RNA aptamers, DNA aptamers, analogs of folic acid and other folate receptor-binding molecules, lectins, other vitamins, peptide ligands identified from library screens, tumor-specific peptides, tumor-specific aptamers, tumor-specific carbohydrates, tumor-specific monoclonal or polyclonal antibodies, Fab or scFv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selecting, steroid hormones, Arg-Gly-Asp containing peptides, retinoids, various galectins, δ-opioid receptor ligands, cholecystokinin A receptor ligands, ligands specific for angiotensin AT1 or AT2 receptors, peroxisome proliferator-activated receptor γ ligands, β-lactam antibiotics, small organic molecules including antimicrobial drugs, and other molecules that bind specifically to a receptor preferentially expressed on the surface of tumor cells or on an infectious organism, or fragments of any of these molecules.

In some embodiments, a cell penetrating peptide may also be attached to one or more PEG terminal groups in place of or in addition to the targeting ligand. A "cell penetrating peptide," also referred to as a "protein transduction domain (PTD)," a "membrane translocating sequence," and a "Trojan peptide", refers to a short peptide (e.g., from 4 to about 40 amino acids) that has the ability to translocate across a cellular membrane to gain access to the interior of a cell and to carry into the cells a variety of covalently and noncovalently conjugated cargoes, including proteins, oligonucleotides, and liposomes. They are typically highly cationic and rich in arginine and lysine amino acids. Examples of such peptides include TAT cell penetrating peptide (GRKKRRQRRRPQ (SEQ ID NO: 7)); MAP (KLAL) KLALKLALKALKAALKLA (SEQ ID NO: 8); Penetratin or Antenapedia PTD RQIKWFQNRRMKWKK (SEQ ID NO: 9); Penetratin-Arg: RQIRIWFQNRRMRWRR (SEQ ID NO: 10); antitrypsin (358-374): CSIPPEVKFNKPFVYLI (SEQ ID NO: 11); Temporin L: FVQWFSKFLGRIL-NH2 (SEQ ID NO: 12); Maurocalcine: GDC(acm)LPHLKLC (SEQ ID NO: 13); pVEC (Cadherin-5): LLIILRRRIRKQA-HAHSK (SEQ ID NO: 14); Calcitonin: LGTYTQDFNK-FHTFPQTAIGVGAP (SEQ ID NO: 15); Neurturin: GAAE-AAARVYDLGLRRLRQRRRLRRERVRA(SEQ ID NO: 16); Penetratin: RQIKIWFQNRRMKWKKGG (SEQ ID NO: 17); TAT-HA2 Fusion Peptide: RRRQRRKKRG-GDIMGEWGNEIFGAIAGFLG (SEQ ID NO: 18); TAT (47-57) YGRKKRRQRRR(SEQ ID NO: 19); SynB1 RGGRLSYSRRRFSTSTGR(SEQ ID NO: 20); SynB3 RRLSYSRRRF (SEQ ID NO: 21); PTD-4 PIRRRKKLRRL (SEQ ID NO: 22); PTD-5 RRQRRTSKLMKR (SEQ ID NO: 23); FHV Coat-(35-49) RRRRNRTRRNRRRVR (SEQ ID NO: 24); BMV Gag-(7-25) KMTRAQRRAAAR-RNRWTAR (SEQ ID NO: 25); HTLV-II Rex-(4-16) TRRQRTRRARRNR (SEQ ID NO: 26); HIV-1 Tat (48-60) or D-Tat GRKKRRQRRRPPQ (SEQ ID NO: 27); R9-Tat GRRRRRRRRRPPQ (SEQ ID NO: 28); Transportan GWTLNSAGYLLGKINLKALAALAKKIL(SEQ ID NO: 29) chimera; MAP KLALKLALKLALALKLA(SEQ ID NO: 30); SBP or Human P1 MGLGLHLLVLAAALQ-GAWSQPKKKRKV (SEQ ID NO: 31); FBP GALFLGWL-GAAGSTMGAW SQPKKKRKV (SEQ ID NO: 32); MPG ac-GALFLGFLGAAGSTMGAWSQPKKKRKV-cya (SEQ ID NO: 33) (wherein cya is cysteamine); MPG(ΔNLS) ac-GALFLGFLGAAGSTMGAWSQPKSKRKV-cya (SEQ ID NO: 34); Pep-1 or Pep-1-Cysteamine ac-KETWWETW-WTEWSQPKKKRKV-cya (SEQ ID NO: 35); Pep-2 ac-KETWFETWFTEWSQPKKKRKV-cya (SEQ ID NO: 36); Periodic sequences, Polyarginines R×N (4<N<17) (SEQ ID NO: 37) chimera; Polylysines K×N (4<N<17) (SEQ ID NO: 38) chimera; (RAca)6R (SEQ ID NO: 39); (RAbu)6R (SEQ ID NO: 40); (RG)6R (SEQ ID NO: 41); (RM)6R (SEQ ID NO: 42); (RT)6R (SEQ ID NO: 43); (RS)6R (SEQ ID NO: 44); R10 (SEQ ID NO: 45); (RA)6R(SEQ ID NO: 46); and R7 (SEQ ID NO: 47).

A "dye" refers to small organic molecules having a molecular weight of 2000 Da or less or a protein which is able to emit light. Non-limiting examples of dyes include fluorophores, chemiluminescent or phosphorescent entities. For example, dyes useful in the present technology include but are not limited to cyanine dyes (e.g., Cy2, Cy3, Cy5, Cy5.5, Cy7, and sulfonated versions thereof), fluorescein isothiocyanate (FITC), ALEXA FLUOR® dyes (e.g., ALEXA FLUOR® 488, 546, or 633), DYLIGHT® dyes (e.g., DYLIGHT® 350, 405, 488, 550, 594, 633, 650, 680, 755, or 800) or fluorescent proteins such as GFP (green fluorescent protein).

The present technology provides pharmaceutical compositions and medicaments comprising any of one of the embodiments of the therapeutic cationic peptide disclosed herein and the unimolecular nanoparticle delivery systems disclosed herein and a pharmaceutically acceptable carrier or one or more excipients. The compositions may be used in the methods and treatments described herein. In one aspect the present technology provides a drug delivery system for the prevention or treatment of cancer. The pharmaceutical composition may include an effective amount of any of one of the embodiments of the compositions disclosed herein. In any of the above embodiments, the effective amount may be determined in relation to a subject. "Effective amount" refers to the amount of compound or composition required to produce a desired effect. One example of an effective amount includes amounts or dosages that yield acceptable toxicity and bioavailability levels for therapeutic (pharmaceutical) use including, but not limited to, the inhibition (i.e., slowing, halting or reversing) or treatment of cancer in a subject. As used herein, a "subject" or "patient" is a mammal, such as a cat, dog, rodent or primate. Typically the subject is a human, and, preferably, a human at risk for or suffering from cancer. The term "subject" and "patient" can be used interchangeably. An effective amount or a therapeutically effective amount of a therapeutic cationic peptide, such as SEQ ID NO:1 (or any of the embodiments thereof described herein) is an amount sufficient to produce the desired effect, e.g., a slowing or halt in the rate of tumor growth, a shrinkage of the tumor and/or death of the cancer cell.

In one aspect, the present technology provides cationic peptide inhibitors of PKM2. In some embodiments, such peptides comprise an amino acid sequence having at least about 85% sequence identity to RYRPRAPIIAVT (SEQ ID NO: 1), wherein the amino acid sequence does not vary at residues RPRAP (SEQ ID NO: 6), and wherein the peptide has a length of from 12 to 26 amino acids. In other words, the peptide may be 12, 13, 14, 15, 16, 17, 18, 19, 20, 21, 22, 23, 24, 25, or 26 amino acid residues long or a range between and including any two of the forgoing values. For example, the peptide may have a length selected from the group consisting of: (i) 12 amino acids; (ii) 14 amino acids; (iii) 15 amino acids; (iv) 19 amino acids; and (v) 26 amino acids. In some embodiments, the peptide may have an amino acid sequence that has at least about 90% sequence identity to SEQ ID NO: 1. In other embodiments, the peptide may have an amino acid sequence that consists of SEQ ID NO: 1, and/or may have a length of 12 amino acids.

In some embodiments, the peptide may have at least about 85%, at least about 90%, or at least about 95% sequence identity to an amino acid sequence selected from the group consisting of

|       |                              | (SEQ ID NO: 2) |
|-------|------------------------------|----------------|
| (i)   | VARYRPRAPIIAVT;              |                |
|       |                              | (SEQ ID NO: 3) |
| (ii)  | RYRPRAPIIAVTRNP;             |                |
|       |                              | (SEQ ID NO: 4) |
| (iii) | RSAHQVARYRPRAPIIAVT;         |                |
| and   |                              |                |
|       |                              | (SEQ ID NO: 5) |
| (iv)  | SGRSAHQVARYRPRAPIIAVTRNPQT.  |                |

In another aspect, the present technology provides a pharmaceutical composition containing any of the peptides disclosed herein and a pharmaceutically acceptable carrier. In some embodiments, the composition comprises a unimolecular nanoparticle comprising a peptide as disclosed herein, and optionally a pharmaceutically acceptable carrier.

In another aspect, the present technology provides unimolecular nanoparticles designed to deliver one or more therapeutic cationic peptides selectively to tumor cells. The cationic peptide is protected within the nanoparticles until it reaches the cytoplasm of the targeted cell. The technology employs a pH sensitive functionality to release the cationic peptide intact from the nanoparticles only once the nanoparticles are within the targeted cells.

The present unimolecular nanoparticles include three distinct polymeric domains: a dendritic polymer, which serves as the core, anionic polymers that include a polymeric backbone attached to the terminal groups of the dendritic polymer, and PEG polymers which are terminally attached to the polymeric backbone of the anionic polymer. Thus, the unimolecular nanoparticle may be described as a multi-arm star-like block copolymer. Therapeutic cationic peptide, including but not limited to SEQ ID NOS: 1-5 (or any of the embodiments thereof described herein) may be loaded into the unimolecular nanoparticles described herein. While not wishing to be bound by theory, it is believed that the therapeutic cationic peptide is bound by electrostatic interactions with the anionic polymers on the interior of the nanoparticle.

The dendritic polymer has a molecular weight of 500 to 120,000 Da and terminates in hydroxyl, amino or carboxylic acid groups. The molecular weight of the dendritic polymer will vary based on the type of polymer and number of generations employed. Suitable molecular weights include about 500, about 1000, about 2000, about 3000, about 4000, about 5000, about 6000, about 7000, about 8000, about 9000, about 10,000, about 15,000, about 20,000, about 30,000, about 40,000, about 50,000, about 75,000, about 100,000, about 120,000 Da, or a range between and including any two of the forgoing values. In some embodiments the molecular weight of the dendritic polymer is about 1,000 to about 10,000 Da. The core of the unimolecular nanoparticle may be a dendrimer such as a poly(amido-amine) (PAMAM) dendrimer having from 3 to 7 generations (e.g., 3, 4, 5, 6, or 7 generations or a range between and including any two of the foregoing values) or a hyperbranched polymer such as a polyester hyperbranched polymer (e.g., Boltorn H30 and H40, which are prepared from 2,2-bis(methylol)propionic acid). PAMAM will be understood to refer to a polymer having a $C_2$-$C_4$ α,ω-diamine initiator and $C_3$-$C_4$ acrylate and diamine building blocks for each subsequent generation. Typically the building blocks are $C_2$ 1,2-diamines and $C_3$ acrylates (not counting the methyl ester carbon, which serves as a temporary protecting group). In some embodiments, the PAMAM dendrimer has from 3 to 4 generations. In some embodiments, the dendritic polymer is a hyperbranched polyester having 3 to 4 generations. The number of generations will determine the number of arms available for attachment to the cationic polymers. Although not every arm of the dendritic polymer must terminate in amino, hydroxyl, carboxylic acid groups, the majority of arms of the dendritic polymer do, e.g., more than 50%, more than 60%, more than 70%, more than 80% or more than 90% of arms of the dendritic polymer terminate in amino, hydroxyl, or carboxylic acid groups. In some embodiments, e.g., where the dendritic polymer is PAMAM or is a hyperbranched polyester, all of the arms terminate in amino groups, hydroxyl groups, or carboxylic acid groups. In some embodiments, the dendritic polymer is a PAMAM dendrimer terminating in amino groups or a hyperbranched polyester terminating in hydroxyl groups.

The anionic polymers of the unimolecular nanoparticle link the core dendritic polymer to the outer PEG blocks. They include anionic functional groups (e.g., carboxylic acid, sulfonic acid, and the like) and pH sensitive linker groups attaching the anionic groups directly or indirectly to the polymeric backbone of the anionic polymer. The anionic polymers of the unimolecular nanoparticles are attached to at least a majority of the terminating groups of the dendritic polymer by, e.g., via amide bonds. Each anionic polymer is made up of a polymeric backbone attached to weakly basic groups by a $C_2$-$C_{12}$ heteroalkyl group comprising 1 to 4 nitrogen atoms, and to anionic functional groups. The anionic functional groups are each conjugated to the polymeric backbone (of the anionic polymer) via pH sensitive linkers, and optionally, the $C_2$-$C_{12}$ heteroalkyl group. The pH-sensitive linker includes a functional group which is readily hydrolyzed upon a change from alkaline pH to acid pH. In some embodiments, the pH sensitive linker may include the anionic functional groups, e.g., cis-aconityl. In some embodiments the pH-sensitive linker will be stable at the pH of blood (about 7.4) and extracellular space in tissue, but hydrolyze at the lower pH of the endosome or lysosome (about 5.5-6.5). Suitable pH-sensitive linkers include imine (formed from, e.g., a benzylamine), hydrazone, cis-aconityl, acetal, and β-thiopropionate linkers. In some embodiments, the pH sensitive linkers include 1-12, 1-8 or 1-6 carbon atoms and 1, 2, 3, 4, 5, or 6 heteroatoms selected from P, N, and S. While not wishing to be bound by theory, hydrolysis of the pH-sensitive linker is intended to release the therapeutic cationic peptide from the unimolecular nanoparticle upon a change in pH from neutral or alkaline to acid.

The polymeric backbone of the anionic polymers may be a polyamide backbone such as a found in peptides and proteins. In some embodiments the polyamide is a polyasparagine, polyglutamine, polyornithine, or polylysine. The anionic functional groups may be functional groups having a pka of not more than 6.5 (e.g., a pka of 6.5, 6, 5.5, 5, 4.5, 4, 3.5, 3, 2.5, 2 or a range between and including any two of the foregoing values). Suitable groups include carboxylic acids, sulfonic acids, and phosphates. It will be understood that the anionic functional groups may be attached to the polyamide backbone or indirectly via a pH sensitive linker. For example, aspartic acid and glutamic acid side chains may be derivatized with amino-functionalized heteroalkyl groups having 1 to 4 nitrogen atoms. When derivatized in this fashion, it will be understood that the polyaspartic acid or polyglutamic acid are now a polyasparagine or a polyglutamine, respectively. Thus in one embodiment, the anionic polymer includes the polyamide backbone (including a side chain), alkylene-amino-alkylene linker, carboxyl groups, and imidazole groups. Similarly, polyornithine and polylysine may be attached to anionic functional groups through suitably functionalized species such as carboxyalkylene-amino-alkylene groups, e.g., (polyamide backbone)-$CH_2CH_2CH_2NH$—$C(O)$—($C_1$-$C_6$ alkylene)-NH—($C_1$-$C_6$ alkylene)-cis aconitate), or (polyamide backbone)-$CH_2CH_2CH_2CH_2NH$—$C(O)$—($C_1$-$C_6$ alkylene)-NH—(C1-C6 alkylene)-cis aconitate).

Weakly basic groups useful in the unimolecular nanoparticles may have a pKa between about 5.5 and about 7.0, e.g., a pKa of 5.5, 5.75, 6, 6.25, 6.5, 6.75, 7, or a range between and including any two of the foregoing values. In some embodiments, the weakly basic group is imidazole or pyridinyl. In certain embodiments, the molar ratio of anionic functional groups to weakly basic groups ranges from 1:1 to 10:1. Suitable molar ratios include about 1:1, about 2:1, about 3:1, about 4:1, and about 5:1, about 7:1, about 10:1, or a range between and including any two of the foregoing values.

In certain embodiments, the anionic polymer has a molecular weight from about 1,000 to about 5,000 Da; in others it is about 1,500 to about 4,000 Da. Suitable molecular weights for the anionic polymers include about 1,000, about 1,500, about 2,000, about 2,500, about 3,000, about 3,500, about 4,000, about 4,500, about 5,000 or a range between and including any two of the foregoing values.

In some embodiments, each anionic polymer comprises a polyamide backbone, heteroalkyl linkers, a pH sensitive linker connecting carboxyl groups to at least one heteroalkyl linker, and imidazole groups. In some embodiments, the anionic polymers comprise moieties selected from the group consisting of ($C_2$-$C_6$ alkylene)amino($C_2$-$C_6$ alkylene)amino-cis-aconityl group, ($C_2$-$C_6$ alkylene)amino($C_2$-$C_6$ alkylene) aminocarbonylimidazole group, and salts thereof. In some embodiments, the anionic polymers comprise moieties selected from the group consisting of ethylene-amino-ethylamino-cis-aconityl group, ethylene-amino-ethylaminocarbonylimidazole group and salts thereof.

PEG is a hydrophilic polymer that forms the outer layer of the unimolecular nanoparticle. The PEG polymeric blocks are attached to a plurality of the cationic polymers. Each arm of the PEG terminates in one of various groups selected from a targeting ligand, OH, O—($C_1$-$C_6$)alkyl, $NH_2$, biotin or a dye. In some embodiments the PEG terminates in OH or O—($C_1$-$C_6$)alkyl, and in still others the PEG terminates in in an $OC_1$-$C_3$ alkyl group. In still other embodiments, the PEG terminates in a targeting ligand. The targeting ligand may be selected from the group consisting of a cofactor, carbohydrate, peptide, antibody, nanobody, or aptamer. In other embodiments, the targeting ligand is selected from the group consisting of folic acid, mannose, GE11, anti-EGFR nanobody, cRGD, KE108, octreotide, TAT cell penetrating peptide, PSMA aptamer, TRC105, and CTB.

Typically each arm of the PEG has 23 to 340 repeat units or a molecular weight of about 1,000 to about 15,000 Da. Suitable molecular weights for each PEG block of the unimolecular nanoparticle include about 1,000, about 1,500, about 2,000, about 2,500, about 3,000, about 4,000, about 5,0000, about 7,500, about 10,000, or about 15,000 Da, or a range between and including any two of the foregoing values.

In another aspect, the unimolecular nanoparticle includes a therapeutic cationic peptide within the nanoparticle, such as a cationic peptide having an amino acid sequence disclosed herein. In some embodiments, the loading of the therapeutic cationic peptide is about 1 to about 20 wt % of the unimolecular nanoparticle. For example, the loading of the therapeutic cationic peptide may be about 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt % or a range between and including any two of the foregoing values.

Any therapeutic cationic peptide may be used in the present unimolecular nanoparticle drug delivery systems. While not wishing to be bound by theory, it is believed that the anionic polymers of the unimolecular nanoparticle bind the therapeutic cationic peptide via electrostatic interactions between the positively charged sidechains of the therapeutic cationic peptide and the anionic functional groups of the anionic polymers. Hence, loading of the therapeutic cationic peptide is independent of the amino acid sequence of the peptide or its length. Therapeutic cationic peptide of a variety of sequence lengths may be loaded into the unimolecular nanoparticle. In some embodiments, the length of the therapeutic cationic peptide is 4, 5, 6, 7, 8, 9, 10, 11, 12, 13, 14, 15, 16, 17, 18, 19, 20, 21, 22, 23, 24, 25, 26, 28, or 30 amino acid residues or a range between and including any two of the foregoing values. In certain embodiments, the length of the therapeutic cationic peptide is from 12 to 26 amino acid residues.

In some embodiments, the therapeutic cationic peptide loaded in the unimolecular nanoparticle is a PKM2 inhibitor, such as any of the cationic peptides described herein. These include but are not limited to those having 12-26 amino acids and comprising amino acid sequences having at least 85%, at least 90%, or at least 95% sequence identity to any of SEQ ID NOS: 1, 2, 3, 4, and 5.

The unimolecular nanoparticles may be prepared using standard techniques. For example, a dendritic polymer in which most or all the surface arms terminate in amino, hydroxyl, or carboxylic acid groups may be conjugated to the cationic polymers via amide, ester, or ether groups. Typically, ester and amide linkages are used for ease of formation. Likewise, the PEG blocks may be attached to the cationic polymers via ester, amide or ether groups. In some embodiments, the PEG has a hydroxy group on one end and an alkoxy or carbonylalkoxy on the other. Standard coupling conditions such as the use of tin catalysis or coupling agents or active esters may be used to form the ester or amide bonds.

The unimolecular nanoparticles described herein may be used to treat, inhibit or prevent a disease or condition in which PKM2 is overexpressed by administering an effective amount of the unimolecular nanoparticle loaded with a PKM2 inhibiting peptide such as any of those described herein. In some embodiments, the disease or condition is selected from the group consisting of breast cancer, hepatoma, rhabdomyosarcoma, lung cancer and Barrett's esophagus. In some embodiments the disease or condition is breast cancer. In certain embodiments, the therapeutic cationic peptide consists of an amino acid sequence of SEQ ID NO: 1.

The compositions described herein can be formulated for various routes of administration, for example, by parenteral, rectal, nasal, vaginal administration, or via implanted reservoir. Parenteral or systemic administration includes, but is not limited to, subcutaneous, intravenous, intraperitoneal, and intramuscular injections. The following dosage forms are given by way of example and should not be construed as limiting the instant present technology.

Injectable dosage forms generally include solutions or aqueous suspensions which may be prepared using a suitable dispersant or wetting agent and a suspending agent so long as such agents do not interfere with formation of the nanoparticles described herein. Injectable forms may be prepared with acceptable solvents or vehicles including, but not limited to sterilized water, Ringer's solution, 5% dextrose, or an isotonic aqueous saline solution.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

Specific dosages may be adjusted depending on conditions of disease, the age, body weight, general health conditions, sex, and diet of the subject, dose intervals, administration routes, excretion rate, and combinations of drug conjugates. Any of the above dosage forms containing effective amounts are well within the bounds of routine experimentation and therefore, well within the scope of the instant present technology. By way of example only, such dosages may be used to administer effective amounts of the cationic peptide drug(s) to the patient and may include about 0.1 mg/kg, about 0.2 mg/kg, about 0.3 mg/kg, about 0.4 mg/kg, about 0.5 mg/kg, about 0.75 mg/kg, about 1 mg/kg, about 1.25 mg/kg, about 1.5 mg/kg, or a range between and including any two of the forgoing values. Such amounts may be administered parenterally as described herein and may take place over a period of time including but not limited to 5 minutes, 10 minutes, 20 minutes, 30 minutes, 45 minutes, 1 hour, 2 hours, 3 hours, 5 hours, 10 hours, 12, hours, 15 hours, 20 hours, 24 hours or a range between and including any of the foregoing values. The frequency of administration may vary, for example, once per day, per 2 days, per 3 days, per week, per 10 days, per 2 weeks, or a range between and including any of the foregoing frequencies. Alternatively, the compositions may be administered once per day on 2, 3, 4, 5, 6 or 7 consecutive days. A complete regimen may thus be completed in only a few days or over the course of 1, 2, 3, 4 or more weeks.

The nanoparticles described herein may be prepared by methods comprising dispersing the cationic within the unimolecular nanoparticle. The drug delivery systems include compositions comprising unimolecular nanoparticles dispersed within a pharmaceutically acceptable carrier or one or more excipients, and an effective amount of anti-cancer cationic peptide dispersed within the unimolecular nanoparticle. As used herein, "dispersed" means distributed, in a generally uniform or in a non-uniform fashion. In some embodiments, the cationic peptide is dispersed in a non-uniform fashion within the nanoparticle. However, it will be understood that nanoparticles with a non-uniform distribution of cationic peptide, especially those with small variations in concentration of the cationic peptide are within the scope of the present technology. The anti-cancer cationic peptide may also be non-uniformly distributed within the unimolecular nanoparticles.

In another aspect, the present technology provides kits including the components needed to prepare any of the compositions described herein. For example, a kit may include a package containing a unimolecular nanoparticle and a package containing an effective amount of therapeutic cationic peptide and directions for use of the kit. In such kits, the unimolecular nanoparticle may include any of those described herein and any of the therapeutic cationic peptides described herein. In some embodiments, the kits may include separate packages for the unimolecular nanoparticles and therapeutic cationic peptides. The present kits allow the user to prepare the drug delivery composition described herein by dispersing the therapeutic cationic peptide in the unimolecular nanoparticles.

The examples herein are provided to illustrate advantages of the present technology and to further assist a person of ordinary skill in the art with preparing or using the nanoparticle compositions of the present technology. To the extent that the compositions include ionizable components, salts such as pharmaceutically acceptable salts of such components may also be used. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

The present technology describes PKM2 peptides and a charge-conversion unimolecular nanoparticle capable of peptide loading and containing imidazole residues developed for endosomal disruption and a charge-conversion segment developed for pH responsive release and peptide delivery. The unimolecular nanoparticle was formed by a multi-arm star polyamidoamine-poly(aspartyl-diethyltriamine-cis-aconitate/imidazole carboxylate)-poly(ethylene glycol), (i.e., PAMAM-P(Asp-DET-Aco/ICA)-PEG) (also referred to herein as poly(amidoamine)-poly(aspartate diethyltriamine-aconitic acid-r-imidazole)-poly(ethylene glycol)

(i.e., PAMAM-PAsp(DET-Aco-r-Im)-PEG)). Because of its covalent nature, the unimolecular nanoparticle has excellent stability in vitro and in vivo. The charge-conversion segment formed by PAsp(DET-Aco) was utilized for peptide delivery and pH-responsive release. In particular, at neutral pH, the anionic PAsp(DET-Aco) segment was used for positively charged PKM2 peptide (e.g., SEQ ID NO:1) complexation through electrostatic interactions. The PEG shell was used to provide good water solubility and reduced opsonization of nanoparticles during blood circulation. Nanoparticles are taken up by cells through endocytosis. The imidazole groups in the charge-conversion segment have a pKa of ~6.0 and can thus absorb protons in the acidic endocytic compartments (endosomes/lysosomes), leading to osmotic swelling and endosome/lysosome-membrane disruption (i.e., the proton sponge effect), thereby facilitating the endosomal/lysosomal escape of the PKM2 peptide. Further, after the nanoparticles are internalized to cells, it is expected that the Aco groups are rapidly cleaved from the PAsp(DET-Aco) segment at the endosomal pH of 5.5, thereby exposing the positively charged PAsp(DET) segment and subsequently leading to the release of PKM2 peptide. The resulting cationic polymer PAsp(DET) is expected to also aid in promoting the endosome escape of the PKM2 peptide through the proton sponge effect. A cell-penetrating peptide is conjugated to the unimolecular micelle to enhance cellular uptake.

The cancer specific pyruvate kinase (PK) isoform PKM2 drives energy production via aerobic glycolysis in cancer cells. PKM2 is a substrate for co-activator associated arginine methyltransferase 1 (CARM1). Inhibition of PKM2 methylation decreases cell proliferation and migration by affecting mitochondrial respiration. The peptides of the present technology act as competitors to inhibit PKM2 methylation. While not wishing to be bound to a particular theory, it is believed that the nanoparticle loaded with PKM2 peptide is capable of perturbing metabolic energy balance in cancer cells and inhibiting breast cancer lung metastasis in a mouse model by inhibiting cellular PKM2 methylation.
Materials and Methods.

The commercial PKM1 (cat#7067S), PKM2 (cat#4053S), VDAC (cat#4661S), PDH (cat#3205T), Tubulin (cat#2148S) antibodies were purchased from Cell Signaling Technology. IP3R1 (cat#A302-158A, Bethyl laboratories, Montgomery, Tex.), IP3R3 (cat# A302-159A, Bethyl laboratories), HSPA9 (cat# MA1-094, Thermo Fisher scientific, Waltham, Mass.), p[Ser293]-PDH (cat# NB110-93479SS, Novus Biologicals, Littleton Colo.) and Flag M2 Affinity Gel (Sigma-Aldrich, St. Louis, Mo.) were purchased from individual vendors. Secondary goat anti-rabbit IgG and anti-mouse IgG were from Jackson ImmunoResearch (West Grove, Pa.). FITC-conjugated goat anti-mouse IgG (cat# A90-116F), Dylight®594 conjugated goat anti-rabbit IgG (cat# A120-101D4) were obtained from Bethyl Laboratories.

S-adenylyl [$^3$H]-AdoMet ($^3$H-SAM) (Perkin Elmer, Waltham, Mass.), Puromycin (RPI, Mount Prospect, Ill.), G418 (Gold BioTechnology, St. Louis, Mo.), Glutathione (Sigma), 2-NBDG (Thermo), Pierce™ Glutathione Agarose Resin (Thermo), Ni-NTA Agarose (Thermo), immobilized Protein A (Replicen, Waltham, Mass.), Click-iT Plus EdU Pacific Blue Flow kit (Thermo), NADP/NADPH-Glo Assay and GSH/GSSG-Glo Assay (Promega, Madison, Wis.), Annexin V Apoptosis Detection Kit APC (cat#88-8007, eBioscience, San Diego, Calif.), PKM2 Activator IV, TEPP-46 (EMD Millipore, Billerica, Mass.), Thapsigargin (Cayman, Ann Arbor, Mich.), JC-1 (Thermo), Rhod-2 am (Thermo), TMRE (tetramethylrhodamine, ethyl ester) (Thermo) and Pluronic F-127 (20% solution in DMSO) (Thermo), Araguspongin B (Synonym: Xestospongin B) (cat. 123000-02-2, Cayman), PKM shRNA-#1, (Sigma, TRCN0000195352), PKM shRNA-#2 (Sigma, TRCN0000296768); IP3R3 shRNA-#1 (Sigma, TRCN0000061327) and IP3R3 shRNA-#2 (Sigma, TRCN0000061324) were obtained from individual vendor.

Cell Culture and Generation of PKM2 Knockout Cells. MCF7, MDA-MB-231, HEK293T cell lines were purchased from ATCC, LM2 was kindly provided by Dr. Joan Massagué, and immortalized MEF (PKM2$^{fl/fl}$, Cre-ER) were kindly provided by Dr. Matthew Heiden and were maintained in DMEM supplemented with 10% fetal bovine serum (FBS) purchased from Gibco (Gaithersburg, Md.). Cells were transiently transfected with a PKM2 specific CRISPR/Cas9/eGFP plasmid using lipofectamine 2000 (Invitrogen, Carlsbad, Calif.) for 24 hours. GFP positive cells were collected by flow cytometry and seeded into 96-well plates with one cell per well. The PKM2 protein level was detected by Western blot. To analyze genomic DNA sequence of each positive clone, the target locus was amplified by PCR using primers PKM2 crispr-F: TCCCCTAGATTGCCCGTGAG (SEQ ID NO: 48) and PKM2 crispr-R: ATTGTTCAATGGACTGCTCCC (SEQ ID NO: 49). Then, the PCR product was inserted into T-vector PMD™20 (Takara Bio USA, Inc., Mountain View, Calif.). For each cell line, plasmids from 30 bacterial colonies were sequenced. For PKM2 KO in MEF cells, MEF cells were treated with 1 µM 4-hydroxytamoxifen (4-OHT) at least for 8-10 days to allow complete knockout of PKM2.

Co-Immunoprecipitation. Co-immunoprecipitation was performed as previously described. See Wang, L., et al., "CARM1 methylates chromatin remodeling factor BAF155 to enhance tumor progression and metastasis," *Cancer Cell* 25, 21-36 (2014). MCF7 cells were lysed with Lysis buffer (50 mM Tris HCl, pH 7.4, with 150 mM NaCl, 1 mM EDTA, and 1% TRITON X-100, protease inhibitor cocktail) and incubated on ice for 30 min. The lysate was centrifuged. Supernatant was pre-cleared by incubated with protein A/G sepharose beads. 500 µL supernatant (2 µg/mL) was incubated with anti-PKM2 or anti-CARM1 antibody for 2 hours at room temperature. Protein A/G sepharose was added into the cell lysate and then incubated for 2 hours. Beads were washed 4 times with lysis buffer and resuspended in 2×SDS loading buffer ((125 mM Tris HCl, pH 6.8, with 4% SDS, 20% (v/v) glycerol, and 0.004% Bromphenol blue). The proteins were analyzed by SDS-PAGE and Western blot.

In vitro methylation assay. In vitro methylation assay was performed as previously described (Wang et al., 2014). Purified histones or purified substrate proteins were mixed with the protein arginine methyltransferases (PRMTs) in the presence of $^3$H-SAM. [$^3$H]-labeled substrates were resolved by SDS-PAGE and detected by autoradiography.

Quantitative Real-time PCR. Total RNA was extracted from the cells using Trizol reagent (Invitrogen, Carlsbad, Calif.). The first-strand cDNA was synthesized by RevertAid First Strand cDNA Synthesis kit (Thermo) according to the manufacturer's instructions. Q-PCR was conducted using SYBR Green dye (Roche Scientific, Basel Switzerland) and a CFX96 instrument (BioRad, Hercules, Calif.). Primer sequences (IDT, Coralville, Iowa) used in this study were as follows: PKM1-RT-F: AGAACTTGTGCGAGCCTCAA (SEQ ID NO: 50); PKM1-RT-R: GACGAGCTGTCTGGGGATTC (SEQ ID NO: 51); PKM2-RT-F: GTGATGTGGCCAATGCAGTC (SEQ ID NO: 52); PKM2-RT-R: CAAGTGGTAGATGGCAGCCT (SEQ ID NO: 53); tRNA Leu-F: CACCCAAGAACAGGGTTTGT (SEQ ID NO: 54); tRNA Leu-R: TGGCCATGGGTATGT-TGTTA (SEQ ID NO: 55); B2-microglobulin-F: TGCT-GTCTCCATGTTTGATGTATCT (SEQ ID NO: 56); B2-microglobulin-R: TCTCTGCTCCCCACCTCTAAGT (SEQ ID NO: 57).

Gel Filtration. Recombinant his-tagged PKM2 protein was incubated with TEPP-46 (10 μM) for 1 hour on ice, then separated in the Superdex 200 Increase 10/300 GL column (GE Healthcare) in 0.01 M phosphate buffer and 0.14 M NaCl at pH 7.4. The speed rate of flow is 0.5 ml/min. Fractions were collected every 0.3 ml per tube and analyzed by UV absorbance or SDS-PAGE and Western blot.

Pyruvate Kinase and Lactate Dehydrogenase Assays. Pyruvate kinase activity was measured according to previous report. See Christofk, H. R., et al., "The M2 splice isoform of pyruvate kinase is important for cancer metabolism and tumour growth," *Nature* 452, 230-233 (2008). Briefly, 2 μg whole cell lysate was incubated in 1 ml buffer (Tris pH 7.5 (50 mM), KCl (100 mM), MgCl2 (5 mM), ADP (0.6 mM), PEP (0.5 mM), NADH (180 μM), and LDH (8 units). The change in absorbance at 340 nm owing to the oxidation of NADH was measured using a Nano drop ND-2000 1-position spectrophotometer (Thermo). LDH activity was determined by measuring the decreased fluorescence intensity at 340 nm from the NADH oxidation in buffer (Tris pH 7.5 (50 mM), KCl (100 mM), MgCl$_2$ (5 mM), pyruvate (20 mM), NADH (180 μM).

Cell Cycle Analysis. $1 \times 10^6$ cells were centrifuged and washed twice with PBS. The cell pellet was resuspended in 200 μl of ice-cold PBS, and then 800 μL of ice cold ethanol was added. Cells were fixed at 4° C. overnight. Fixed cells were centrifuged and washed twice in PBS. Cells were treated with RNase and resuspended in the wash buffer with propidium iodide (PI, 50 μg/ml). Cells were analyzed for PI content on a BD FACSCalibur flow cytometer.

Subcellular Fractionation. The isolation of cytosol and mitochondria was based on a known protocol. See Clayton, D. A., and Shadel, G. S., "Isolation of mitochondria from tissue culture cells," *Cold Spring Harb Protoc* 2014, pdb prot080002 (2014). Briefly, the cell pellets were resuspend in 11 mL ice-cold RSB hypo buffer (10 mM NaCl 1.5 mM MgCl$_2$ 10 mM Tris-HCl (pH 7.5)) and allow the cells to swell for 5-10 min, then the swollen cells were broken open with several strokes in the presence of 8 mL of 2.5×MS homogenization buffer (525 mM mannitol 175 mM sucrose 12.5 mM Tris-HCl (pH 7.5) 2.5 mM EDTA (pH 7.5)) to give a final concentration of 1×MS homogenization buffer. The homogenate was centrifuged at 1300 g for 5 min and repeated for several times. The supernatant was transferred to a clean tube and the mitochondria was pelleted at 7,000 g for 15 min. The supernatant is the cytosolic fraction and the pellet is the rude mitochondria fraction. The pellet was re-suspended with 1×MS homogenization buffer followed by the 7,000 g sedimentation several times.

Confocal Imaging Analysis. MAD-MB-231 cells were fixed with 4% paraformaldehyde in culture media for 15 min at 37° C. and permeabilized with 0.2% Triton X-100 for 10 min at room temperature. The nonspecific binding was blocked by incubation with 4% BSA in PBS for 60 min, and cells were subsequently stained with primary PKM2 and HSPA9 antibodies overnight at 4° C. The slides were washed in PBS three times (5 min/each time) and were incubated for 1 hour with the following secondary antibodies: FITC-conjugated goat anti-mouse IgG and Dylight®594 conjugated goat anti-rabbit IgG. After being washed three time in PBS and air-dried, the coverslips were mounted in ProLong Gold anti-fade reagent with DAPI (Invitrogen). Fluorescence was examined using a Leica SP8 3×STED Super-resolution microscope (Buffalo Grove, Ill.) equipped with a 63× objective lens with laser excitation at 405 nm, 488 nm or 592 nm. For z-stack analysis, optical sections were obtained along the z-axis at 0.5-μm intervals. Images were analyzed with the ImageJ software.

Expression and purification of recombinant proteins. Human PRMT1-8 cDNAs were cloned into pFN21K HaloTag CMV Flexi Vector (Promega) (Wang et al., 2014). These plasmids were transiently transfected into HEK293T cells for 36 hours. The cells were harvested in binding buffer (HEPES 50 mM, NaCl 150 mM, NP40 0.005%, 0.5 mM EDTA, pH 7.5) and sonicated at 35% power (amplitude) with 10 s on, 30 s off, 4-6 cycles on ice, and then centrifuged and collected the supernatant. The supernatant was incubated with HaloLink resin (Promega) overnight at 4° C. The beads were washed with binding buffer twice and then incubated with 1M urea in binding buffer for 20 min at room temperature. After washing the beads with binding buffer twice, the proteins were eluted with 20 μg/mL TEV in cleavage buffer (DTT 1 mM in binding buffer). For purification of Flag-tagged proteins, the plasmids were transiently transfected into HEK293T cells for 36 hours. The cells were harvested in lysis buffer on ice for 30 min, and then centrifuged and collected the supernatant. Flag M2 Affinity Gel was added into the supernatant and incubated for 2 hours, and then the Gel was washed with PBS four times. The proteins were eluted by 150 μg/mL 3× Flag peptide in 0.5 M Tris HCl and 1M NaCl pH 7.5. For His-tagged or GST-tagged proteins purification, PKM1 and PKM2 cDNA were inserted pET-21a (+) or pGEX-2T plasmid. The plasmids were then transfected into *E. coli* BL-21 competent cells. Protein expression was induced by the presence of 0.5 mM IPTG overnight at 20° C. After centrifugation, pellet was resuspended in sonication buffer (1% Triton X-100, 1 mM EDTA, 1 mM DTT in PBS) and sonicated at 50% power (amplitude) with 30 s on, 30 s off, 10 cycles on ice or until the suspension became clear. After centrifugation, the supernatant was incubated with Ni-NTA Agarose or Glutathione Agarose Resin for 2 hours at room temperature. For His-tagged proteins, Beads were washed with PBS twice, then washed with 10 mM imidazole in elution buffer (1% Triton X-100, 0.1% glycerol in PBS) once. The His-tagged proteins were eluted with 250 mM imidazole. For GST-tagged proteins, beads were washed with PBS four times and eluted with glutathione elution buffer (50 mM Glutathione, 50 mM Tris HCl, pH 8.0, 100 mM NaCl, and 1 mM EDTA). The eluted proteins were dialyzed with PBS containing 0.1% glycerol.

GST Pull-down Assays. GST and GST-CARM1 proteins were expressed in *E. coli* BL-21 competent cells and purified by glutathione sepharose 4B resin (GE Healthcare Life Sciences). The GST or GST fusion protein bound beads were incubated with recombinant, Flag-tagged PKM2 proteins purified from HEK 293T cells for 4 hours at 4° C. The beads were washed 4 times with binding buffer (1×PBS, 0.1% NP40, 0.5 mM DTT, 10% Glycerol, 1 mM PMSF) and boiled with 2×SDS loading buffer. Samples were analyzed by SDS-PAGE and western blotting with anti-Flag antibody.

In Vitro Protein-Protein Interaction Assay. Flag-tagged full length PKM2 and its truncations constructs were translated by T7 Quick Coupled Translation/Transcription system (Promega). Then the Flag-tagged proteins were incubated with GST-CARM1 fusion protein (1 μg/mL) in binding buffer (1×PBS, 0.1% NP40, 0.5 mM DTT, 10% Glycerol, 1 mM PMSF) for 4 hours at 4° C. The beads were washed 4 times with binding buffer, and recombinant proteins were eluted with 500 µg/ml 3× Flag peptides. Samples were analyzed by SDS-PAGE and Western blotting.

Cell Proliferation and Cell Cycle Analyses. For quantitative proliferation assays, 1000 cells per well were seeded onto 96-well plates. 3-(4,5-dimethylthiazol-2-yl)-2,5-diphenyltetrazolium bromide (MTT) solution (20 µL per well, 4 mg/mL) was added into the wells and incubated 4 hours. After discarding the supernatant, 200 µL DMSO was added and the absorbance value (optical density) was measured at 490 nm on a Victor X5 microplate reader (Perkin Elmer, Waltham, Mass.). In the next 3 days, the absorbance value was measured every day. For 5-Ethynyl-2'-deoxyuridine (EdU) incorporation assay, $3\times10^5$ cells were seeded into 6-well plate and incubated 10 µM EdU for 1 hour, followed by the procedures described in the Click-iT® EdU cytometry assay kit according to the manufacturer's instructions. Cells were then analyzed on BD LSRII. For clonogenicity assay, 1000 viable transfected cells were placed in six-well plates and maintained in complete medium for 2 weeks. Colonies were washed with PBS and fixed with 3.7% formaldehyde for 15 min at room temperature, and then stained for 20 min with 0.05% crystal violet.

Transwell Cell Migration Assays. Cell migration assay was performed as previously described (Wang et al., 2014) using 8.0 µm pore size Transwell inserts (Costar Corp., Cambridge, Mass.). Briefly, $1\times10^5$ cells in 1004, serum free media were added into the upper chamber, 500 µL culture media with 20% FBS was in the lower well. After 12 hours culture, removed the cells on the upper surface of the membrane and fixed the migrant cells attached to the lower surface with 3.7% formaldehyde in culture media at 37° C. for 15 min, and then stained for 20 min with 0.05% crystal violet.

Generation of methylated PKM2 (methyl-PKM2) specific antibody. Methyl-PKM2 specific anti-peptide antibody was prepared by Genemed Synthesis Inc., TX, using standard methods of peptide synthesis. The KLH-conjugated PKM2 peptide RYR(as)PR(as)APIIAVTC, (SEQ ID NO: 58)with R445 and R447 asymmetrically dimethylated was synthesized. The peptide corresponding to human PKM2 amino acids 443-454, was used to immunize rabbits. To purify the di-me-PKM2 specific antibody, 10 mg dimethyl peptide (column A) and 10 mg control peptide (non-methyl) (column B) were coupled separately to cyanogen bromide activated agarose beads. 100 ml of antisera was then incubated with the peptide-agarose column A. The unbound antiserum was washed with 1×PBS buffer. After several washes, the antibody was eluted with 0.1 M glycine, pH 2.5; neutralized with 1M 23 Tris, pH 8.0. The antibody was stabilized with 0.1% BSA [Elution A]. Elution A was then incubated with column B and then same procedure was followed for elution. The flow through from column B was the dimethyl-specific antibody (methyl-PKM2). The antisera and purified antibody were then tested by enzyme-linked immunosorbent assay (ELISA).

Measurement of Oxygen Consumption Rate. The OCR was measured in an XF96 extracellular analyzer (Seahorse Bioscience). $2\times10^4$ cells per well were seeded into the 96-well plate and incubated in DMEM media with 10% FBS at 37° C. overnight. Next day, the media was changed to analysis media containing 10 mM glucose. The cells were incubated in a $CO_2$-free incubator at 37° C. for 1 hour. Cells were sequentially exposed to oligomycin (1 µM), FCCP (0.5 µM) and rotenone (0.5 µM). Each point in traces represent the average of measurement from six different wells.

Measurement of Glucose Uptake. For each experiment, cells were washed and subsequently studied in a modified balanced salt solution (MBSS) containing (in mM): 140 NaCl, 5.4 KCl, 0.5 $MgCl_2$, 0.4 $MgSO_4$, 3.3 $NaHCO_3$, 2.0 $CaCl_2$, 10 HEPES, 5.5 glucose, pH 7.4, 2-NBDG (0.1-0.3 mM) was added to the bathing media, after 20 min incubation and several washes, uptake of 2-NBDG was measured by fluorescence spectrometry.

Mass Spectrometry Analysis of the Arginine Methylation.

In gel digestions. The gel was destained two times for 5 min with 200 µl of 100 mM $(NH_4)HCO_3$/50% Methanol, and then dehydrated for 2 min with 200 µl of 25 mM $(NH_4)HCO_3$/50% Acetonitrile then once more for 30 seconds in 100% Acetonitrile. After drying for 2 min in a vacuum centrifuge, the gel particles was rehydrated with 50 µl of freshly prepared 25 mM dithiothreitol for 20 min at 56° C. After that, 50 µl of freshly prepared 55 mM iodoacetamide was added to alkylate the proteins for 20 min at room temperature in the dark. After extensive wash with 200 µl of 25 mM $(NH_4)HCO_3$/50% Acetonitrile, the gel pieces was rehydrated for 5 min at room temperature in 20 µl of digestion solution containing 50 ng of trypsin (Promega Sequence Grade) in 25 mM $(NH_4)HCO_3$/0.01% ProteasMAX™ (Trypsin enhancing and extraction promoting surfactant from Promega Corporation, Madison, Wis.) and incubated for 3 hours at 42° C. The tryptic peptides were extracted by adding 25 µl of 2.5% trifluoroacetic acid (TFA) solution.

LC-MS data acquisition. Peptides were resuspended in 0.1% formic acid (FA) and analyzed on a Waters nanoAcquity ultra performance liquid chromatography system coupled to a Q-Exactive quadrupole orbitrap mass spectrometer (Thermo Fisher Scientific). Peptide sample was injected (2 µl) and loaded onto the Waters Symmetry C18 trap column (180 µm×20 mm, 5 µm) using 97% mobile phase A (0.1% of FA in water) and 3% mobile phase B (0.1% of FA in ACN) at a flow rate of 5 µL/min for 3 min. A Waters BEH 300 Å C18 reversed phase capillary column (150 mm×75 µm, 1.7 µm) was used for separation. The gradient started from 3% to 10% B during the first 5 min, increased to 55% B in the next 45 min, and then was kept at 90% B for 20 min. The data was acquired under data dependent mode (DDA, top 20). Mass spectrometric conditions were as follows: spray voltage of 2.8 kV, no sheath and auxiliary gas flow; heated capillary temperature of 275° C., normalized high-energy collision dissociation (HCD) collision energy of 30%, resolution of 70,000 for full scan, resolution of 17, 500 for MS/MS scan, automatic gain control of $2e^5$, maximum ion injection time of 100 ms, isolation window of 2 m/z, and fixed first mass of 100 m/z.

LC-MS data analysis. Mass spectral data were searched in PEAKS Studio (Bioinformatics Solutions Inc., Waterloo, ON) against a home-made FASTA database containing the PKM2 protein sequence. Trypsin was selected as the enzyme and two missed cleavage sites were allowed. PEAKS searches were performed with a precursor mass tolerance of 20 ppm and a fragment mass tolerance of 0.05 Da. The fixed modifications consisted of carbamidomethylation (57.0215 Da) of cysteine residues. The variable modifications consisted of dimethylation (28.0313 Da) of arginine residues and oxidation (15.9949 Da) of methionine. Peptide spectral matches were validated based on p-value of 1% false discovery rate.

Proteomics analysis. Cells were resuspended in cold 8 M urea, 50 mM Tris-HCl, and 30 mM NaCl containing protease inhibitor tablet (lysis buffer), and homogenized for three cycles of 30 s each. All lysates were processed by centrifugation at 16,000 g at 4° C. for 10 min. The concentrations of protein were determined by bicinchoninic acid (BCA) assay (Thermo). Protein extract was reduced by 5 mM Dithiothreitol (DTT) for 1 hour at room temperature and alkylated with 15 mM iodoacetamide (IAA) in the dark for 30 min at room temperature. Excess IAA was quenched with 5 mM DTT. Proteins were diluted with 50 mM Tris-HCl to a urea concentration of 0.9 M and subjected to digestion with trypsin at 50:1 protein: enzyme ratio. The reaction was incubated at 37° C. for 16 hours and quenched with 10% TFA. The tryptic peptides were desalted with Sep-Pak C18 cartridge (SPE, Waters).

One milligram of each DiLeu label was dissolved in 25 μl of anhydrous DMF, and combined with DMTMM and NMM at 0.7× molar ratio to DiLeu labels. The activation reaction occurred at room temperature by vortexing the mixture for one hour. The supernatant was used immediately to label the peptides. 5× w/w activated DiLeu reagents were used to label the protein extract. Additional anhydrous DMF was added to ensure organic composition reaches 70% (v/v). The labeling reaction was performed at room temperature by vortexing for two hours and quenched by addition of hydroxylamine to a concentration of 0.25%. The labeled samples were pooled at a 1:1 ratio across all the samples and dried in vacuo.

Strong cation exchange (SCX) fractionation was performed on a Waters Alliance e2695 HPLC (Milford, Mass.) with a flow rate of 0.2 ml/min. Tryptic peptides were dissolved in 10 mM $NH_4HCO_3$, 25% ACN (v/v), pH 3, and loaded onto a 200 mm×2.1 mm polySULFOETHYL A (PolyLC, Columbia, Md.) column with 5 μm packing materials. Buffer A was composed of 10 mM $NH_4HCO_3$, 25% ACN (v/v), pH 3, and buffer B was composed of 500 mM $NH_4HCO_3$, 25% ACN (v/v), pH 6.8. Gradient elution program starts with 100% A for 20 min, followed by a gradient of 0-50% B for 70 min. B increased from 50-100% over 10 min and stayed at 100% B for 10 min. The fractions were collected every 1.5 min and concatenated into 10 fractions determined by UV-VIS at 215 nm.

All samples were reconstituted in 0.1% FA, 3% ACN and loaded on the fabricated column. The column was filled with 1.7 μm Ethylene Bridged Hybrid packing materials (130 Å, Waters). Peptides were separated with Dionex UltiMate 3000 LC system before entering the Orbitrap Fusion Lumos tribrid mass spectrometer (San Jose, Calif.). MS scans were acquired in a profile mode in the range of 300-1500 m/z at resolution of 60K, followed by selection of fifteen most intense ions for HCD fragmentation with an isolation width of 1 m/z. $2×10^5$ and $5×10^5$ were selected as the automatic gain control (AGC) target for MS and MS/MS scans, respectively. The maximum injection time was set to 100 ms for both MS and MS/MS scans. Tandem mass spectra were acquired with a normalized collision energy (NCE) of 30 and a fixed first mass of 110 m/z.

The OMSSA proteomic Analysis Software Suite (COMPASS) was used for peptide identification. Raw files were converted to text files and searched against the *Homo sapiens* Uniprot reference proteome database. Trypsin was selected as the enzyme and maximum of two missed cleavages were allowed. Precursor ion tolerance was set to 25 ppm and fragment ion tolerance was 0.02 Da. DiLeu labeling on peptide N-termini and lysine residue (+145.1267748 Da), and carbamidomethylation of cysteine residues (+57.02146 Da) were chosen as static modifications. Methionine oxidation (+15.99492 Da) and DiLeu labeling on tyrosine residue (+145.1267748) were selected as variable modifications. Search results were filtered to 1% false discovery rate (FDR) at both peptide and protein levels. Quantification was performed using an in-house software called DiLeu tool. Reporter ion abundances are corrected for isotope impurities with python script.

Measurement of Mitochondrial Membrane Potential (ΔΨ) and DNA Content. Cells were loaded with JC-1 (10 μg/mL) for 10 min or Tetramethylrhodamine, Ethyl Ester (TMRE) for 20 min in phenol red free media at 37° C. followed by three time washes with PBS. Cells were harvested with trypsin for flow cytometry analysis. The relative quantification of mitochondrial DNA levels were determined by the ratio of mitochondrial tRNA Leu to the nuclear-encoded B2-microglobulin. See Bai, R. K., and Wong, L. J., "Simultaneous detection and quantification of mitochondrial DNA deletion(s), depletion, and over-replication in patients with mitochondrial disease," *J Mol Diagn* 7, 613-622 (2005).

Measurement of Calcium Flux. Simultaneous measurement of $[Ca^{2+}]_{mito}$ was based on the previously described method. See Ho, P. C., et al., "Phosphoenolpyruvate Is a Metabolic Checkpoint of Anti-tumor T Cell Responses," *Cell* 162, 1217-1228 (2015). The main modifications are as described below. MCF7 cells were loaded with Rhod-2 AM (2 μM) and 20% (v/v) Pluronic F-127 (0.02%) and incubated in calcium free PBS with 5% FBS buffer for 45 min. MDA-MB-231 and MEF cells were loaded with Rhod-2 AM (0.45 μM) and 20% (v/v) Pluronic F-127 (0.02%) and incubated in calcium free PBS with 5% FBS buffer for 15 min. Before fluorescent measurements are commenced, cells were washed with PBS to remove any dye that is nonspecifically associated with the cell surface, and then incubated for another 30 min to de-esterification of intracellular AM esters. Cells were harvested with trypsin for flow cytometry analysis.

Cell apoptosis and death analyses. Cell apoptosis and death assays were based on the previously described method. See Cardenas, C., et al., "Selective Vulnerability of Cancer Cells by Inhibition of Ca(2+) Transfer from Endoplasmic Reticulum to Mitochondria," *Cell Rep* 14, 2313-2324 (2016). Briefly, cell apoptosis was determined by annexin V/APC and propidium iodide (PI) staining. Cell death was determined by PI staining using flow cytometry.

TCGA RNA-seq and CPTAC proteomics data analyses. TCGA RNA-seq data was downloaded from Fire Browse the Internet site at: gdac.broadinstitute.org/runs/stddata_2016_01_28/data/BRCA/20160128/ gdac.broadinstitute.org_BRCA.Merge_rnaseqv2_illumina hiseq_rnaseqv2_unc_edu_Level_3_RSEM_genes_norma lized_data.Level_3.2016012800.0.0.tar.gz). Normalized fragment counts from all 1,093 primary tumor samples were used to study the co-expression patterns. CPTAC proteomics data were downloaded from the Internet site at: prot-shiny-vm.broadinstitute.org:3838/BC2016/. Normalized protein abundances from all 77 tumor samples were used. Pearson correlation coefficients and associated p-values were calculated between each pair of genes for both TCGA RNA-seq data and CPTAC proteomics data.

Unimolecular nanoparticle (UMNP) synthesis. Materials: Tris(2-carboxyethyl)phosphine hydrochloride (TECP) was purchased from Thermo Scientific (Waltham, Mass., USA). Aconitic anhydride, N-hydroxysuccinimide (NHS), 4-imidazolecarboxylic acid (Im), β-benzyl L-aspartate (BLA), and PAMAM-COOH (G4 with 64 carboxyl terminal groups) were purchased from Sigma-Aldrich (Milwaukee, Wis., USA). Cell penetrating peptide TAT (Sequence CYGRK-KRRQRRR (SEQ ID NO: 59)) was purchased from Genscript (Piscataway, N.J., USA). Heterobifunctional PEG derivatives, $NH_2$-PEG-$OCH_3$ (mPEG-$NH_2$, Mw=5000 Da) and $NH_2$-PEG-Maleimide ($NH_2$-PEG-Mal, Mw=5000 Da), were purchased from JenKem Technology (Allen, Tex., USA). 1,3-dicyclohexylcarbodiimide (DCC) was purchased from ACROS (Morris, N.J., USA). Diethyltriamine (DET) was purchased from TCI America, (Portland, Oreg., USA).

Characterization: The $^1$H NMR spectra were collected on a Bruker Advance 400 NMR spectrometer at 400 MHz using CDCl$_3$, DMSO-D6 or D$_2$O as the solvent and 0.5% tetramethyl-silane as the internal standard. The molecular weights of the multi-arm star copolymers were determined by a gel permeation chromatography (GPC) system equipped with triple detectors, including a refractive index detector, a viscometer detector, and a light scattering detector (Viscotek, USA). DMF was used as a mobile phase with a flow rate of 1 mL/min. The hydrodynamic size distribution and zeta-potential of the UMNPs were characterized by a dynamic light scattering (DLS) spectrometer (Malvern Zetasizer Nano ZS). The concentration of the polymer solution used for the DLS measurement was 0.1 mg/ml. To determine the peptide loading level of UMNPs, 0.6 mg FAM-peptide loaded UMNPs were dispersed in 3 ml DI water. The pH of the resulting solution was adjusted to 4 and the solution was stirred at room temperature for 12 h to allow complete release of peptide from the UMNPs. The peptide loading level was determined by a UV-Vis spectrometer (Cary 5000 UV-Vis-NIR, Agilent Technologies) with the absorbance of FAM at 495 nm.

Animal Experiments. All animal work was performed in accordance with protocols approved by Research Animal Resource Center of University of Wisconsin-Madison. Balb/c nude female mice at 4-6 week old were used for all xenograft experiments (Harlan, Madison, Wis.). For lung metastasis assays, human breast cancer cells LM2 derived from MDA-MB-231 cells were cultured in 10 cm dishes and treated with UMNP-methyl-peptide or UMNP-non-methyl-peptide for 24 hours. Then cells were trypsinized and washed twice in PBS. Subsequently, 1×10$^6$ cells resuspended in 0.1 ml PBS were retro-orbitally injected into mice. Mice were imaged for luciferase activity immediately after injection (day 0) to exclude any mouse that were not successfully xenografted. Luciferase-based noninvasive bioluminescent imaging and analysis were performed as described previously using an IVIS Imaging System (Caliper Life Sciences, Hopkinton, Mass.). See Minn, A. J., et al., "Genes that mediate breast cancer metastasis to lung," Nature 436, 518-524 (2005). Briefly, mice were anaesthetized and injected intraperitoneally with 2 mg D-luciferin (20 mg/ml in PBS) (Gold Biotechnology). Imaging was completed between 5 to 10 min after injection. For bioluminescence plots, total photon flux was calculated for each mouse in the gated areas. Then, the mice were retro-orbitally injected with UMNP-methyl-peptide or UMNP-non-methyl-peptide (100 μl, 1 g/L) twice per week for 4 weeks. Imaging was taken every week and endpoint assays were conducted at 4 weeks after injection.

Statistical Analysis. Results were presented as mean±SD and statistical significance was examined by an unpaired Student's t test. p value <0.05 (*) was considered as statistically significant.

Example 1: Preparation of Unimolecular Nanoparticle Loaded with PKM2 Peptide (SEQ ID NO: 1)

Synthesis of β-benzyl L-aspartate N-carboxyanhydride (BLA-NCA): Triphosgene (4.5 g, 15 mmol) in 10 ml anhydrous tetrahydrofuran (THF) was added dropwise to a BLA (6.5 g, 30 mmol)/anhydrous THF (40 ml) solution at room temperature. Then, the mixture was stirred at 55° C. under nitrogen for 3 h until a clear solution was observed. Thereafter, the THF solvent was removed under vacuum and the product, BLA-NCA, was purified by recrystallization using a mixture of THF and hexane (1:1, v/v). The chemical structure was confirmed by $^1$H NMR (400 MHz, CDCl$_3$). BLA-NCA: 7.42-7.28 (5H, m, Ar—H), 6.30 (1H, s, NH), 5.20 (2H, s, CH$_2$—Ar), 4.6 (1H, t, CH), and 2.9 (2H, t, COCHCH$_2$) ppm.

Synthesis of poly (β-benzyl L-aspartate)-poly(ethylene glycol) (PBLA-PEG): The PEG-PBLA block copolymers were prepared by ring-opening polymerization. Typically, 100 mg (0.02 mmol) PEG-NH$_2$ (mPEG-NH$_2$, or Mal-PEG-NH$_2$) and 230 mg (0.88 mmol) BLA-NCA were dissolved in 5 mL anhydrous N,N-dimethylformamide (DMF). The solution was stirred at 55° C. for 72 h. Thereafter, the product was isolated by precipitation in cold diethyl ether and dried under vacuum. The chemical structures of resulting polymers were confirmed by $^1$H NMR (400 MHz, DMSO-D$_6$). mPEG-PBLA: 7.26-7.38 (102H, m, Ar—H), 5.00-5.10 (40H, s, CH$_2$—Ar), 4.55-4.68 (20H, m, COCHCH$_2$), 3.35-3.53 (450H, m, CH$_2$CH$_2$O from PEG), and 2.48-2.90 (41H, m, COCHCH$_2$) ppm. Mal-PEG-PBLA: 7.26-7.38 (102H, m, Ar—H), 6.95 (2H, s, Mal), 5.00-5.10 (40H, s, CH$_2$—Ar), 4.55-4.68 (20H, m, COCHCH$_2$), 3.35-3.53 (450H, m, CH$_2$CH$_2$O from PEG), and 2.48-2.90 (41H, m, COCHCH$_2$) ppm.

Synthesis of poly(amidoamine)-poly(β-benzyl L-aspartate)-poly(ethylene glycol)-OCH$_3$/Mal (abbreviated as PAMAM-PBLA-PEG-Mal): 1.25 mg (0.1 μmol) of PAMAM-COOH (G4 with 64 carboxyl terminal groups) and two types of PBLA-PEG block copolymers—namely, Mal-PEG-PBLA (7.2 mg, 0.77 μmol) and mPEG-PBLA (64.3 mg, 6.9 μmol)—were dissolved in 5 ml DMF. DCC (1.90 mg, 9 μmol) and NHS (1.0 mg, 9 μmol) were added to the above solution. The reaction was carried out at room temperature for 24 h. Then, the solution was dialyzed against deionized water (DI water) (molecular weight cut-off (MWCO) of 15 kDa) for 48 h to remove the impurities. The final product was collected after lyophilization. The chemical structure was confirmed by $^1$H NMR (400 MHz, dimethyl sulfoxide (DMSO)-D6). PAMAM-PBLA-PEG-Mal: 7.30-7.10 (105H, m, Ar—H), 6.90 (0.5H, s, Mal), 4.90-5.00 (40H, s, CH$_2$—Ar), 4.60-4.50 (20H, m, COCHCH$_2$), 3.22-3.50 (450H, m, CH$_2$CH$_2$O from PEG), and 2.50-2.80 (41H, m, COCHCH$_2$) ppm.

Synthesis of poly(amidoamine)-poly(aspartate diethyltriamine)-poly(ethylene glycol)-OCH$_3$/Mal (abbreviated as PAMAM-PAsp(DET)-PEG-Mal): PAMAM-PBLA-PEG-Mal (20 mg, 0.069 μmol) was dissolved in 5 ml DMF. DET (224 μl, 2.07 mmol) was added to the above solution dropwise at 4° C. over 1 h. Then the reaction mixture was stirred at room temperature for another 4 h. Thereafter, the resulting solution was added in 10 mL DI water, neutralized to pH of 7 using 1 M HCl, and then dialyzed against DI water (MWCO=15 kDa) for 48 h. The chemical structure was confirmed by $^1$H NMR (400 MHz, D$_2$O). PAMAM-PAsp(DET)-PEG-Mal: 6.90 (0.5H, s, Mal), 4.80-4.50 (20H, s, COCHCH$_2$), 4.00-3.60 (450H, m, CH$_2$CH$_2$O from PEG), 3.30 (40H, s, CONHCH$_2$), 3.10-2.98 (81H, m, CH$_2$NHCH$_2$), 2.75 (41H, CH$_2$NH$_2$), and 2.40-2.25 (m, 84H, COCHCH$_2$) ppm.

Synthesis of poly(amidoamine)-poly(aspartate diethyltriamine-r-imidazole)-poly(ethylene glycol)-OCH$_3$/Mal (abbreviated as PAMAM-PAsp(DET-r-Im)-PEG-Mal): PAMAM-PAsp(DET)-PEG-Mal (20 mg, 0.067 μmol), 4-imidazolecarboxylic acid (1.13 mg, 10 μmol), DCC (2.06 mg, 10 μmol), and NHS (1.15 mg, 10 μmol) were dissolved in 5 ml DMF. The solution was stirred at room temperature for 24 h at pH of 6.5. Thereafter, the impurities were removed by dialysis against DI water (MWCO 15 kDa) for 48 h. The chemical structure was confirmed by $^1$H NMR (400 MHz, $D_2O$). PAMAM-PAsp(DET-r-Im)-PEG-Mal: 8.24-8.22 (5H, s, Im), 7.53-7.52 (5H, d, Im), 6.90 (0.5H, s, Mal), 4.80-4.50 (20H, s, $COCHCH_2$), 4.00-3.50 (450H, m, $CH_2CH_2O$ from PEG), 3.30 (40H, s, $CONHCH_2$), 3.10-2.98 (80H, m, $CH_2NHCH_2$), 2.75 (40H, $CH_2NH_2$), and 2.70-2.50 (m, 81H, $COCHCH_2$) ppm.

Synthesis of poly(amidoamine)-poly(aspartate diethyltriamine-aconitic acid-r-imidazole)-poly(ethylene glycol)-$OCH_3$/Mal (abbreviated as PAMAM-PAsp(DET-Aco-r-Im)-PEG-Mal) (also referred to herein as polyamidoamine-poly(aspartyl-diethyltriamine-cis-aconitate/imidazole carboxylate)-poly(ethylene glycol)-$OCH_3$/Mal (i.e., PAMAM-P(Asp-DET-Aco/ICA)-PEG-Mal): PAMAM-PAsp(DET-r-Im)-PEG/Mal (20 mg, 0.062 µmol) and aconitic anhydride (109 mg, 0.7 mmol) were dissolved in 0.5 M $NaHCO_3$ buffer (5 ml, pH 9.0). The solution was stirred at 0° C. for the first 4 h followed by another 24 h at room temperature. The reaction mixture was purified by dialysis against DI water (MWCO 15 kDa) for 48 h. The final product was obtained as a white powder after lyophilization. The chemical structure was confirmed by $^1$H NMR (400 MHz, $D_2O$). PAMAM-PAsp(DET-Aco-r-Im)-PEG-Mal: 8.24-8.22 (5H, s, Im), 7.53-7.52 (5H, s, Im), 6.90 (0.5H, s, Mal), 5.82-5.72 (15H, s, $COCHC(COOH)CH_2COOH$), 4.80-4.50 (20H, s, $COCHCH_2$), 4.00-3.50 (450H, m, $CH_2CH_2O$ from PEG), 3.30 (40H, s, $CONHCH_2$), 3.10-2.98 (82H, m, $CH_2NHCH_2$), 2.75 (41H, $CH_2NH_2$), 2.70-2.50 (m, 81H, $COCHCH_2$), 1.80 (30H, s, $COCHC(COOH)CH_2COOH$) ppm.

Synthesis of PAMAM-PAsp(DET-Aco-r-Im)-PEG-TAT: TAT, a cell penetrating peptide was conjugated to the PAMAM-PAsp(DET-Aco-r-Im)-PEG-Mal polymer by a thiol-maleimide reaction. The molar ratio of TAT:PAMAM-PAsp(DET-Aco-r-Im)-PEG-Mal was set at 3:1. Briefly, PAMAM-PAsp(DET-Aco-r-Im)-PEG (20 mg, 0.052 µmol) was dispersed in PBS buffer (pH 7.4, 5 ml). TAT (0.3 mg, 0.19 µmol) and TECP (0.57 mg, 2 µmol) were added to the above solution. The reaction was carried out at room temperature for 24 h. Then, the solution was purified by dialysis against DI water (MWCO 15 kDa) for 48 h. The final product was obtained as a white powder after lyophilization. The chemical structure was confirmed by $^1$H NMR (400 MHz, $D_2O$). PAMAM-PAsp(DET-Aco-r-Im)-PEG-TAT: 8.24-8.22 (5H, s, Im), 7.55-7.30 (15H, m, Im and TAT), 5.82-5.72 (15H, s, $COCHC(COOH)CH_2COOH$), 4.80-4.50 (20H, s, $COCHCH_2$), 4.00-3.50 (450H, m, $CH_2CH_2O$ from PEG), 3.30 (40H, s, $CONHCH_2$), 3.10-2.98 (82H, m, $CH_2NHCH_2$), 2.75 (41H, $CH_2NH_2$), 2.70-2.50 (m, 81H, $COCHCH_2$), 1.80 (30H, s, $COCHC(COOH)CH_2COOH$) ppm.

Preparation of PKM2 peptide-loaded UMNPs: A 6-carboxyfluorescein (FAM)-conjugated PKM2 peptide (FAM-PKM2 peptide, prepared by Genemed Synthesis Inc., San Antonio, Tex., using standard solid phase peptide synthesis methods) solution was prepared by dissolving 0.5 mg of the FAM-PKM2 peptide in 0.5 ml DI water under stirring. The UMNP solution was prepared by dissolving 2 mg of the PAMAM-PAsp(DET-Aco-r-Im)-PEG-TAT polymer in 1 ml DI water with its pH adjusted to 7. The UMNP solution was slowly added to the peptide solution and the resulting mixture was stirred at room temperature for 4 h. Thereafter, the solution was dialyzed against DI water (MWCO=100 kDa) and lyophilized. UMNP-non-methyl peptide and UMNP-methyl peptide without FAM conjugation were prepared by the same method.

Example 2: CARM1 Interacts with and Methylates PKM2

Figure 1B:
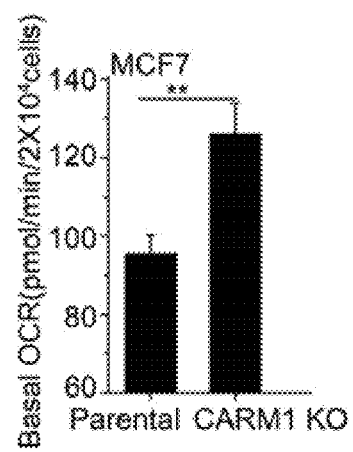
Figure 1C:
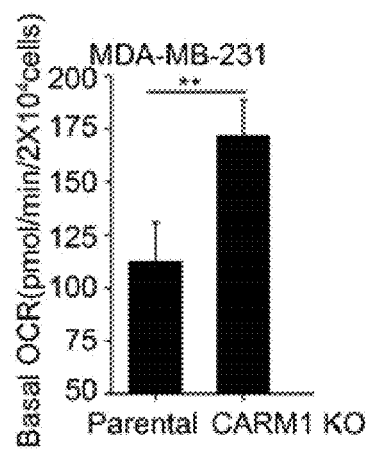
Figure 1D:
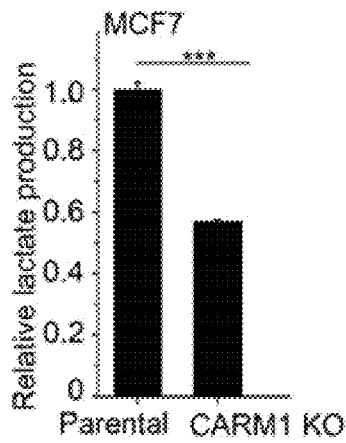
Figure 1E:
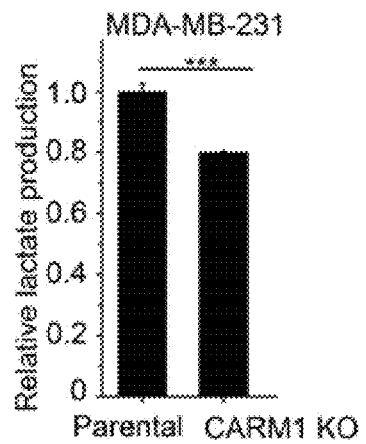
Figure 1F:
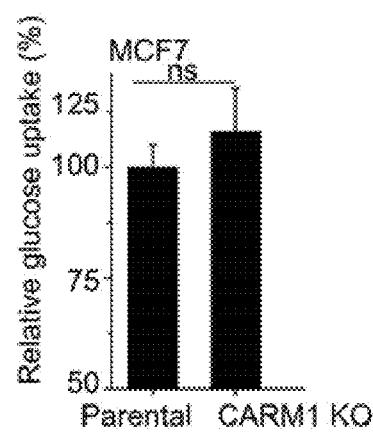

Consistent with the previous reports that CARM1 promotes tumor development and progression, knocking out (KO) CARM1 in MCF7 cells resulted in decreased DNA synthesis in MCF7 cells (FIG. 1A: Cells were incubated with 10 µM EdU for 1 hour prior to flow cytometric analysis (n=3)). CARM1 KO also increased mitochondrial oxygen consumption rate (OCR) without affecting glucose uptake (FIGS. 1B, 1C). (FIG. 1B: Basal OCR values normalized to cell numbers in parental MCF7 and CARM1 KO cells (n=6); FIG. 1C: Glucose uptake assays in parental MCF7 and CARM1 KO cells (n=3)).

Figure 2A:
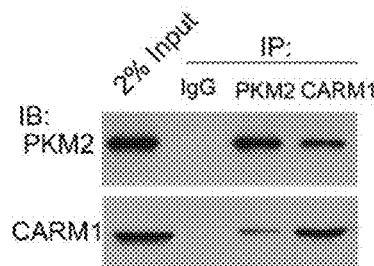
FIGS. 2A-2G show that the dimeric form of PKM2 is methylated by CARM1.
Figure 2B:
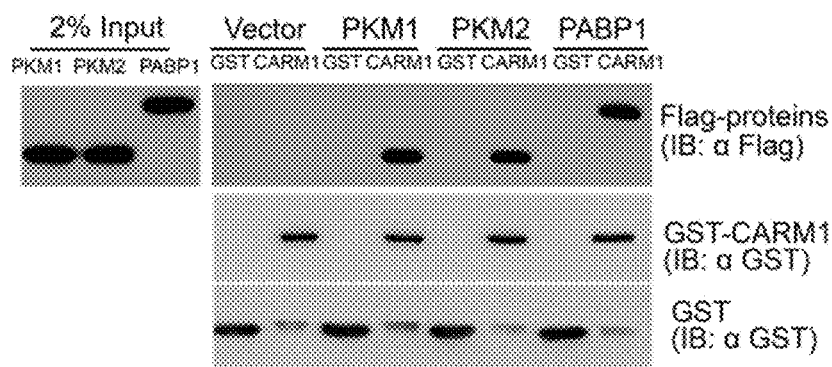
Figure 2C:
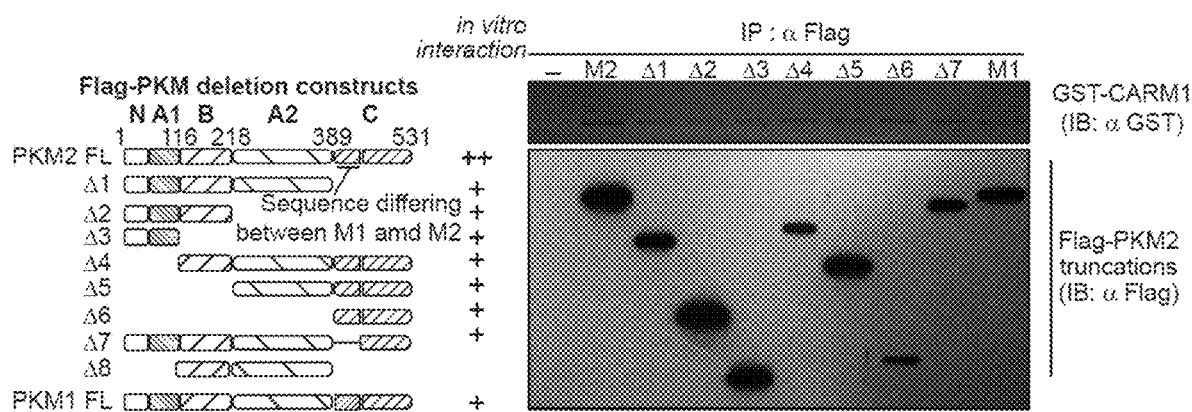
Figure 2D:
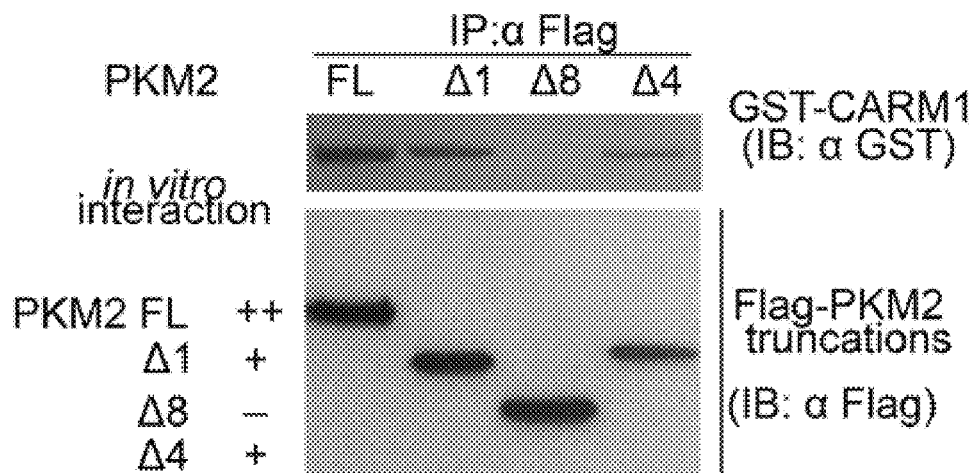
Figure 2E:
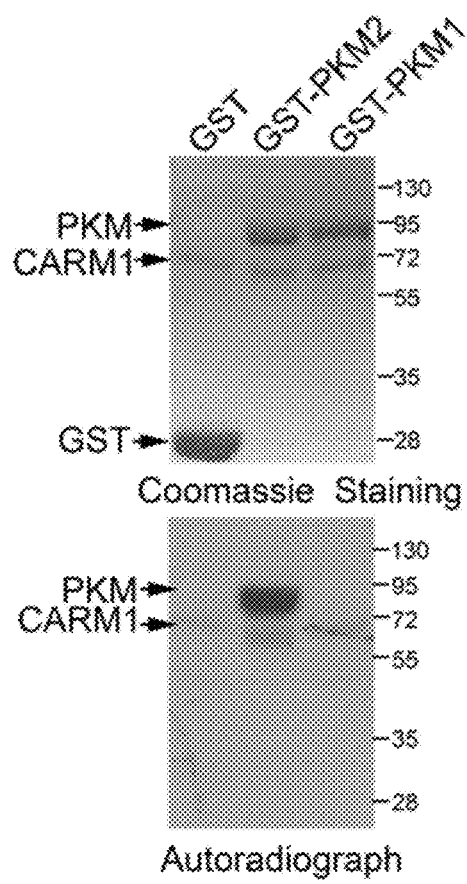

Experiments were therefore conducted to determine whether CARM1 is involved in energy metabolism in breast cancer cells. PKM2 was previously identified as a putative CARM1 interacting protein by mass spectrometry when CARM1 was overexpressed using a Halo-tag mammalian expression system in HEK293T cells. The interaction of endogenous CARM1 and PKM2 was confirmed by reciprocal coimmunoprecipitation in MCF7 cells (FIG. 2A). To determine whether CARM1 directly interacts with PKM2, GST pull-down assays were performed using purified, recombinant, glutathione S-transferase (GST) tagged CARM1 and Flag-tagged PKM2. These experiments showed that GST-CARM1, but not GST alone, is associated with PKM2, indicating a direct interaction between PKM2 and CARM1 (FIG. 2B). Interestingly, recombinant PKM1 was also found to be associated with CARM1 in vitro (FIG. 2B). To map the region of PKM2 that binds to CARM1, a series of truncated Flag-PKM2 was expressed using an in vitro transcriptional and translational system and performed in vitro interaction assays with GST-CARM1. As shown in FIGS. 2C and 2D, deletion of the C domain (Δ1) or N/A1 domain (Δ4) of PKM2 significantly decreased PKM2 interaction with CARM1, and truncation of both domains (Δ8) completely abolished PKM2 interaction with CARM1. Not wishing to be bound by theory, it is speculated that the C and N/A1 domains are responsible for the interaction. Although these domains are identical between PKM1 and PKM2, intriguingly only PKM2, but not PKM1, can be methylated by CARM1 in in vitro methylation assays (FIG. 2E).

Figure 2F:
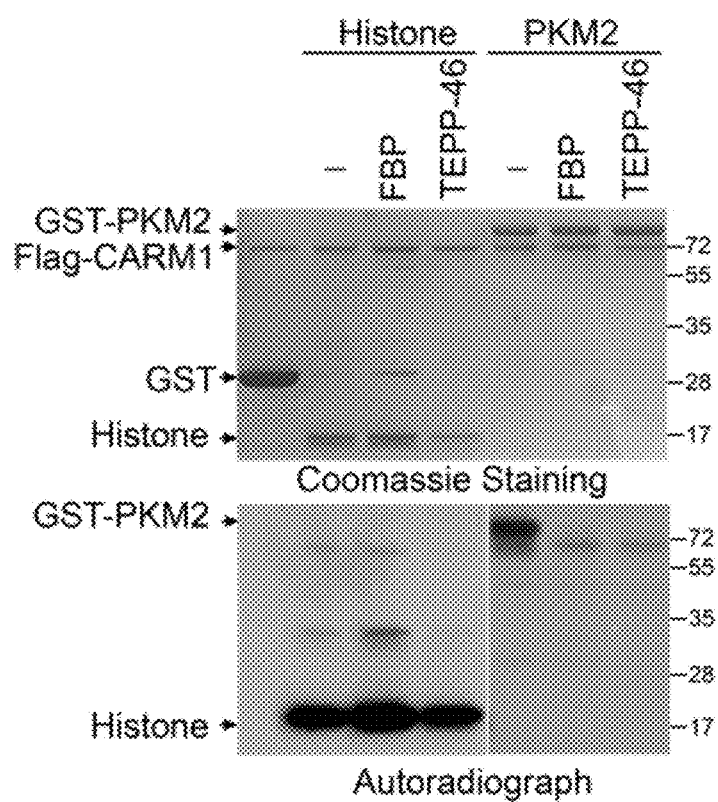
Figure 3A:
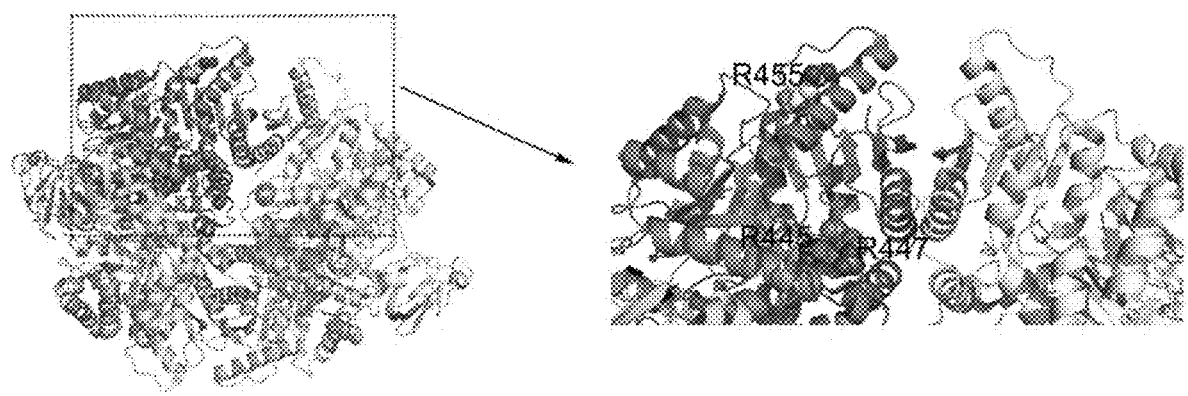
FIGS. 3A-3C shows that TEPP-46 promotes PKM2 tetramer formation, whereas R445/447/455K mutations on neither PKM1 nor PKM2 alter their di-/tetra-merization status.
Figure 3B:
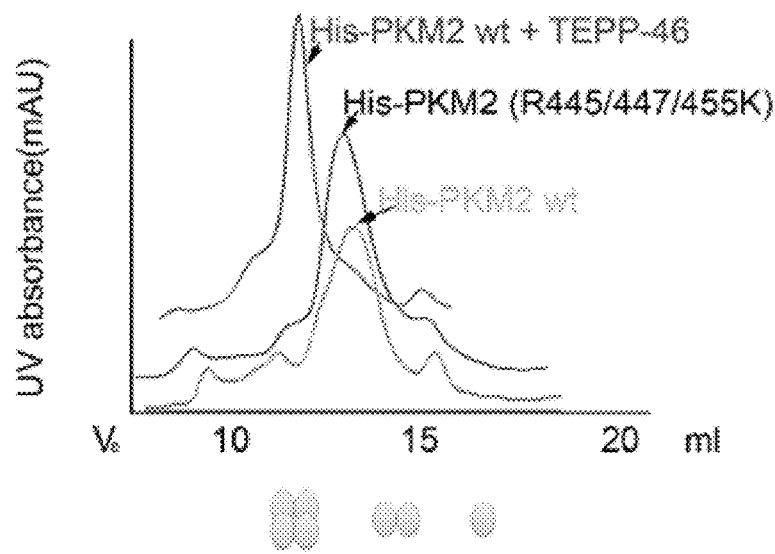
Figure 3B:
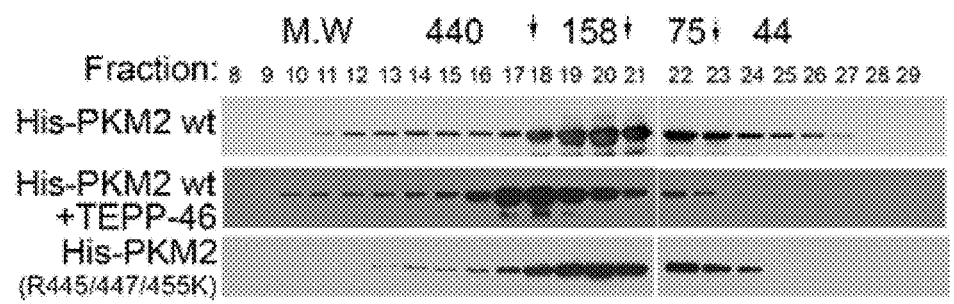

Because CARM1 directly interacts with both PKM1 and PKM2 through the conserved N/A1 and C domains yet methylate PKM2 and not PKM1, the influence of PKM tetramer/dimer status on methylation was tested. Given that PKM1 exists in the tetramer form while PKM2 is in tetramer and dimer forms, it was hypothesized that tetramer formation may prevent CARM1-mediated methylation. TEPP-46, a PKM2 activator, was employed to promote PKM2 tetramer formation (FIGS. 3A-3B). Conversion of PKM2 from dimer to tetramer by TEPP-46 or FBP, resulted in blockage of PKM2 methylation by CARM1 (FIG. 2F). As controls, neither TEPP-46 nor FBP treatment affected histone H3 methylation by CARM1 (FIG. 2F), excluding the possibility that TEPP-46 and FBP interfere with CARM1 methyltransferase activity. Collectively, these data demonstrate that the dimeric form, and not the tetrameric form, of PKM2 is methylated by CARM1.

Figure 2G:
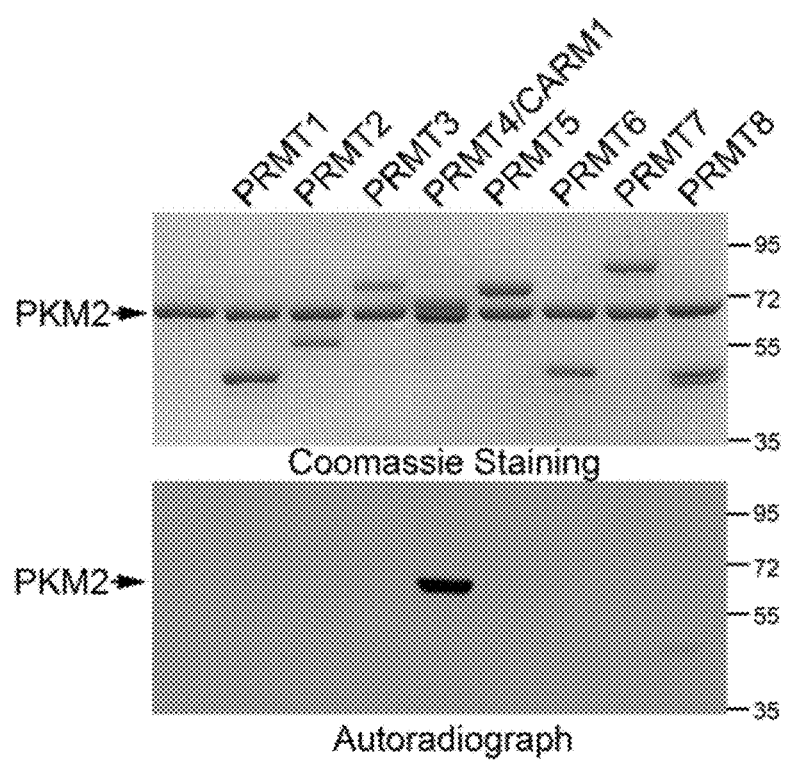

Nine PRMTs are encoded in the mammalian genomes. They sometimes share the same substrates but methylate different sites or methylate the same site by Type I and II PRMTs to form asymmetric or symmetric di-methylated arginines. To examine if PKM2 can be methylated by other PRMTs, eight PRMTs (1-8) were purified from HEK293T using Halo-tag expression system (Wang et al., 2014) and in vitro methylation assays were conducted using recombinant PKM2 protein. The result showed that PKM2 is uniquely methylated by CARM1 (FIG. 2G).

Example 3: CARM1 Methylates PKM2 at R445/447/455

Figure 3C:
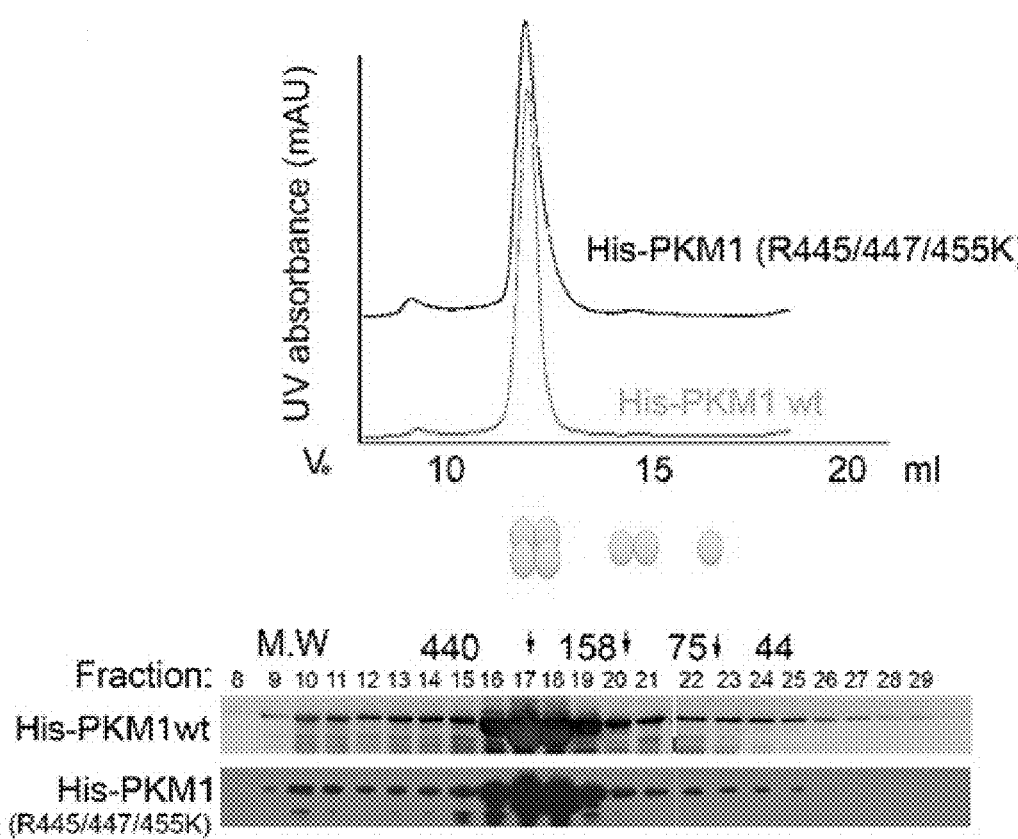
Figure 4A:
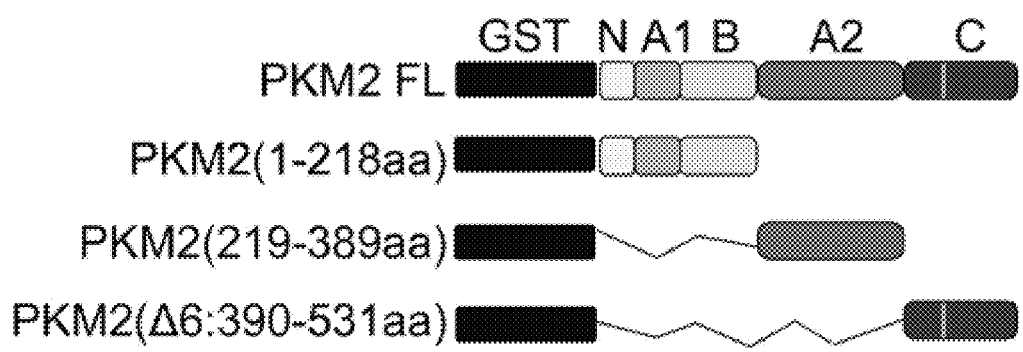
FIGS. 4A-4E show that CARM1 methylates PKM2 at R445, R447 and R455.
Figure 4B:
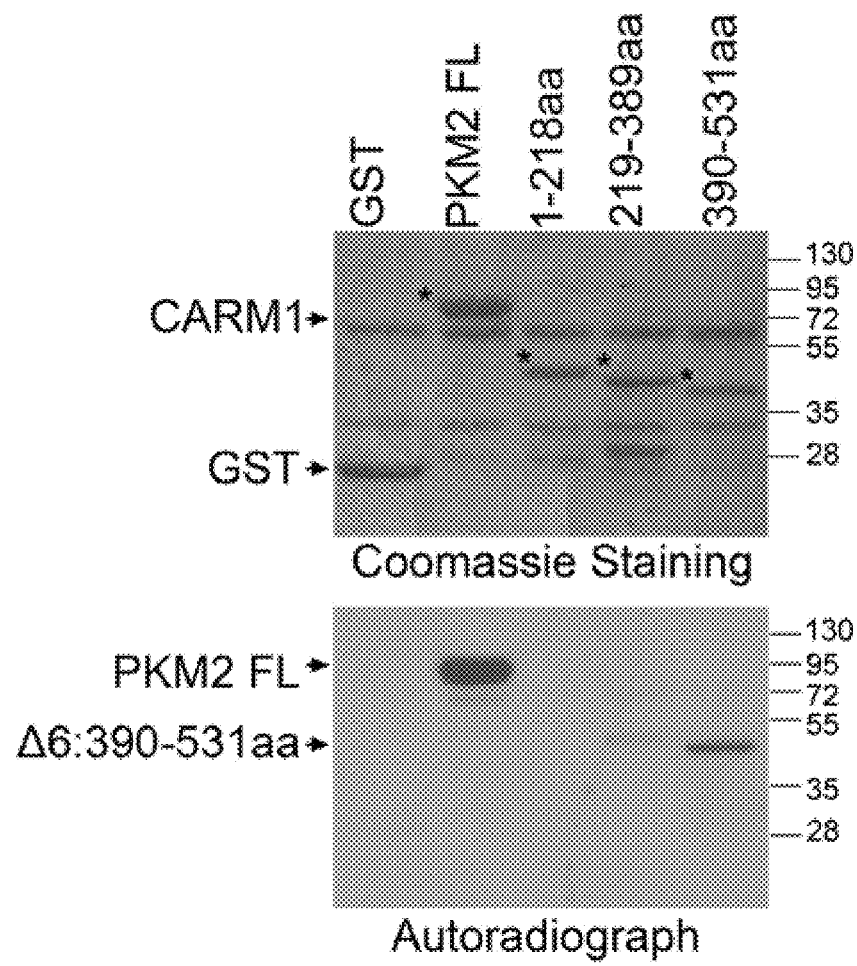
Figure 4C:
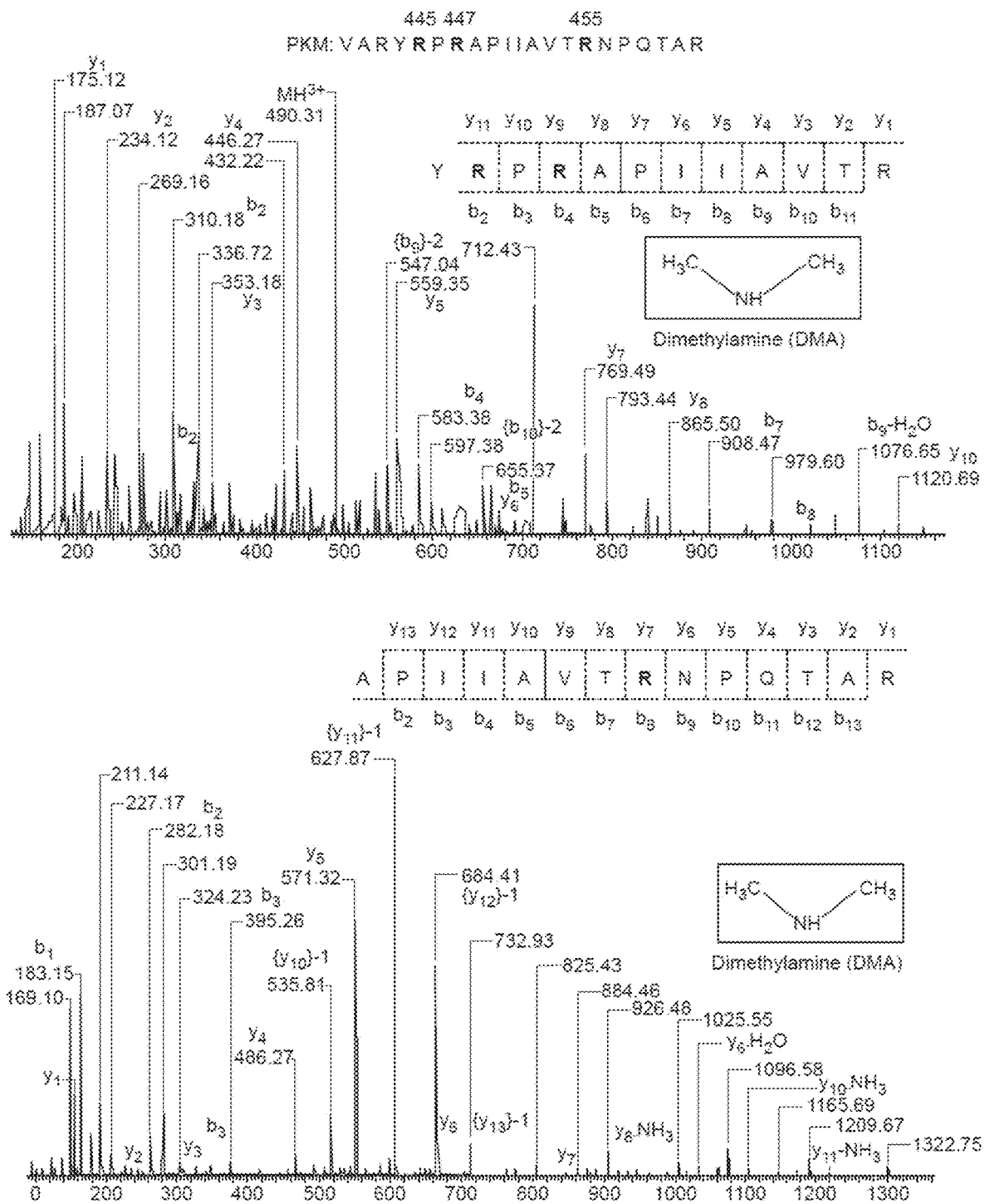
Figure 4D:
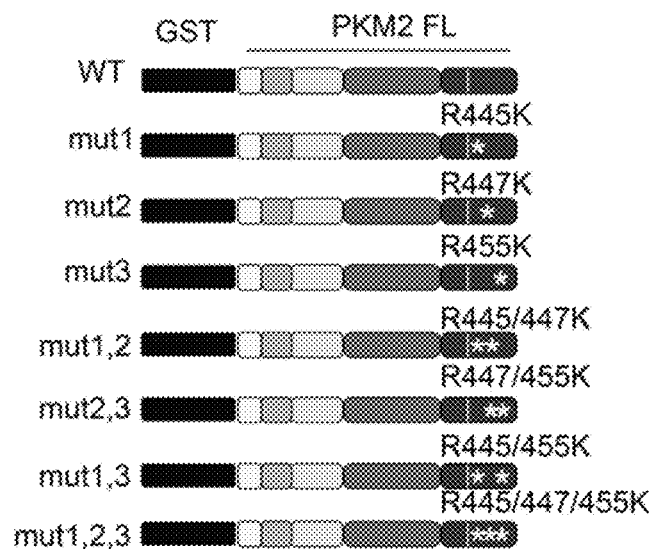
Figure 4E:
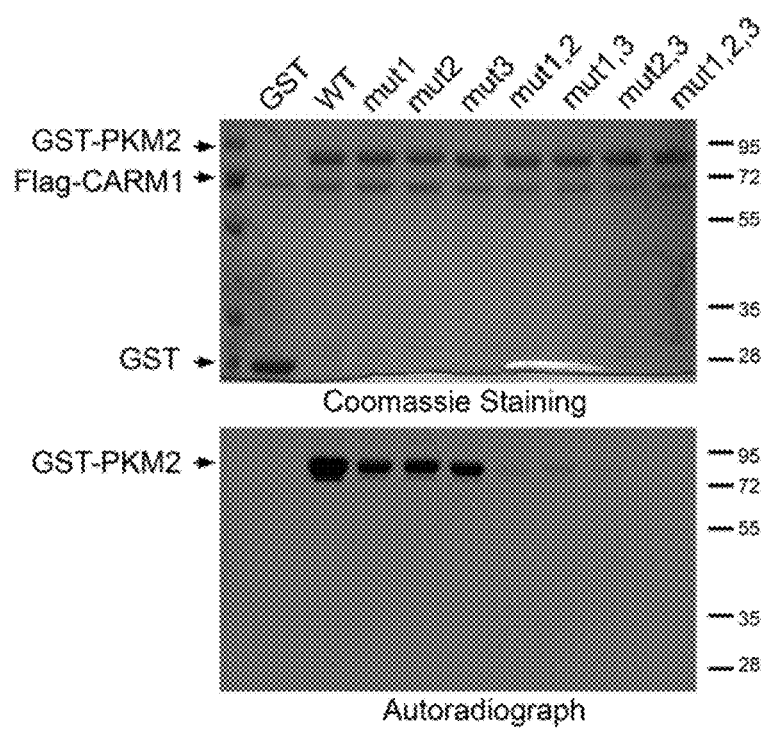

To narrow down the methylation domain(s) in PKM2, in vitro methylation assays were performed using the purified GST tagged full-length (FL) or truncated PKM2 proteins (FIG. 4A). Among the three truncated fragments, FL PKM2 and the C-domain, but not the other domains, are methylated (FIG. 4B), suggesting that PKM2 methylation site(s) might reside in the C-domain. Indeed, three arginine residues (R445, R447 and R455) were identified from the in vitro methylated GST-PKM2 (390-531 aa) fragment using liquid chromatography coupled with mass spectrometry (LC-MS) (FIG. 4C). To further discern the major methylation site(s), three methylated R sites were substituted with lysine to preserve the positive charge, individually or in combination, in the GST-PKM2 plasmids as illustrated in FIG. 4D. Corresponding proteins were purified and used for in vitro methylation assays. While single mutation of each of the three sites had little effect on PKM2 methylation (FIG. 4E), mutation of any two of the three sites dramatically decreased PKM2 methylation, and methylation was abrogated when all three sites were mutated (FIG. 4E). All three-arginine residues are located in the C domain, which fosters tetramer formation. However, neither site is directly localized in the tetrameric interface (FIG. 3A). All three arginine residues were mutated to lysine in PKM1 and PKM2 constructs and size exclusion chromatography was performed using purified recombinant His-tagged proteins. The chromatography results showed that neither PKM2 (FIG. 3B) nor PKM1 tetramer (FIG. 3C) formation was affected by R445, R447, and R455 mutations. These results suggest that CARM1 predominantly methylates dimeric PKM2, yet PKM2 tetramer formation is not affected by PKM2 methylation. While not being limited to a particular theory, it is possible that PKM1 may not methylated by CARM1 because the corresponding arginine residues in PKM1 tetramer are inaccessible to CARM1.

Figures 5A, 5B:
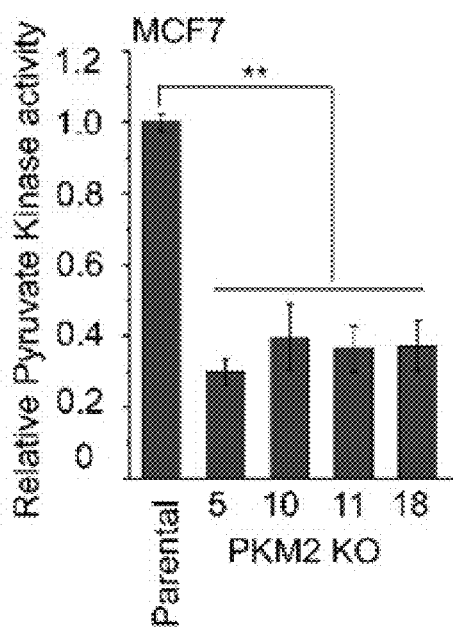
FIGS. 5A-5J show the characterization of PKM2 KO clones.
Figure 5C:
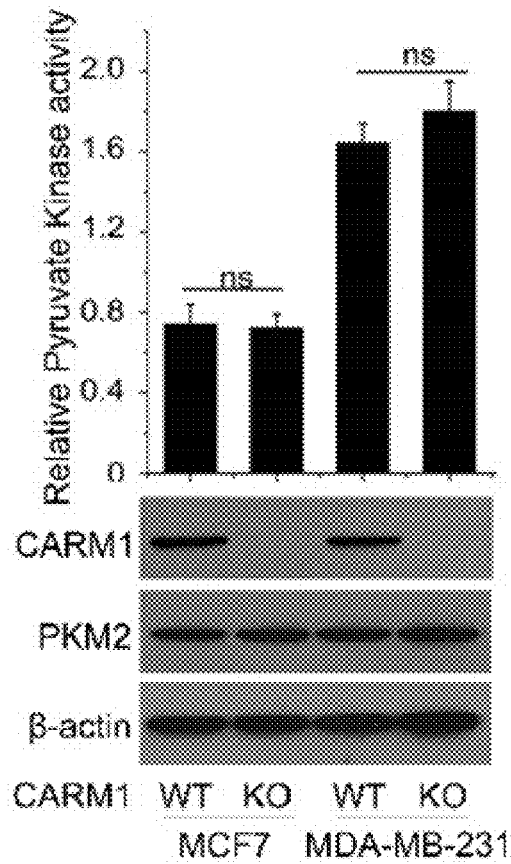
Figure 6A:
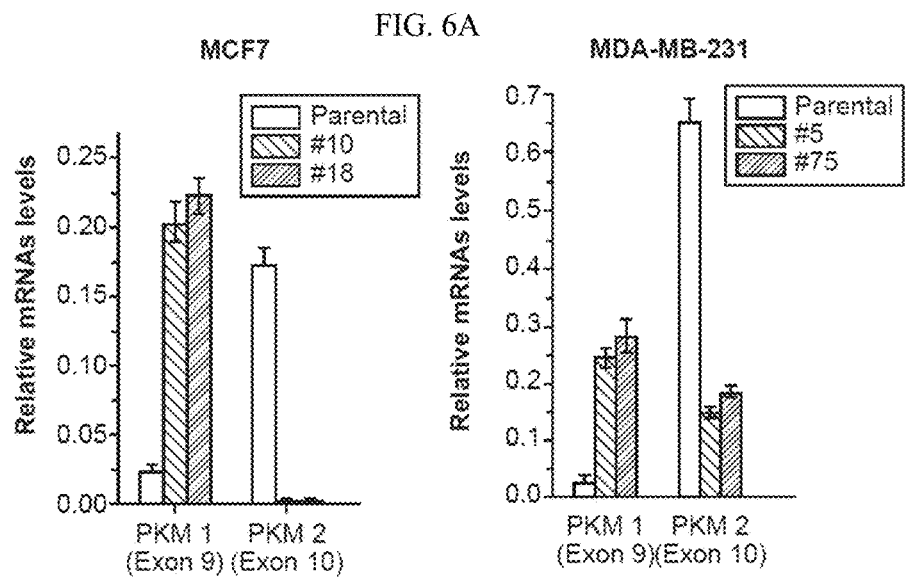
FIGS. 6A-6J show that inhibition of PKM2 methylation decreases cell proliferation and migration. (6A) Q-PCR analyses of mRNA levels of PKM1 and PKM2 in parental MCF7 and MDA-MB-231 cells and their respective PKM2 KO clones (n=3). (6B) Western blot analyses of PKM1 and PKM2 in parental MCF7 and MDA-MB-231 cells and their respective PKM2 KO clones. (6C) Mass spectrometry analysis of global protein changes between parental MCF7 and PKM2 KO cells (n=3). (6D) EdU incorporation assays of parental MCF7 and PKM2 KO clones (n=3). (6E) Cell cycle analyses of parental MCF7 and MCF7 PKM2 KO clones. (6F) Western blot analysis of PKM2, methyl-PKM2 and PKM1 in parental, PKM2 KO, PKM2 KO restored with PKM2$^{wt}$ and PKM2$^{mut}$ in accompanying with PKM1 knockdown in MCF7 and MDA-MB-231 cells. (6G) Measurement of cell proliferation by MTT assays in parental MCF7, PKM2 KO, PKM2$^{wt}$/shPKM1, and PKM2$^{mut}$/shPKM1 cells (n=10). (6H) Measurement of cell migration by transwell assays in parental MDA-MB-231, PKM2 KO, PKM2$^{wt}$/shPKM1, and PKM2$^{mut}$/shPKM1 cells (n=3). (6I) The growth curves of MDA-MB-231 PKM2$^{wt}$/shPKM1 and PKM2$^{mut}$/shPKM1 xenografts (n=6). (6J) Representative images of the xenograft tumors. Statistical significance was assessed using ANOVA. Mean±SD, p<0.01, *p<0.001.
Figure 6B:
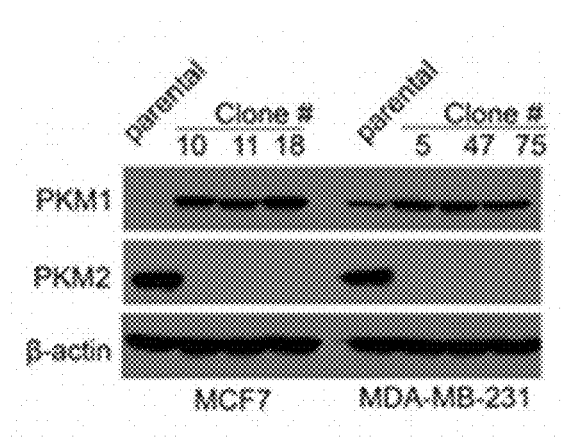
Figure 6C:
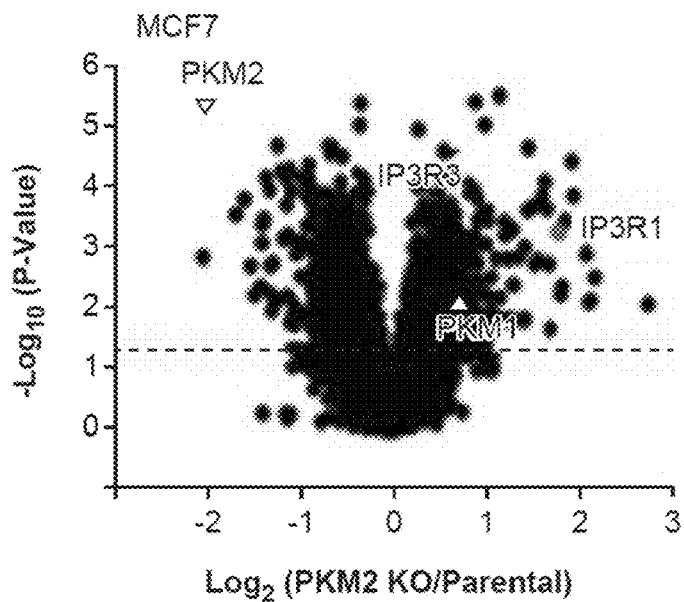

Example 4: Inhibition of PKM2 Methylation Decreases Breast Cancer Cell Proliferation and Migration To investigate the function of PKM2 methylation in breast cancer cell line models, CRISPR/Cas9-based genomic editing technology was employed to specifically knock out (KO) endogenous PKM2. The human PKM2 gene locus resides in chromosome 15q22, a region quadruplicated in MCF7 but single-copied in MDA-MB-231 cells. Genomic DNA sequencing analyses of two representative PKM2 KO clones of MCF7 or MDA-MB-231 revealed non-homologous end jointing (NHEJ), which creates random insertions or deletions at the targeted site (FIG. 5A). These NHEJ resulted in mRNA degradation and PKM2 deletion (FIGS. 6A, B). Specific PKM2 KO led to induction of PKM1 (FIGS. 6A, B), a compensatory phenomenon that has also been reported in primary mouse embryonic fibroblast (MEF) cells. To investigate the effect of PKM2 KO on whole proteome, the global protein changes in parental and PKM2 KO MCF7 cells were analyzed by LC-MS/MS. Whole proteome analysis showed that, among more than 4000 proteins detected, the levels of 158 proteins significantly increased (fold $>=1.5$, $p<0.05$), and 261 proteins decreased (fold $<=0.7$, $p<0.05$) in PKM2 KO vs. parental comparison (FIG. 6C). In agreement with specific PKM2 KO, PKM2 protein levels decreased by more than 5-fold and PKM1 increased by more than 1.6-fold. The total pyruvate kinase activity in PKM2 KO cells decreased as compared to the parental cells (FIG. 5B), even though the dimeric PKM2 has lower pyruvate kinase activity as compared to the tetrameric PKM1 with higher pyruvate kinase activity. While not being limited to a particular theory, it is possible that the level of restoration of PKM1 in PKM2 KO cells is insufficient to completely compensate the loss of PKM2. No detectable changes of PK activity were observed in the paired parental and CARM1 KO MCF7 and MDA-MB-231 cell lines (FIG. 5C), indicating that CARM1-mediated PKM2 methylation is unlikely to alter the PK activity of PKM2.

Figure 5D:
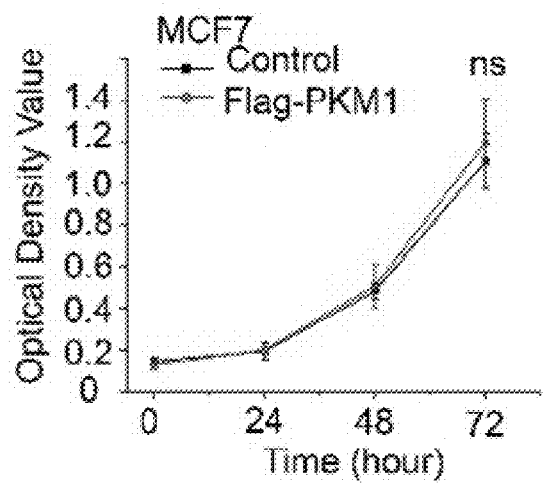
Figure 5E:
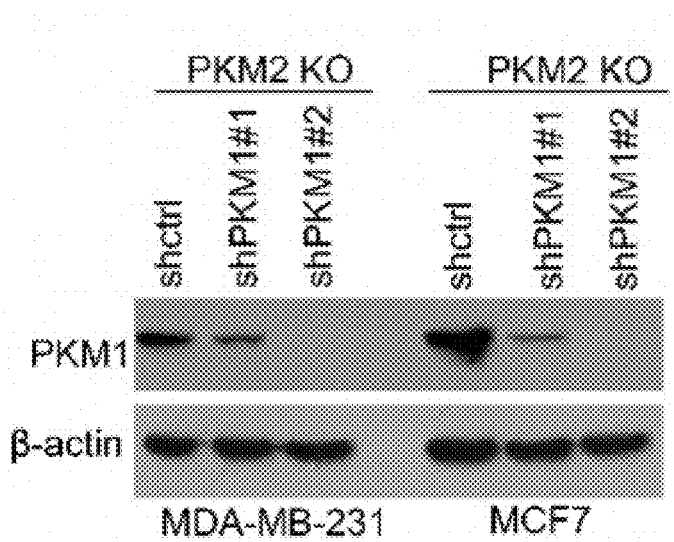
Figure 5F:
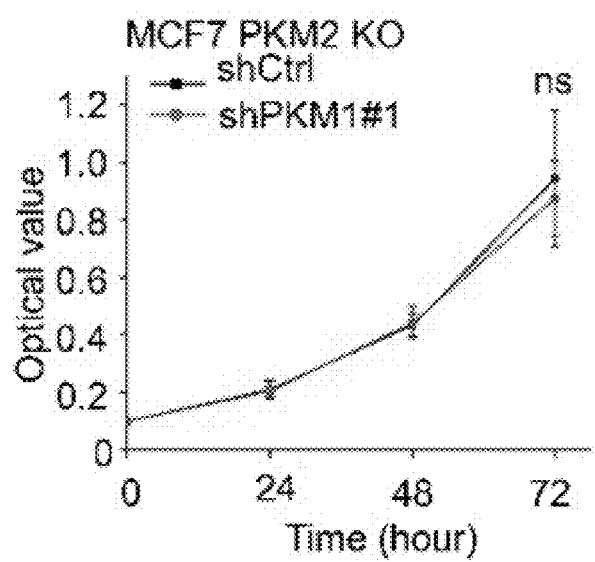
Figure 5G:
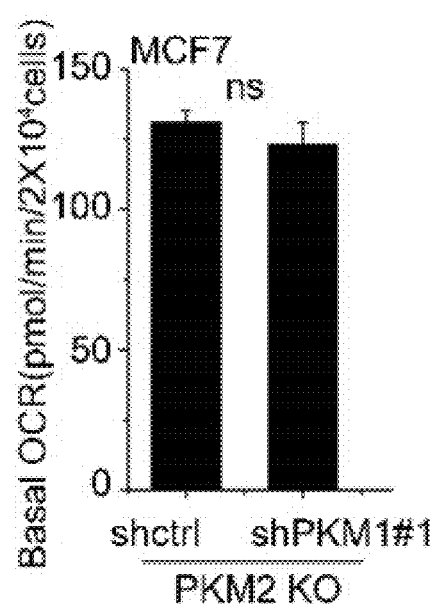
Figure 5H:
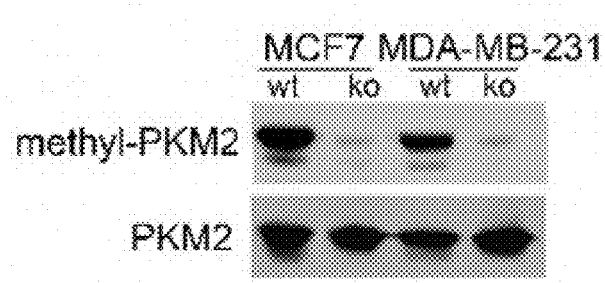
Figure 5I:
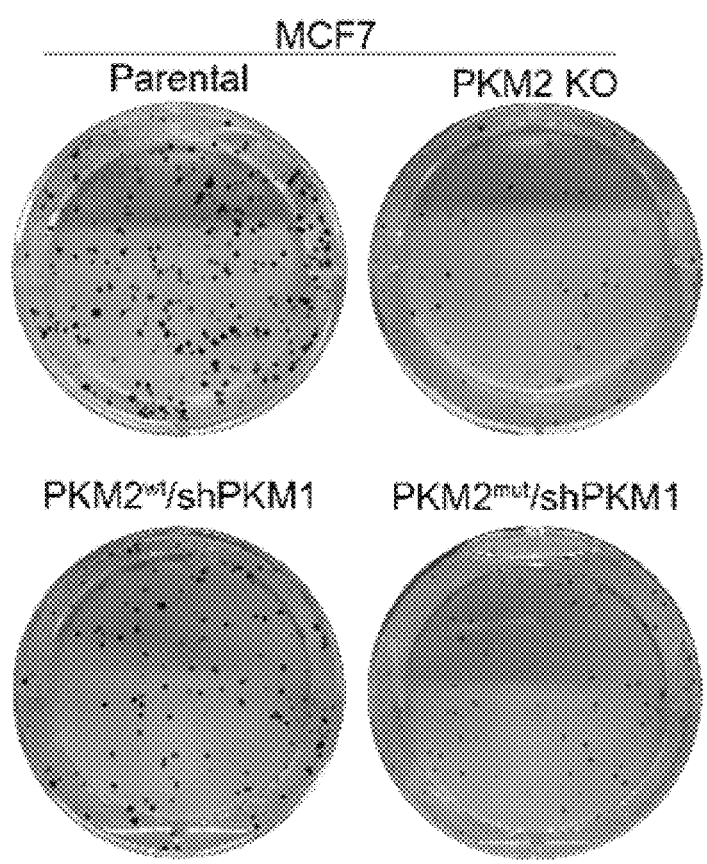
Figure 5J:
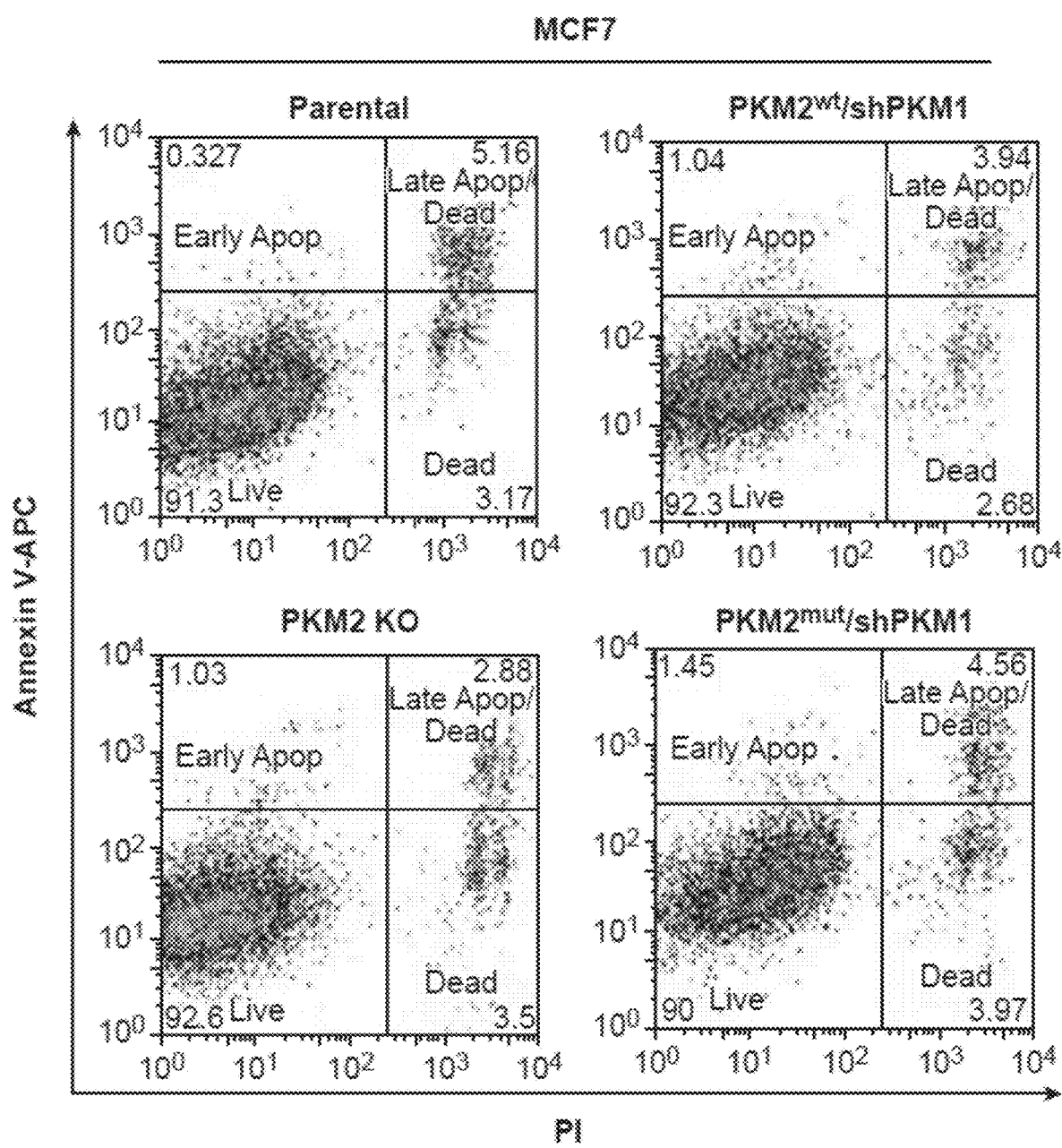
Figure 6D:
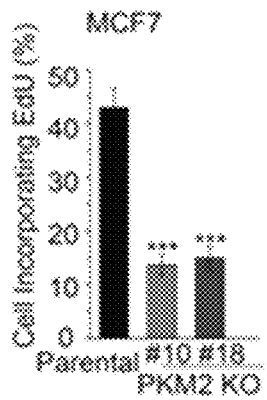
Figure 6E:
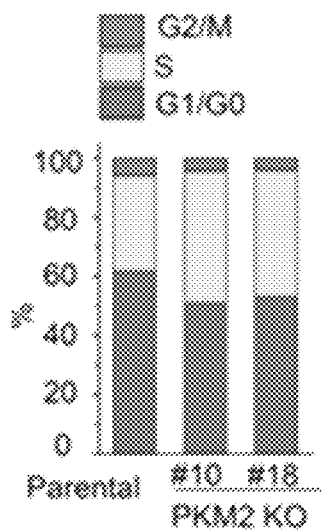
Figure 6F:
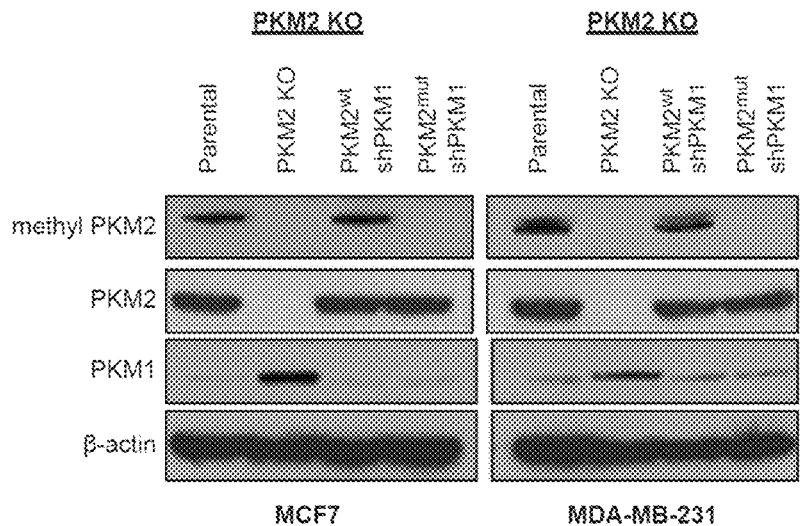
Figure 6G:
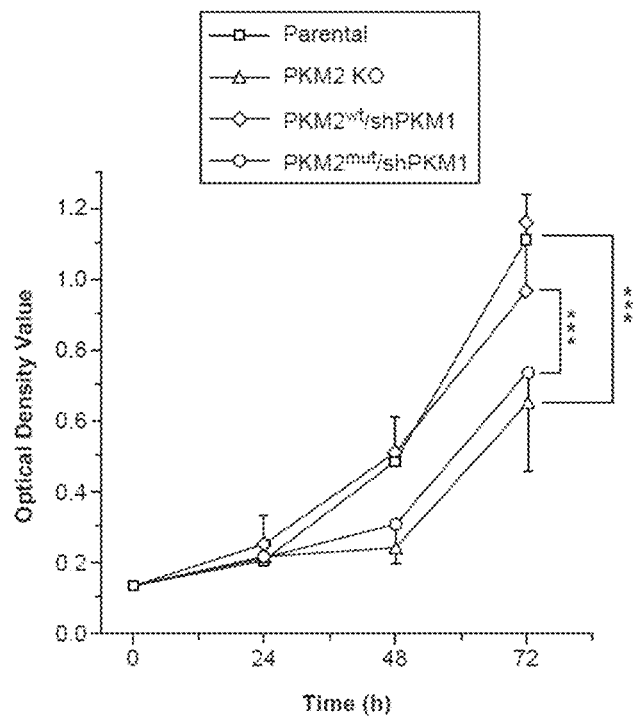
Figure 6H:
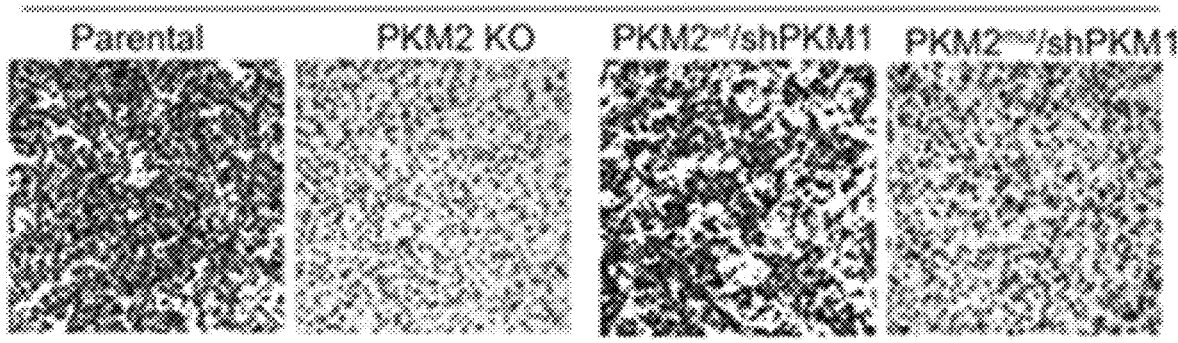
Figure 6I:
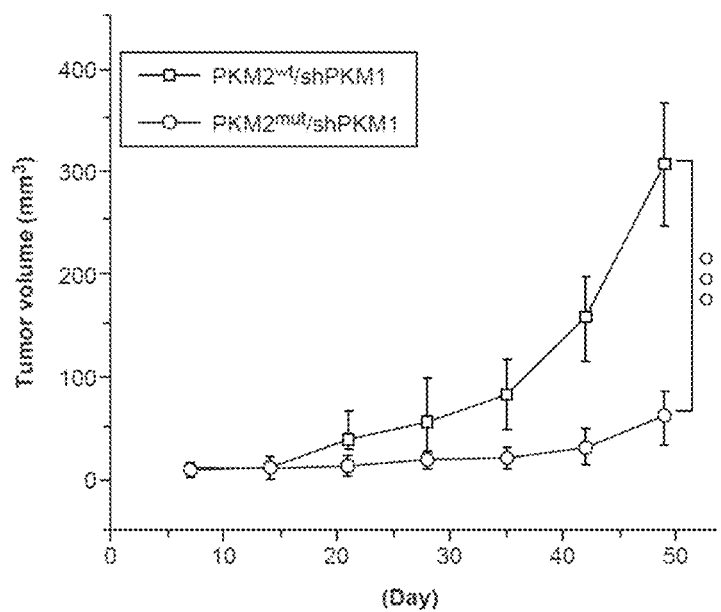
Figure 6J:
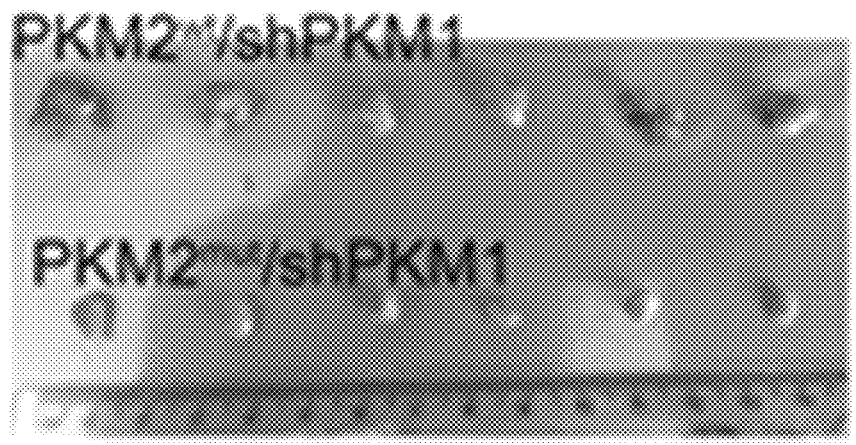

In MEF cells, deletion of PKM2 from one or both alleles resulted in PKM1 expression and proliferation arrest, and the reduced DNA synthesis is attributed to PKM1 expression, rather than PKM2 loss. Similarly, reduced DNA synthesis was observed, as measured by EdU incorporation and S-phase accumulation when PKM2 was knocked out from MCF7 cells (FIGS. 6D-6E). However, the mechanism of reduced DNA synthesis in MCF7 cells appears to differ from that of MEF cells. Consistent with previous report, massive reduction of nucleotides was observed in MEF cells when PKM2 was knocked out. See Lunt, S. Y. et al., "Pyruvate kinase isoform expression alters nucleotide synthesis to impact cell proliferation," *Mol Cell* 57, 95-107 (2015). In contrast, PKM2 KO did not induce global nucleotide shortage in MCF7 and MDA-MB-231 cells. This data rebuts the assumption that the reduced DNA synthesis in MCF7 cells was attributed to the shortage of nucleotides, as had been reported for MEF cells. Another difference between MCF7 and MEF lies in the growth inhibitory effect of PKM1. In contrast to MEF, overexpression of PKM1 in MCF7 cells did not affect cell proliferation (FIG. 5D), suggesting that overexpression of PKM1 is insufficient to inhibit MCF7 cell proliferation in the presence of PKM2 expression. To delineate the functions of PKM2 methylation on energy metabolism without the interference from PKM1, PKM2$^{wt}$ or PKM2$^{mut}$ (R445K, R447K and R455K) was restored in PKM2 KO cell lines, followed by knocking down (KD) PKM1 (FIG. 6F). It was observed that knocking down 60-80% PKM1 in PKM2 KO cells did not affect cell proliferation and oxidative phosphorylation (FIGS. 5E-5G). However, the cell viability was dramatically reduced (data not shown) when PKM1 knockdown reached nearly 100%, possibly because these cells have insufficient pyruvate kinase to support survival. To ensure that PKM2$^{mut}$ was defective in PKM2 methylation, an antibody was generated against asymmetrically dimethylated R445 and R447 peptide of PKM2, referred as the methyl-PKM2 antibody. While PKM2$^{wt}$ and PKM2$^{mut}$ were restored to the similar level, methylated PKM2 were detected in parental and PKM2$^{wt}$ expressing cells, but not in PKM2 KO or PKM2$^{mut}$ expressing cell (FIG. 6F) and in CARM1 KO cells (FIG. 5H), demonstrating the antibody specificity. These engineered cell lines were used to investigate the effects of methyl-PKM2 on cell proliferation and colony formation in MCF7 cells and cell migration in MDA-MB-231. The results showed that PKM2 methylation defective cells (e.g., PKM2 KO and PKM2$^{mut}$) elicited reduced proliferation and reduced colony formation (FIGS. 6G and 5I) compared to parental and PKM2$^{wt}$ MCF7 cells; however, these effects appeared not to be caused by apoptosis (FIG. 5J). PKM2 methylation status also affected the cell migration (FIG. 6H) and tumor growth of MDA-MB-231 xenografts (FIGS. 6I and 6J). Therefore, PKM2 methylation may be needed for promoting cell proliferation, migration, and tumor growth in various breast cancer cell line models.

Figure 13A:
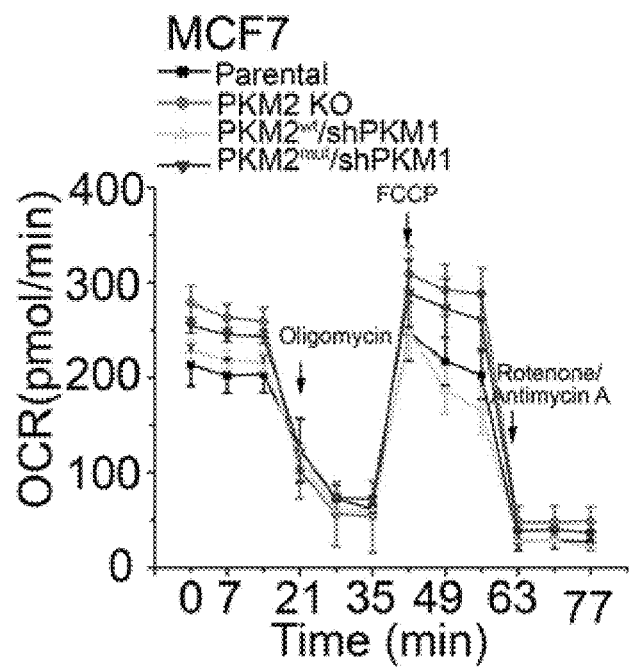
FIGS. 13A-13G show that the inhibition of PKM2 methylation results in an increase of mitochondria oxidative phosphorylation.
Figure 13B:
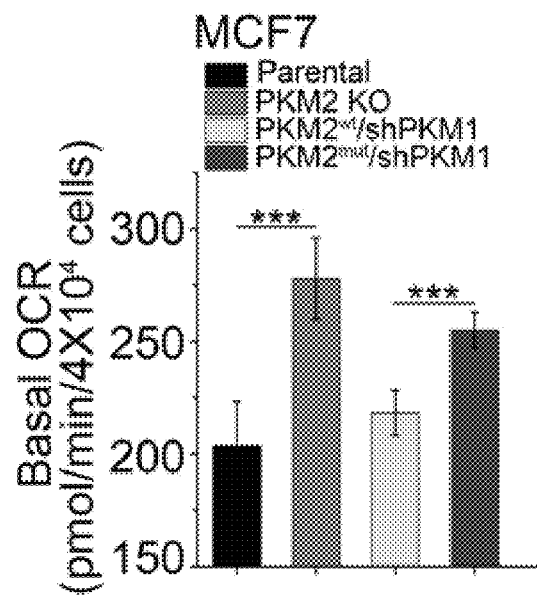
Figure 13C:
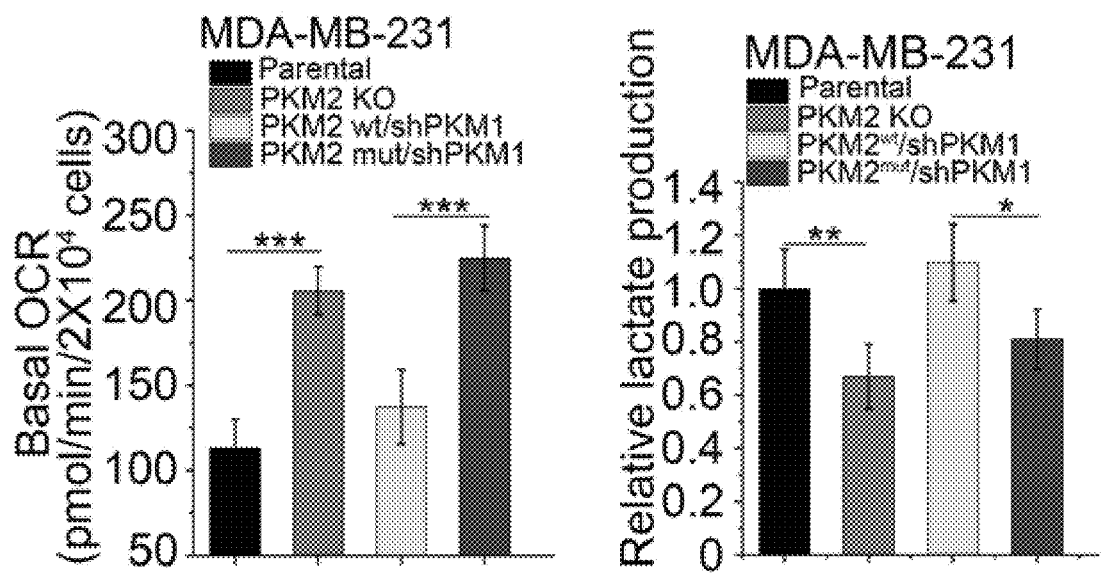
Figure 13D:
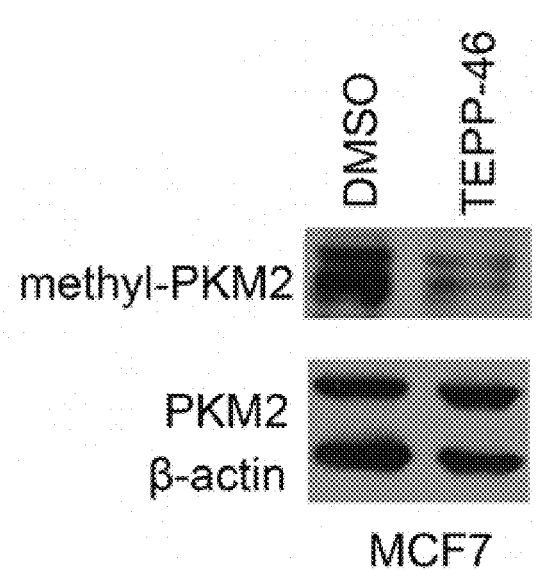
Figure 13E:
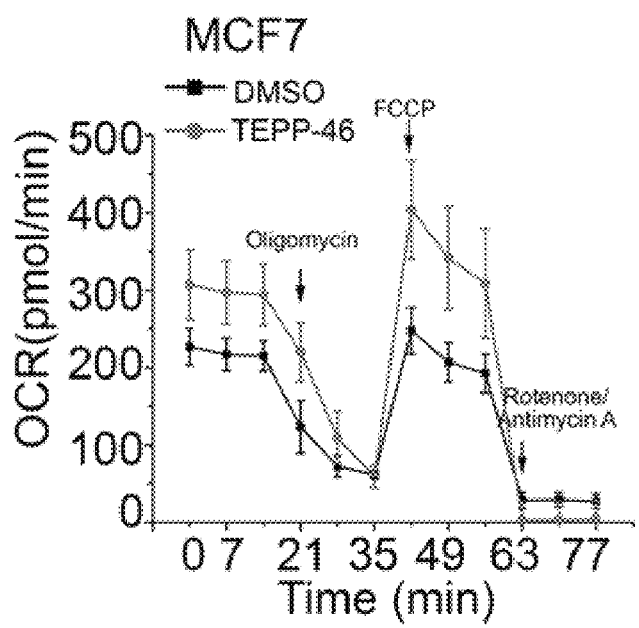
Figure 13F:
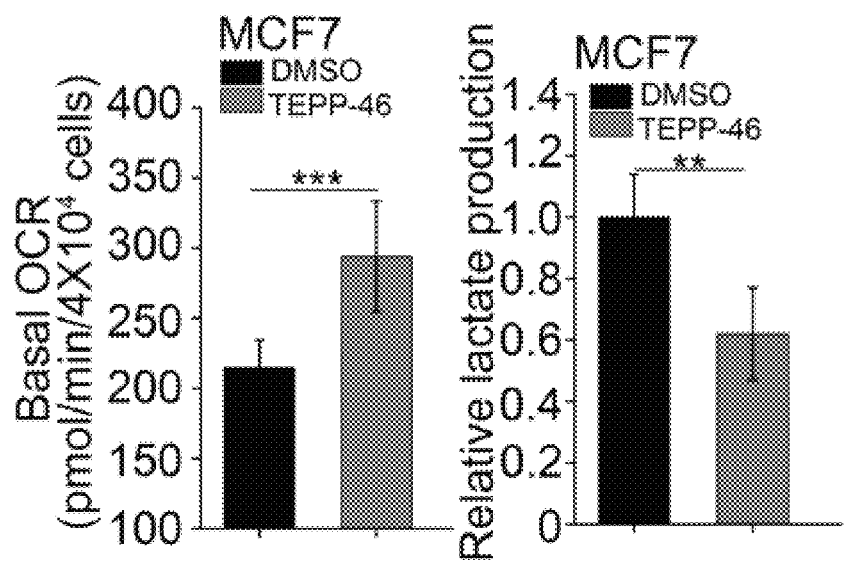
Figure 13G:
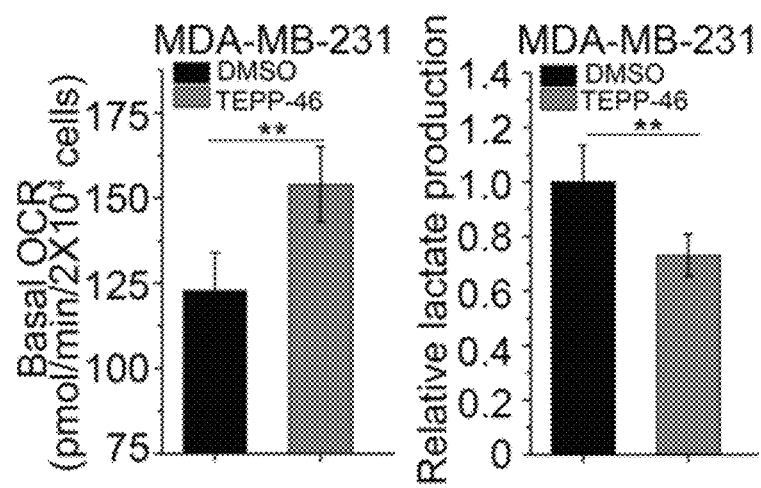

Example 5: Blocking PKM2 Methylation Results in Increase of Mitochondrial Respiration in Breast Cancer Cells Given that PKM2 methylation promotes cell proliferation and migration, whether PKM2 methylation regulates metabolic fluxes was examined by measuring the extracellular acidification rate (ECAR), an indicator of lactate production, and the OCR, an indicator of mitochondrial respiration. The switch from PKM2 to PKM1 in MCF7 and MDA-MB-231 PKM2 KO cells significantly increased OCR and reduced lactate (FIGS. 13A-13C). Remarkably, the balance of OCR and lactate production could be reversed by restoration of PKM2$^{wt}$, but not PKM2$^{mut}$ (FIGS. 13B-13C). In addition, TEPP-46 treatment, which triggers PKM2 tetramer formation thus blocking its methylation (FIGS. 2F and 13D), also significantly increased OCR while decreasing lactate production (FIGS. 13E-13G). These results suggest that PKM2 methylation modulates energy metabolism in cancer cells.

Figure 7A:
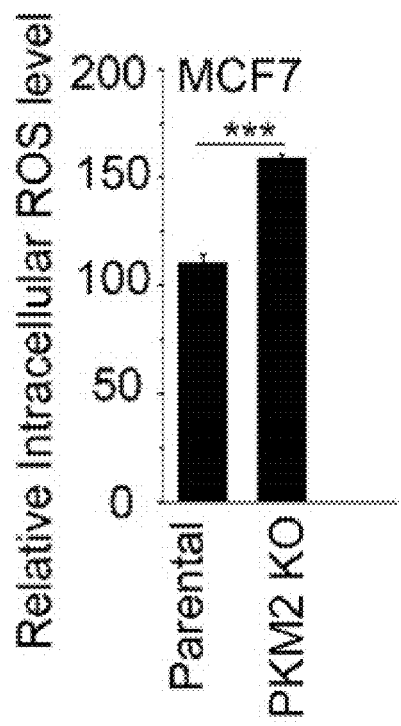
FIGS. 7A-7O show that inhibition of PKM2 methylation leads to increase of mitochondrial ROS levels.
Figure 7B:
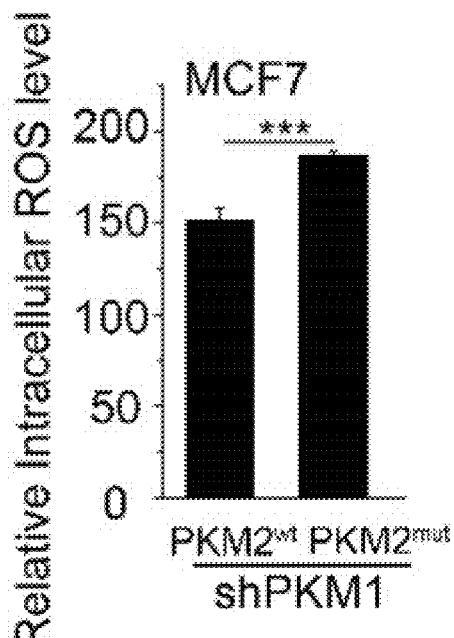
(FIG. 7B) MCF7 expressing PKM2$^{wt}$/shPKM1, and PKM2$^{mut}$/shPKM1.
Figure 7C:
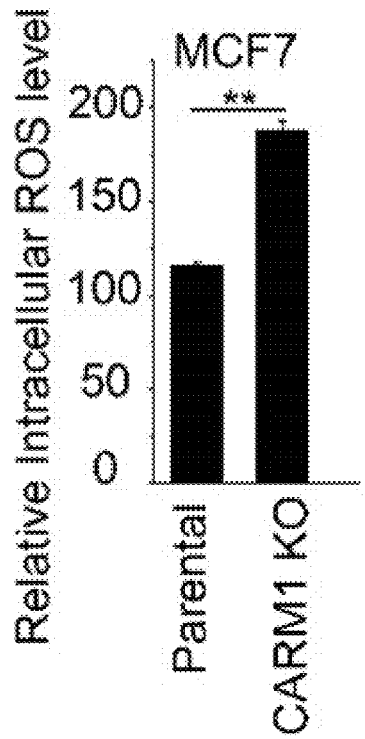
(FIG. 7C) Parental MCF7 and CARM1 KO cells.
Figure 7D:
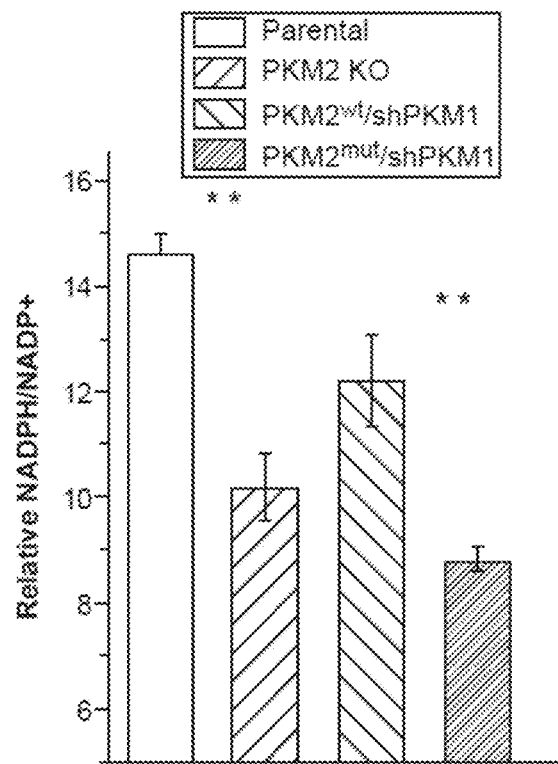
(FIGS. 7D and 7F) Relative NADPH/NADP+ ratio (FIG. 7D) and GSH concentration (FIG. 7F) in parental MCF7, PKM2 KO, PKM2$^{wt}$/shPKM1 and PKM2$^{mut}$/shPKM1 cells (n=3).
Figure 7E:
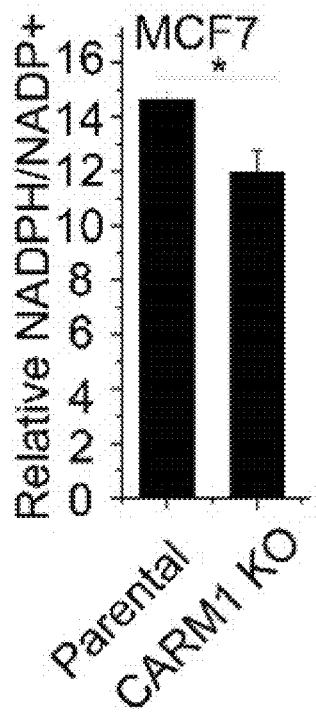
(FIGS. 7E and 7G) Relative NADPH/NADP+ ratios (FIG. 7E) and GSH concentrations (FIG. 7G) in parental MCF7 and CARM1 KO cells (n=3).
Figure 7F:
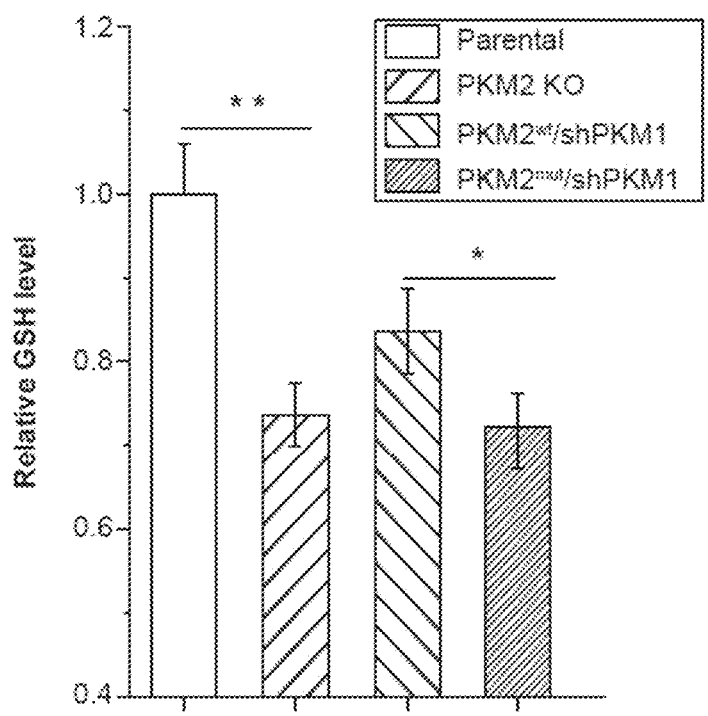
Figure 7G:
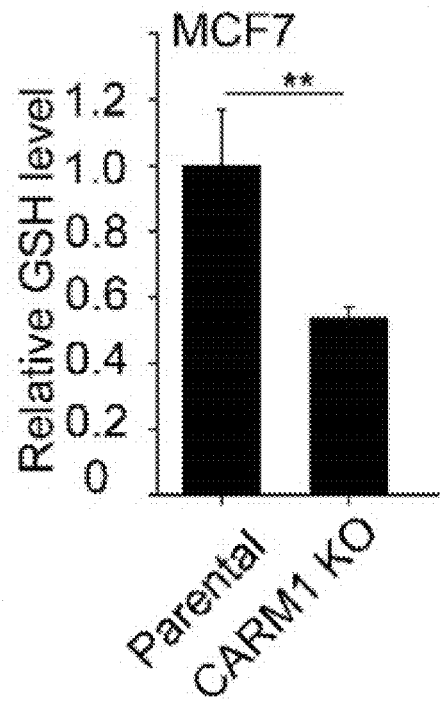
Figure 7H:
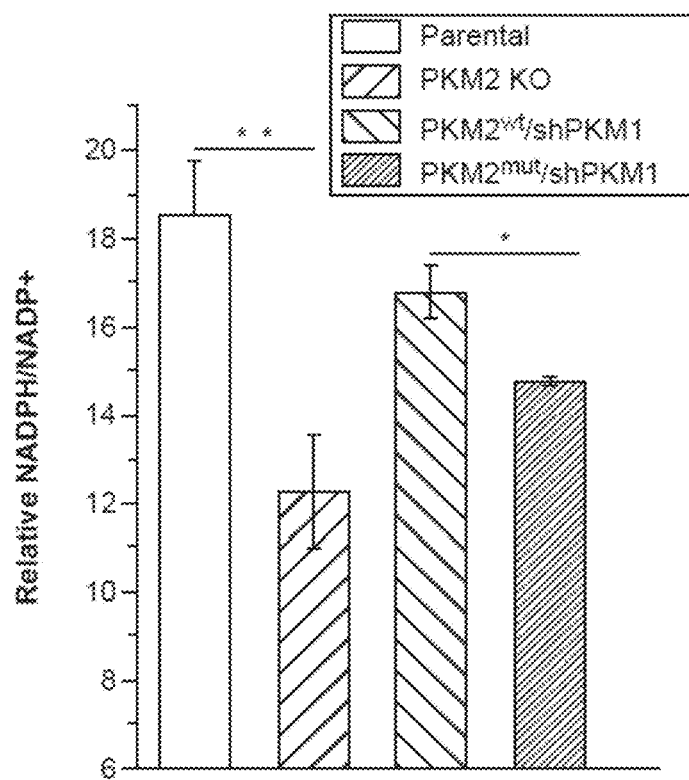
(FIGS. 7H and 7I) Relative NADPH/NADP+ ratios (FIG. 7H) and GSH concentrations (FIG. 7I) in parental MDA-MB-231, PKM2 KO, PKM2$^{wt}$/shPKM1 and PKM2$^{mut}$/shPKM1 cells (n=3) (FIGS. 7J-7L) Cell growth measured by MTT assays in MCF7 PKM2$^{mut}$/shPKM1 (FIG. 7J) or MDA-MB-231 PKM2$^{mut}$/shPKM1 (FIG. 7K) or MCF7 CARM1 KO (FIG. 7L) cells treated with mitoTEMPO.
Figure 7I:
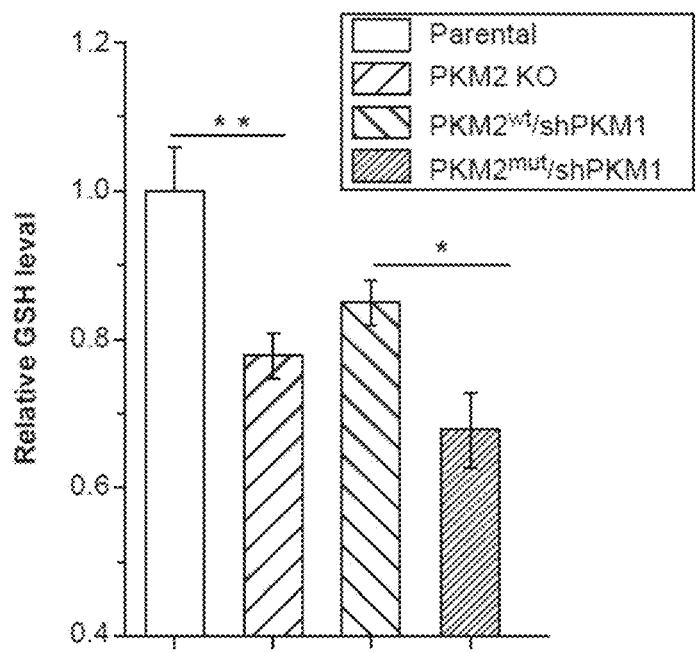
Figure 7J:
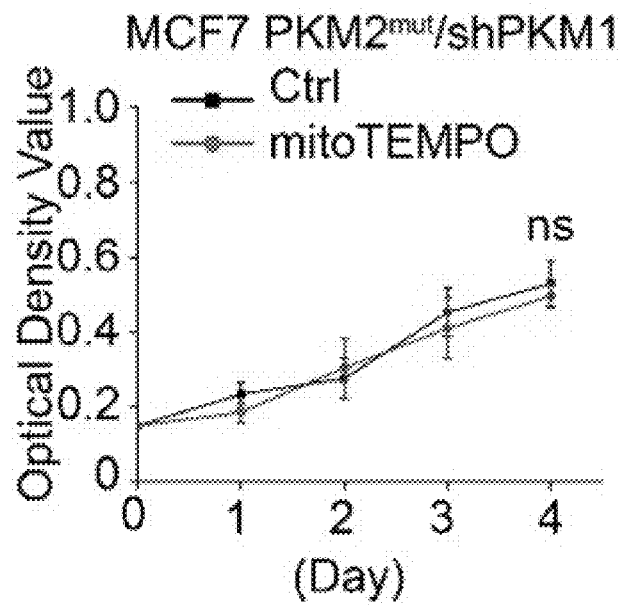
(FIG. 7M) Images of migrated MDA-MB-231 PKM2$^{mut}$/shPKM1 cells treated with mitoTEMPO.
(FIG. 7N) Cell growth in MCF7 PKM2$^{mut}$/shPKM1 or MDA-MB-231 PKM2$^{mut}$/shPKM1 or MCF7 CARM1 KO cells treated with glutathione (1 mM).
Figure 7K:
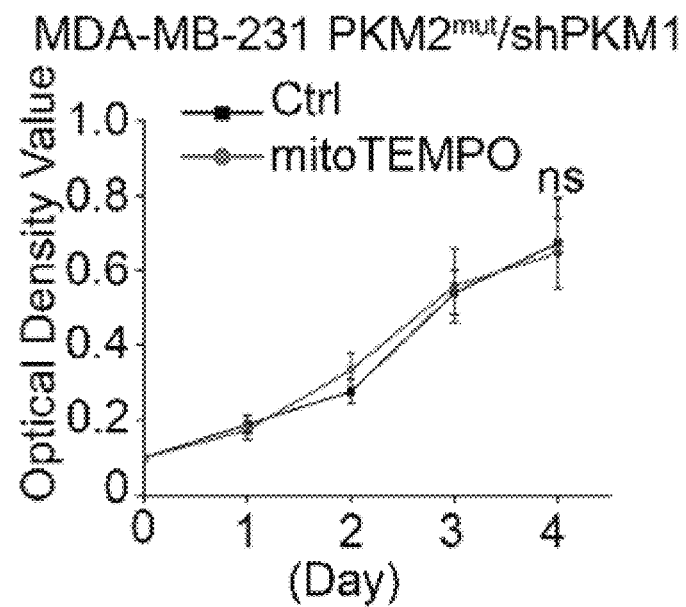
Figure 7L:
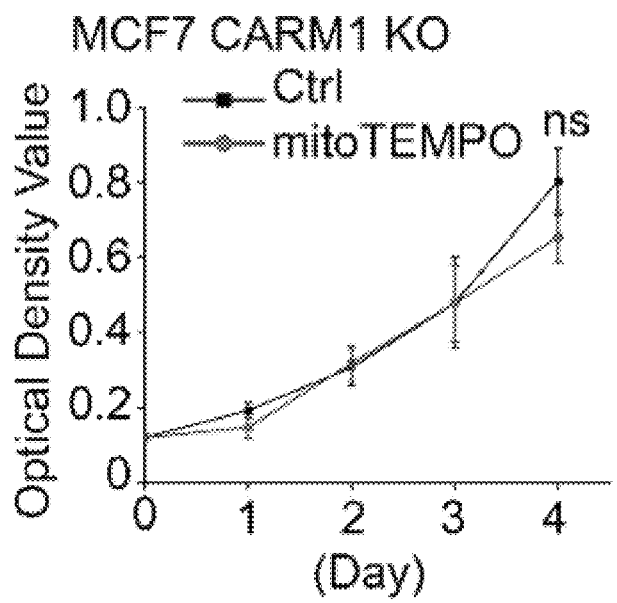
Figure 7M:
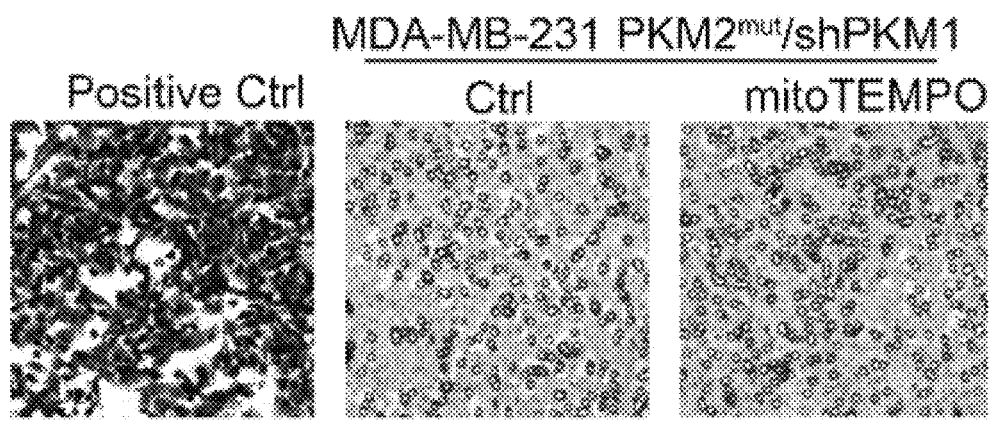
Figure 7N:
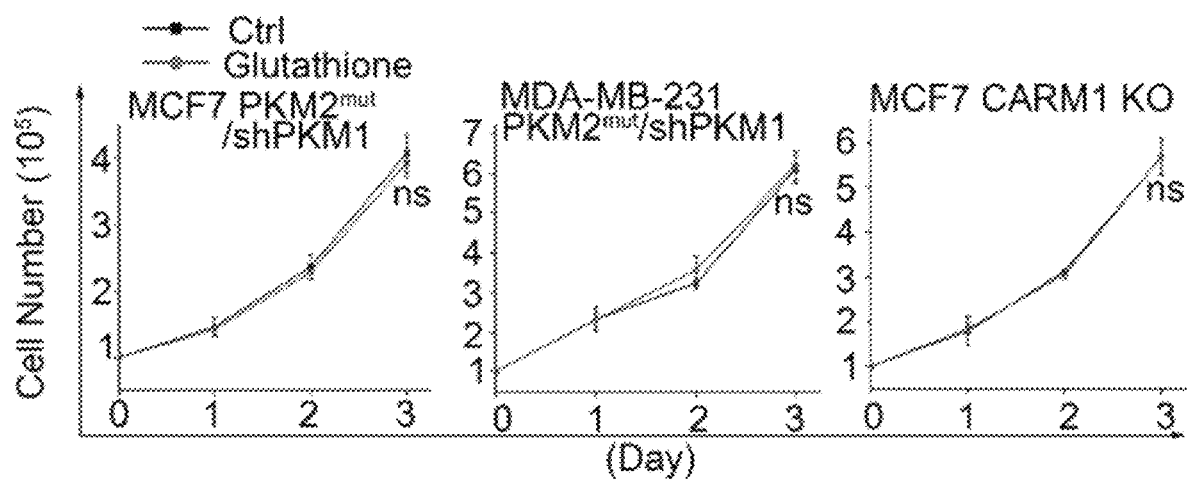
Figure 7O:
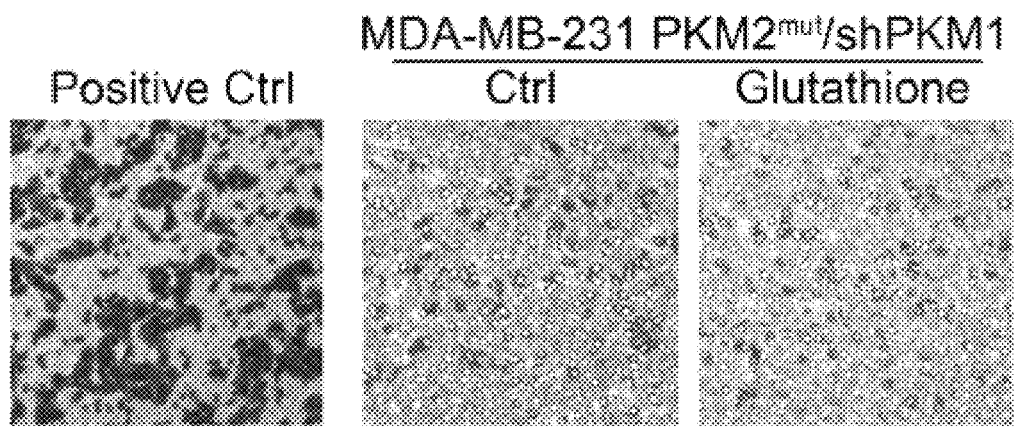

Reactive oxygen species (ROS) are produced as an inevitable byproduct of oxidative phosphorylation in mitochondria which are often scavenged by nicotinamide adenine dinucleotide phosphate (NADPH) and glutathione (GSH). Because blockage of PKM2 methylation increases oxidative phosphorylation, it was hypothesized that it would result in elevated ROS and exhaustion of NADPH and GSH. Indeed, the ROS level was elevated by knocking out PKM2 (FIG. 7A), mutating PKM2 methylation sites (FIG. 7B) or knocking out CARM1 (FIG. 7C) in MCF7 cells relative to the corresponding controls, and the increased ROS is accompanied by the decrease of NADPH/NADP+ ratio (FIGS. 7D-7E) and GSH concentration (FIG. 7F-7G). Similarly, NADPH/NADP+ ratio (FIG. 7H) and GSH concentration (FIG. 7I) were higher in parental and PKM2$^{wt}$ expressing cells than PKM2 KO and PKM2$^{mut}$ expressing MDA-MB-231 cells. However, mitTEMPO, a specific scavenger of mitochondrial superoxide, did not alter cell proliferation and migration in ROS highly producing cells (i.e., PKM2 KO, PKM2 KO expressing PKM2$^{mut}$ and CARM1 KO cells) (FIG. 7J-7M). Taken together, these results demonstrate that the glycolytic metabolism and growth effects regulated by PKM2 methylation are largely independent of ROS production.

Figure 8A:
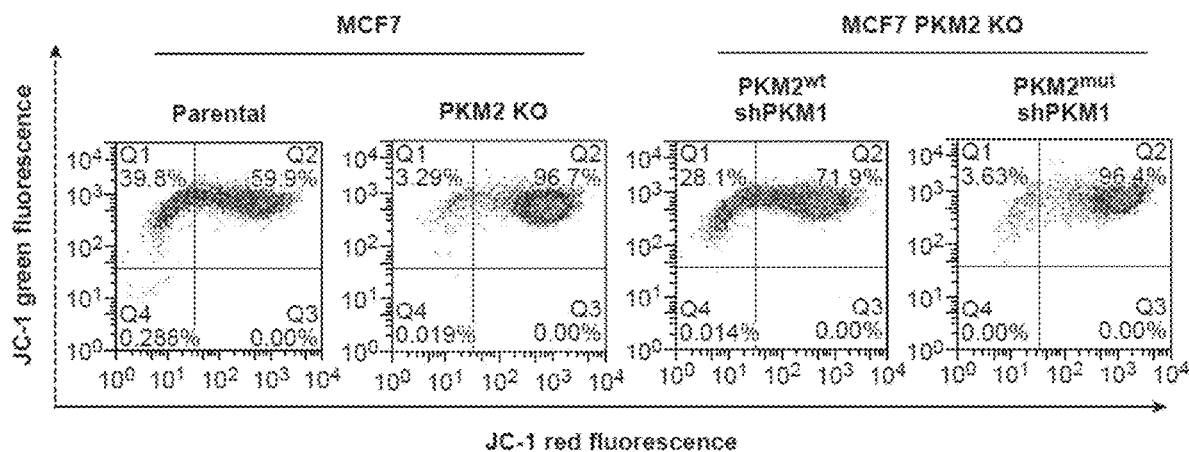
FIGS. 8A-8Q show the inhibition of PKM2 methylation increases mitochondrial membrane potential and [Ca$^{2+}$]$_{mito}$.
Figure 8B:
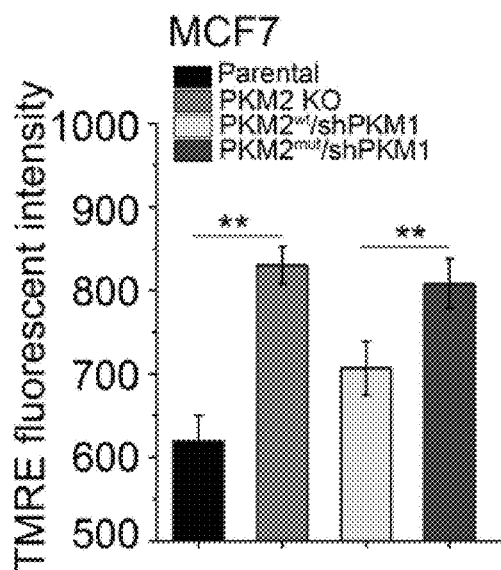
Figure 8C:
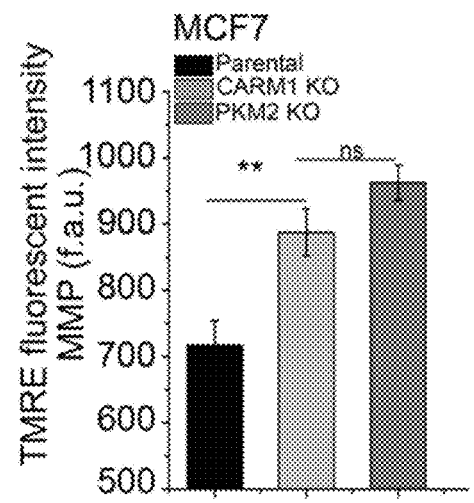
Figure 9A:
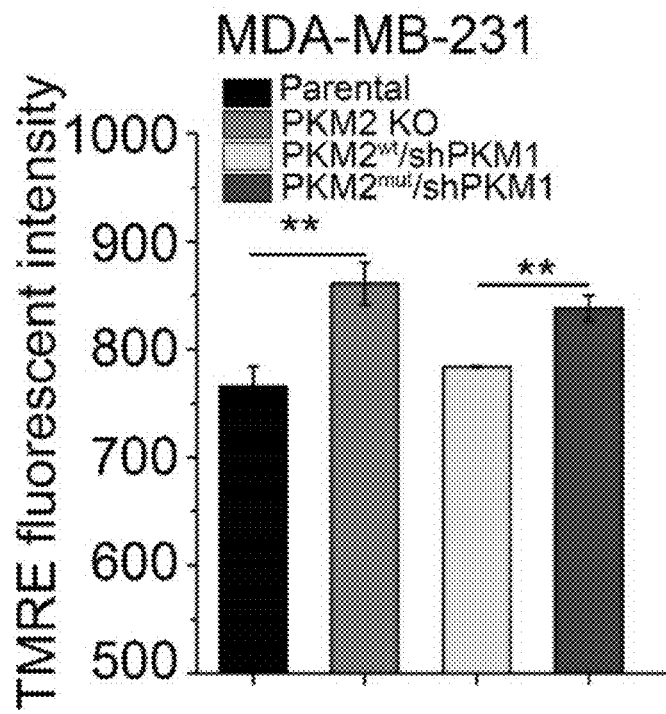
FIGS. 9A-9F show that PKM2 methylation suppresses mitochondrial membrane potential and mitochondrial DNA content.
Figure 9B:
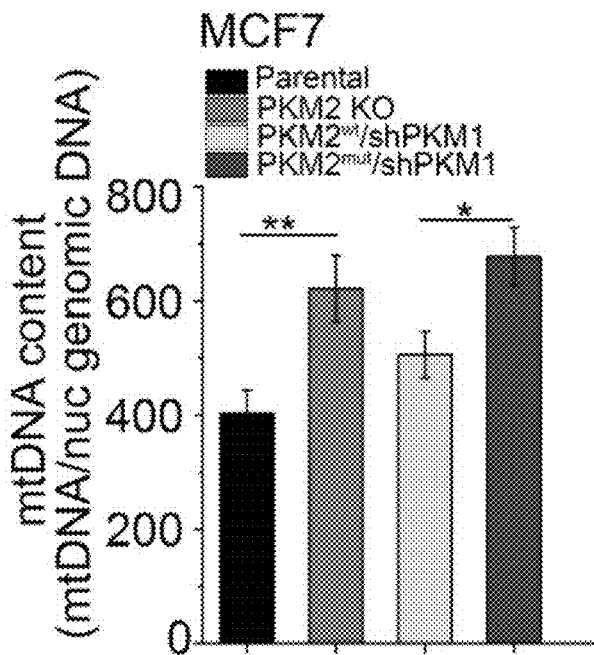
Figure 9C:
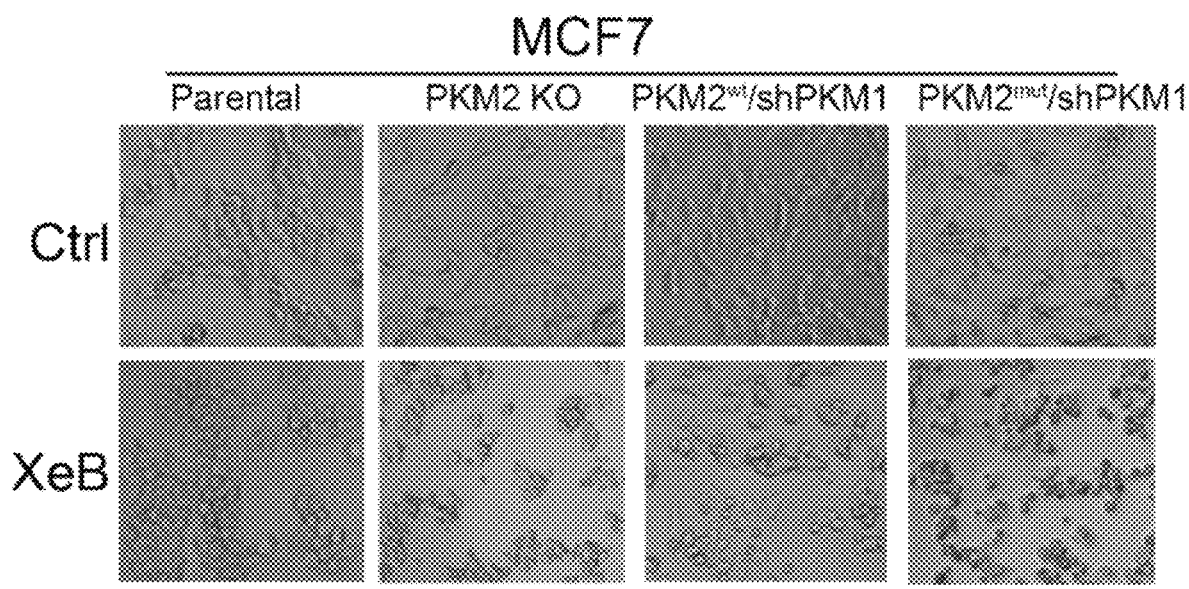
Figure 9D:
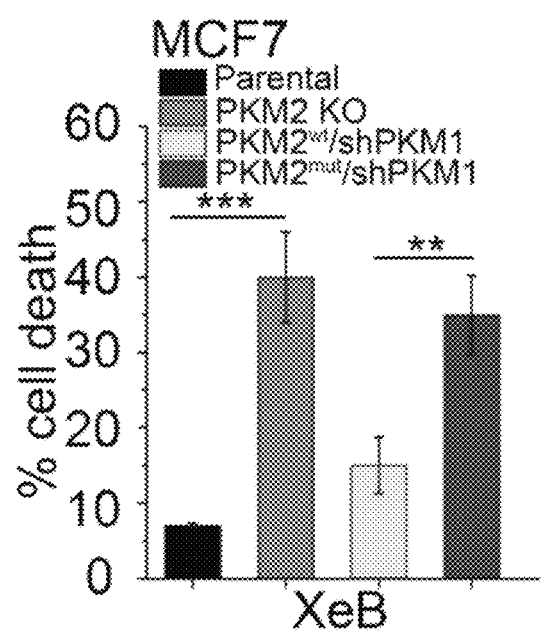
Figure 9E:
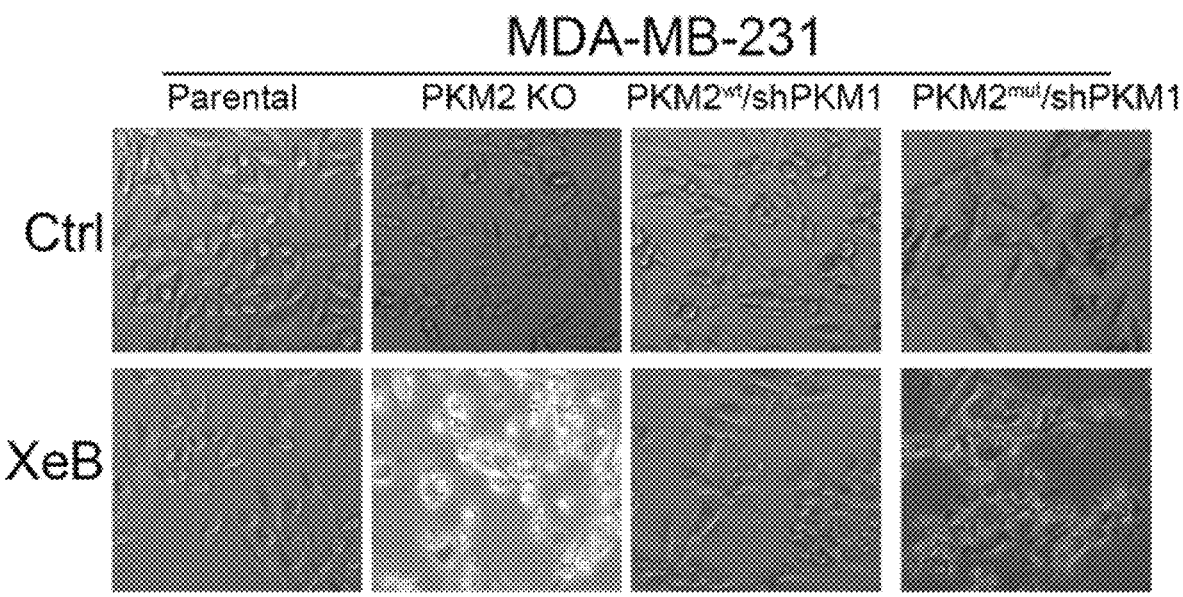
Figure 9F:
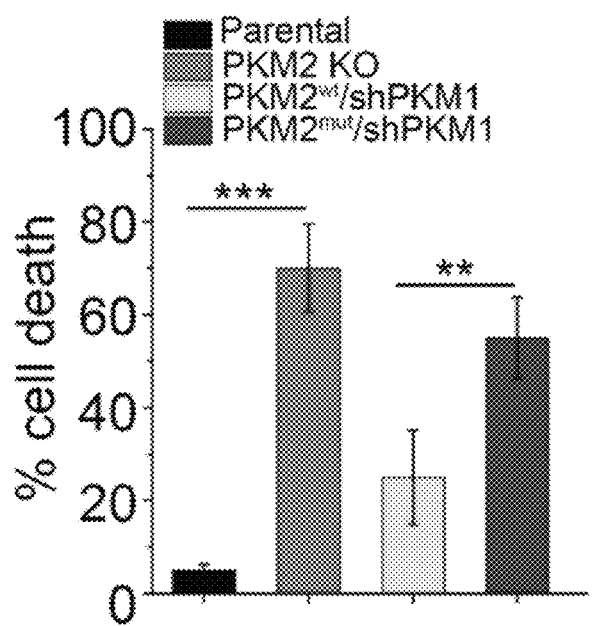

Example 6: Inhibiting PKM2 Methylation Increases Ca$^{2+}$ Uptake and Mitochondrial Membrane Potential To investigate the mechanism by which the mitochondrial respiration was elevated in PKM2 methylation defective cells as compared with the PKM2 methylation competent cells, the effects of PKM2 methylation on parameters indicative of mitochondrial functions were evaluated. Mitochondrial membrane potential ($\Delta\Psi_m$), was measured as an indicator of oxidative energy metabolism, by incorporation of mitochondria specific JC-1 dye followed by flow cytometry. The results showed that $\Delta\Psi_m$ increased by knocking out PKM2 in MCF7 cells and restoration of PKM2$^{wt}$, but not PKM2$^{mut}$, in PKM2 KO cells abrogated the increase of $\Delta\Psi_m$ (FIG. 8A). To validate this finding, tetramethylrhodamine ethyl ester (TMRE), another cell-permeable, red-orange fluorescent dye that is readily sequestered by active mitochondria, was used to measure the $\Delta\Psi_m$. Similar results were obtained in both MCF7 (FIG. 8B) and MDA-MB-231 cells (FIG. 9A). In accordance with the PKM2 methylation-dependent $\Delta\Psi_m$ change, CARM1 KO also increased $\Delta\Psi_m$ in MCF7 cells (FIG. 8C). Mitochondrial DNA copy number is another indicator of mitochondrial activity and the higher copy number corresponds to the higher activity. Moreover, loss of PKM2 expression or PKM2 methylation resulted in elevated mitochondrial DNA content in MCF7 cells (FIG. 9B). Therefore, PKM2 methylation suppresses mitochondrial function and loss of PKM2 methylation releases the suppressive effect and results in elevated $\Delta\Psi_m$.

Figure 8D:
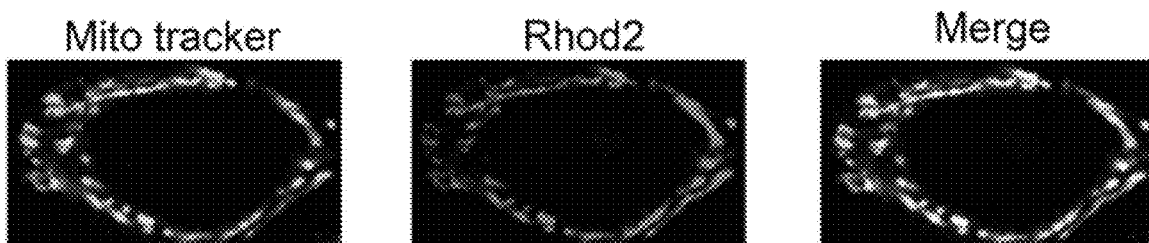
(FIG. 8D) Representative images of co-localized mitochondrial tracker and Rhod-2 in MCF7 PKM2 KO cells.
Figure 8E:
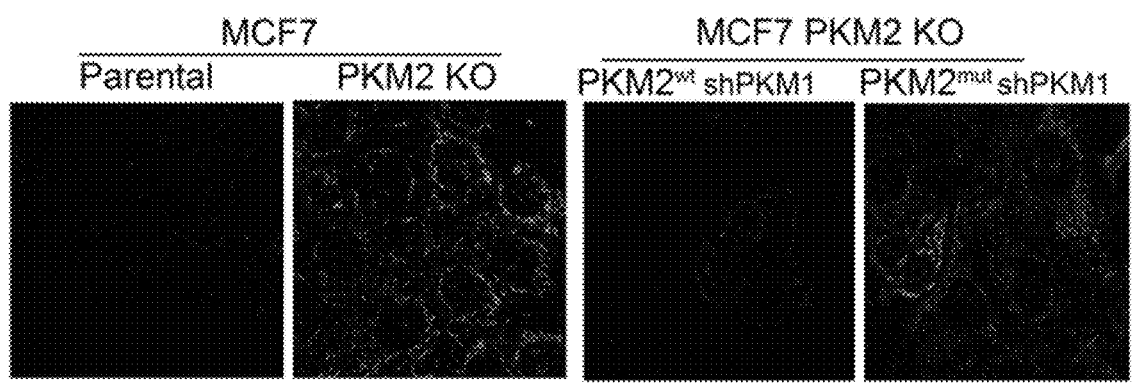
(FIG. 8E) Representative images of Rhod-2-labeled mitochondria in parental MCF7, PKM2 KO, PKM2$^{wt}$/shPKM1 and PKM2$^{mut}$/shPKM1 cells.
Figure 8F:
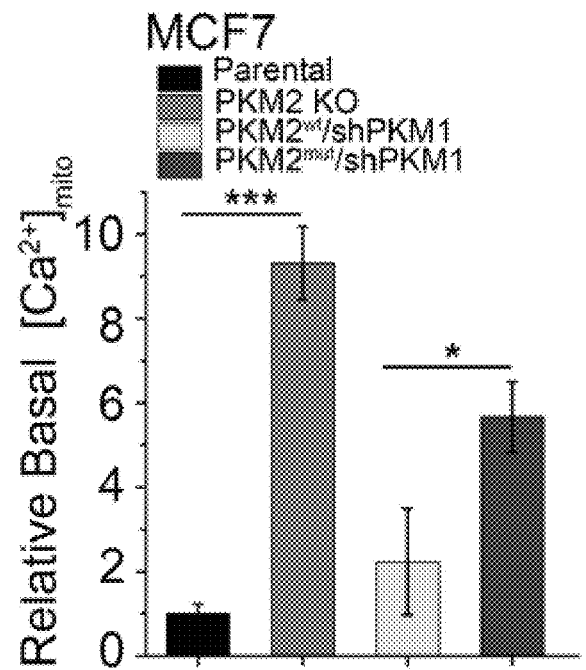
(FIGS. 8F-8I) Relative basal [Ca$^{2+}$]$_{mito}$ in Rhod-2-labeled parental, PKM2 KO, PKM2$^{wt}$/shPKM1 and PKM2$^{mut}$/shPKM1 MCF7 (FIG. 8F) (n=3) or corresponding MDA-MB-231 cells (FIG. 8G) (n=3); or parental MEF and PKM2 KO cells (FIG. 8H) (n=3); or parental MCF7, CARM1 KO and PKM2 KO cells (FIG. 8I) (n=3).
Figure 8G:
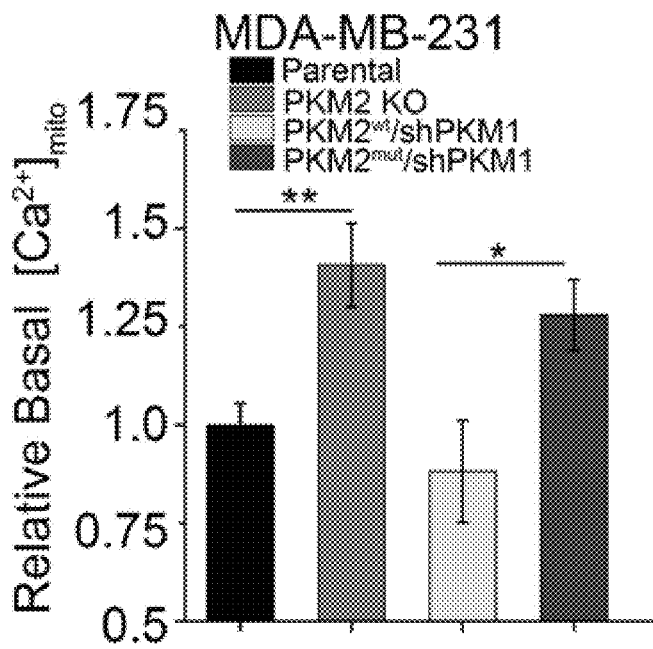
Figure 8H:
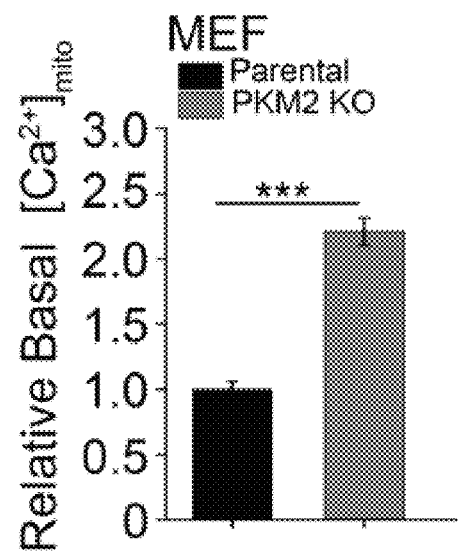
Figure 8I:
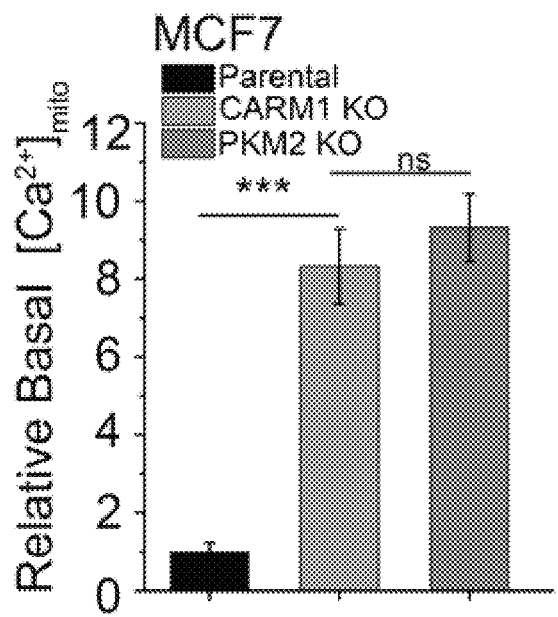
Figure 8J:
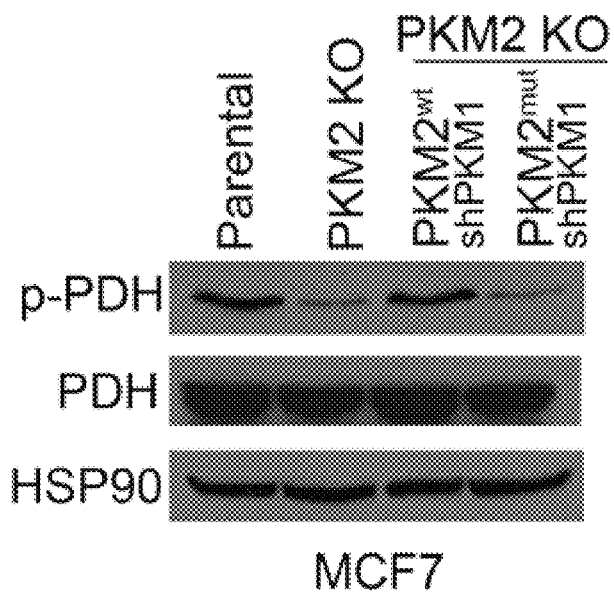
(FIGS. 8J-8M) Western blot analyses of phosphorylated PDH and total PDH in indicated MCF7 (FIG. 8J) or corresponding MDA-MB-231 cells (FIG. 8K); or parental MEF and PKM2 KO (1); or parental MCF7, CARM1 KO and PKM2 KO cells (FIG. 8M). (FIGS.
Figure 8K:
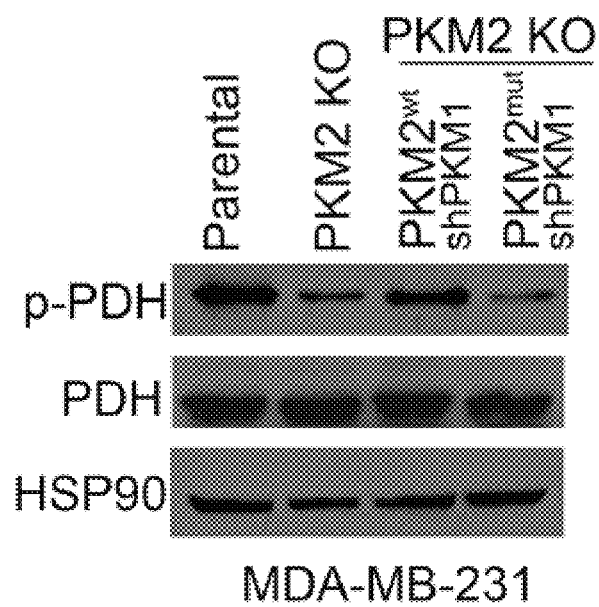
Figure 8L:
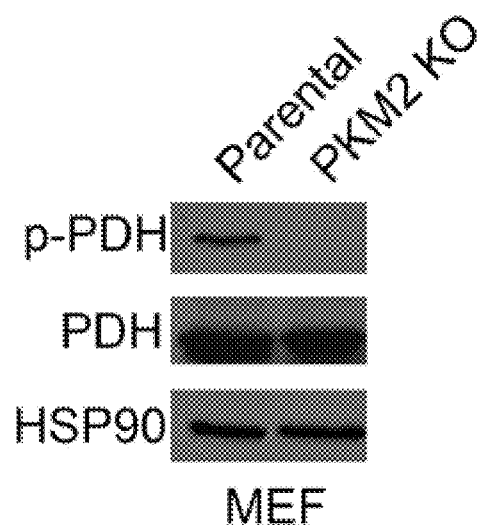
Figure 8M:
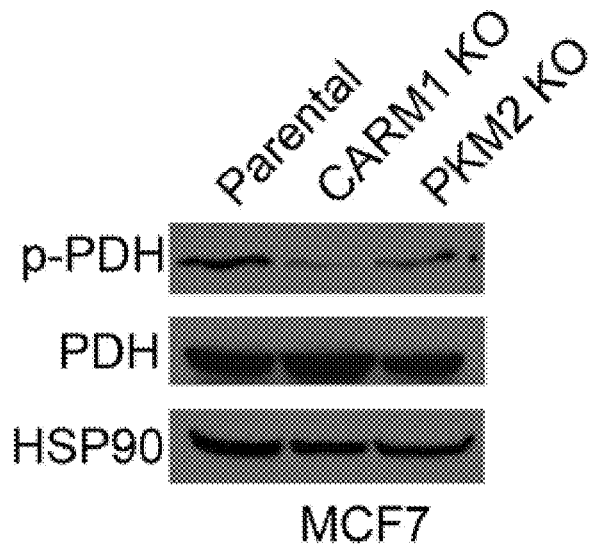
Figure 8N:
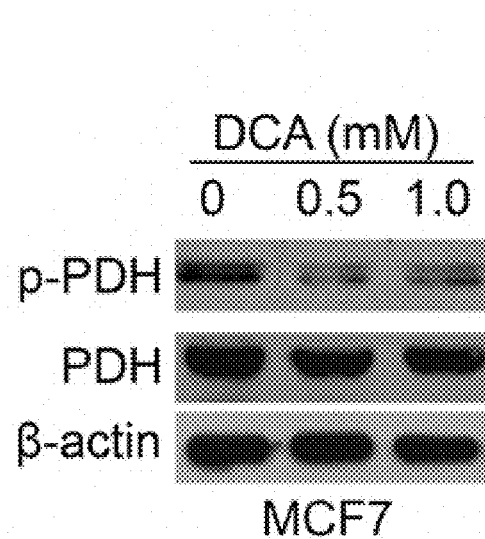
Figure 8O:
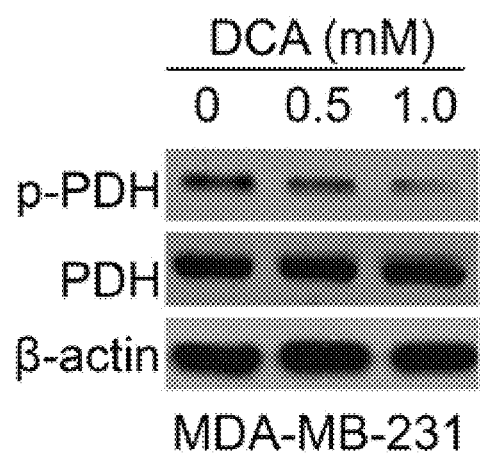
Figure 8P:
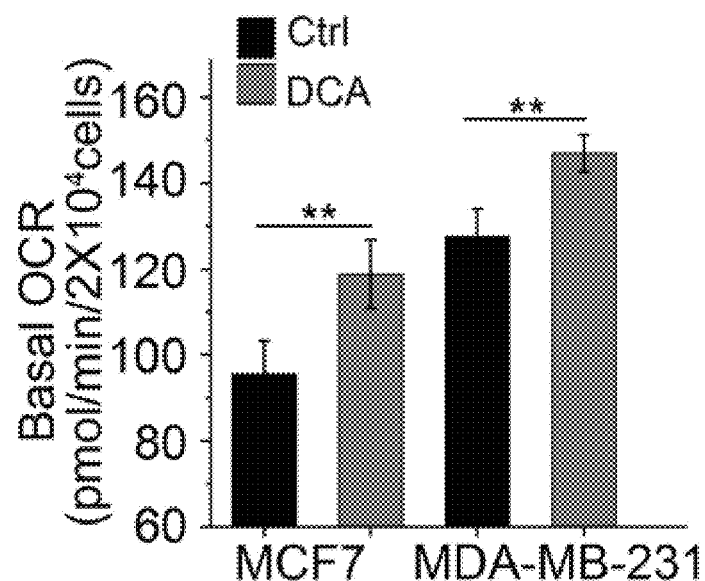
Figure 8Q:
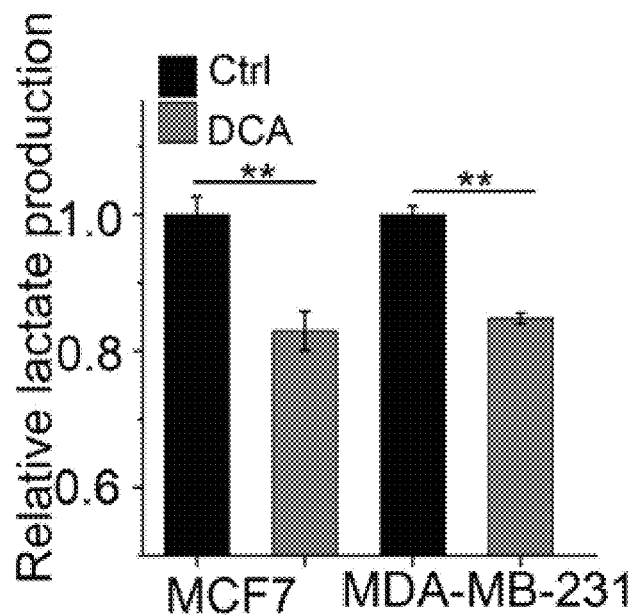

Mitochondrial Ca$^{2+}$ primarily driven by $\Delta\Psi_m$ is known to stimulate oxidative phosphorylation for maintenance of cellular energy homeostasis. The sensitivity of $\Delta\Psi_m$ to PKM2 methylation status prompted experiments to assess the basal mitochondrial Ca$^{2+}$ concentration ([Ca$^{2+}$]$_{mito}$) using a Ca$^{2+}$-sensitive Rhod-2 AM dye followed by confocal imaging (FIG. 8D). The results showed that PKM2 KO profoundly increased basal [Ca$^{2+}$]$_{mito}$ in MCF7 (FIGS. 8E-8F) and MDA-MB-231 (FIG. 8G), and the effect is not cancer-cell specific as [Ca$^{2+}$]$_{mito}$ was also increased in PKM2 KO MEF cells (PKM2$^{fl/fl}$, Cre-estrogen receptor) (FIG. 8H). Restoration of PKM2$^{wt}$, but not PKM2$^{mut}$, abrogated the elevated basal [Ca$^{2+}$]$_{mito}$ caused by PKM2 KO in MCF7 and MDA-MB-231 cells (FIGS. 8F-8G), suggesting that the methylated PKM2 suppresses mitochondrial Ca$^{2+}$ uptake. In accordance with this finding, basal [Ca$^{2+}$]$_{mito}$ was also elevated in CARM1 KO MCF7 cells (FIG. 8I). To assess the importance of calcium hemostasis and oxidative phosphorylation to cell survival in PKM2 KO or methylation defective cells, cells were treated with Xestospongin B (XeB), a specific IP3Rs inhibitor, to inhibit IP3Rs-mediated Ca$^{2+}$ release from ER stores. The results showed that PKM2 KO or PKM2$^{mut}$ cells are more vulnerable to XeB than parental and PKM2$^{wt}$ cells (FIGS. 9C-9F), indicating that addiction to oxidative phosphorylation upon loss of PKM2 methylation plays essential roles in cell survival. Mitochondrial matrix calcium regulates oxidative phosphorylation through activating several dehydrogenases, including pyruvate dehydrogenase (PDH) that couples glycolysis to the tricarboxylic acid (TCA) cycle by irreversible decarboxylation of pyruvate. Phosphorylation of PDH by PDH kinase suppresses its activity, whereas dephosphorylation by Ca$^{2+}$-dependent pyruvate phosphatase enhances its activity. To investigate if fluctuated [Ca$^{2+}$]$_{mito}$ levels cause changes of PDH activity, phosphorylated PDH levels were measured in PKM2 KO, CARM1 KO and PKM2$^{wt}$ or PKM2$^{mut}$ restored cell lines by Western blot. The results showed that PKM2 KO dramatically decreased PDH phosphorylation in MCF7 (FIG. 8J), MDA-MB-231 (FIG. 8K) and MEFs (FIG. 8I) cells, indicative of the increased PDH activity by [Ca$^{2+}$]$_{mito}$ influx. Restoration of PKM2$^{wt}$, but not PKM2$^{mut}$, increased phosphorylated PDH in MCF7 and MDA-MB-231 cells (FIGS. 8J-8K), indicative of the attenuated PDH activity. On the contrary, CARM1 KO resulted in decreased PDH phosphorylation in MCF7 cells resembling that of PKM2 KO (FIG. 8M). As expected, treatment of cells with dichloroacetate (DCA), a pyruvate dehydrogenase kinases (PDKs) inhibitor, also decrease PDH phosphorylation and lactate production while increasing oxidative phosphorylation (FIGS. 8N-8Q). Collectively, these results demonstrated that PKM2 methylation plays a role in restraining mitochondrial oxidative phosphorylation via decreasing mitochondrial $\Delta\Psi_m$ and $Ca^{2+}$ uptake, and increasing PDH phosphorylation.

Figure 10A:
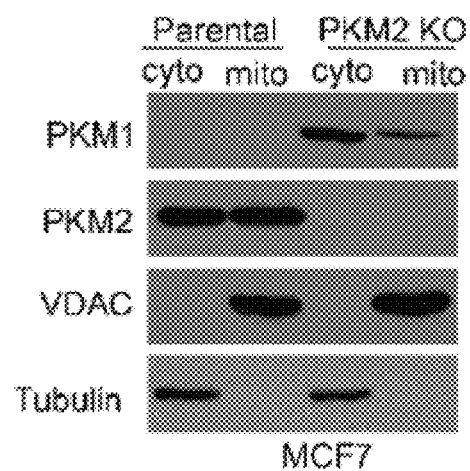
FIGS. 10A-10N show that MAM localized PKM2 interacts with and suppresses IP3Rs expression in a methylation-dependent manner.
Figure 10B:
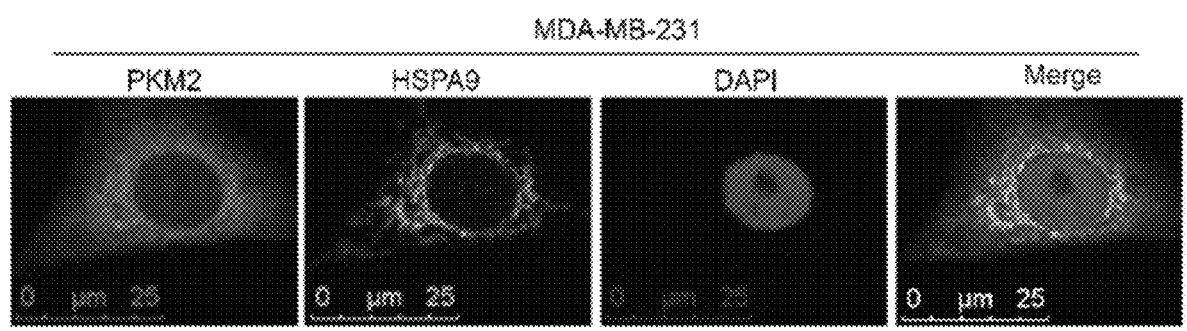
(FIG. 10B) Confocal images of PKM2 localization on mitochondria. HSPA9 serves as a positive control which largely overlap with PKM2 staining.
Figures 10C, 10D:
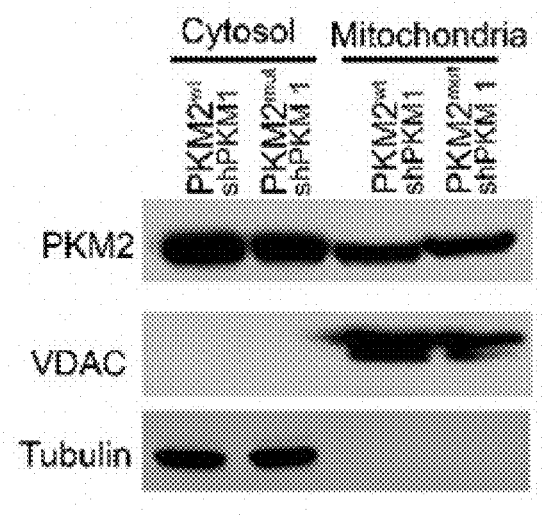
(FIG. 10C) Western blot analyses of wild type or mutant PKM2 in cytosolic and mitochondria fractions from MCF7 PKM2$^{wt}$/shPKM1 and PKM2$^{mut}$/shPKM1 cells.
(FIG. 10D) List of selected ER and mitochondrial proteins that interact with wild type PKM2 or methylation-defective PKM2. Flag-tagged wild type or mutant PKM2 were transiently transfected into HEK293T cells. Flag-tagged PKM2 was pulled down from cell lysates and the interacting proteins were analyzed by mass spectrometry. The numbers of the detected peptides for each protein are indicated.
Figure 10E:
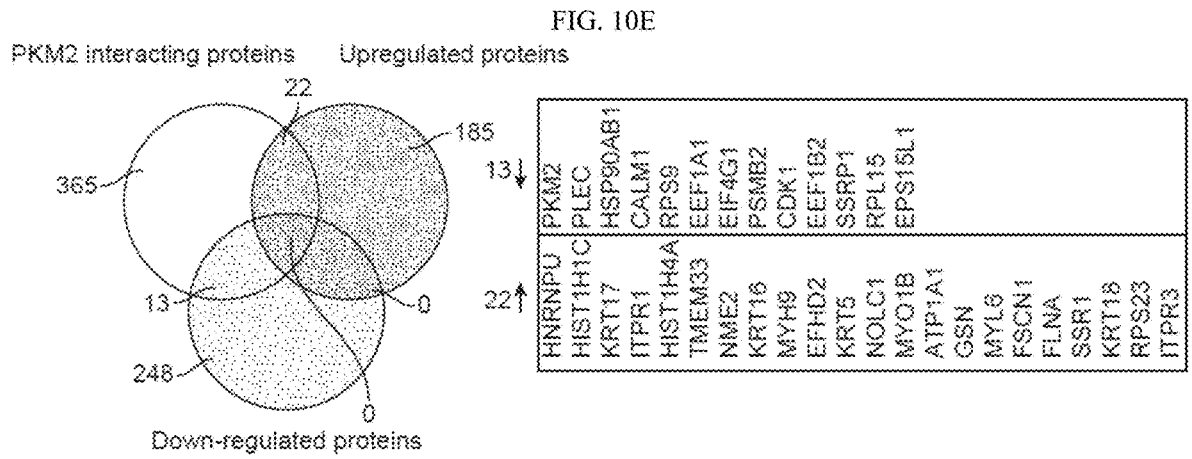
(FIG. 10E) Venn diagram of PKM2 interacting proteins identified in FIG. 10D overlapped with the altered proteins in response to PKM2 KO in MCF7 cells (FIG. 6C). 22 PKM2 interacting proteins were upregulated and 13 PKM2 interacting proteins were downregulated. ITPRs are also known as IP3Rs.
Figure 10F:
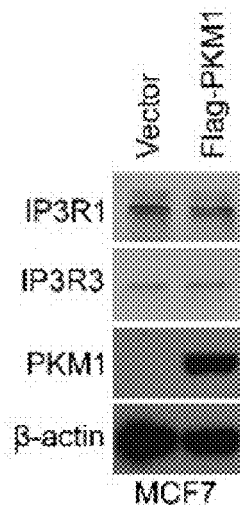
(FIG. 10F) Western blot analysis of IP3R1 and IP3R3 in MCF7 cells overexpressing Flag-PKM1.
Figure 10G:
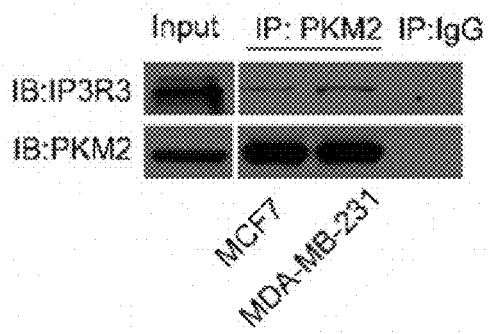
(FIG. 10G) Co-immunoprecipitation of IP3R3 with PKM2 from MCF7 and MDA-MB-231 cell lysates.
Figure 11A:
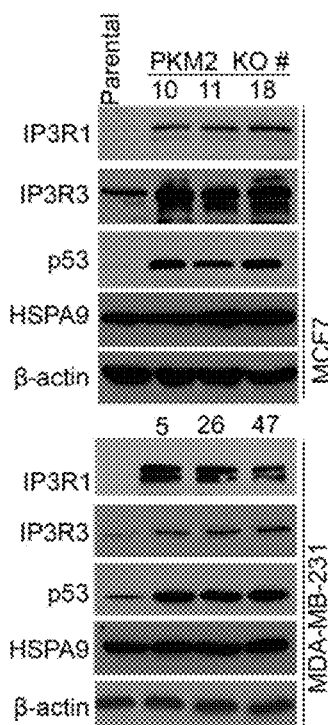
FIGS. 11A-11N show methylated PKM2 restrains mitochondrial Ca$^{2+}$ uptake through interacting with and suppressing IP3Rs expression.
Figure 11B:
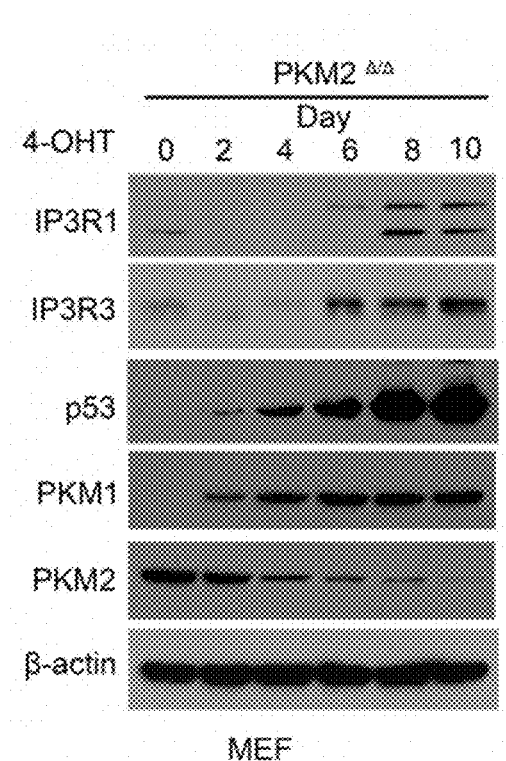
(FIG. 11B) Western blot analysis of IP3R1, IP3R3, p53, PKM1 and PKM2 in MEF (PKM2$^{fl/fl}$, Cre-ER) cells treated with 4-OHT for the indicated time.
Figure 11C:
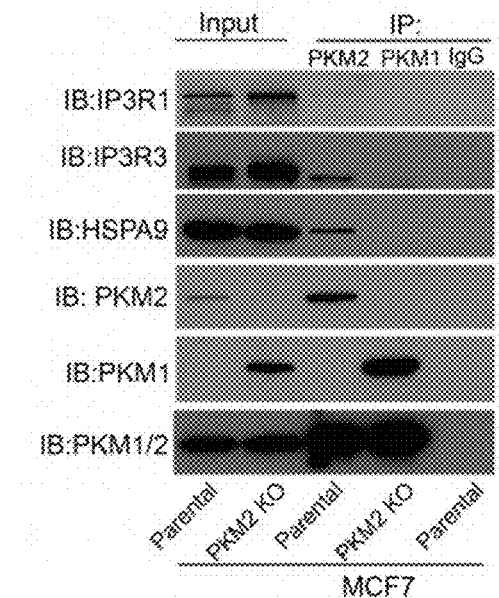
(FIG. 11C) Co-immunoprecipitation of IP3Rs and HSPA9 with PKM2 but not PKM1. Flag-tagged PKM1 or PKM2 are immunoprecipitated from cell lysates derived from parental MCF7 or PKM2 KO cells using α-Flag antibody followed by detection of PKM1, PKM2, IP3R1, IP3R3 and HSPA9 by Western blot.
Figure 11D:
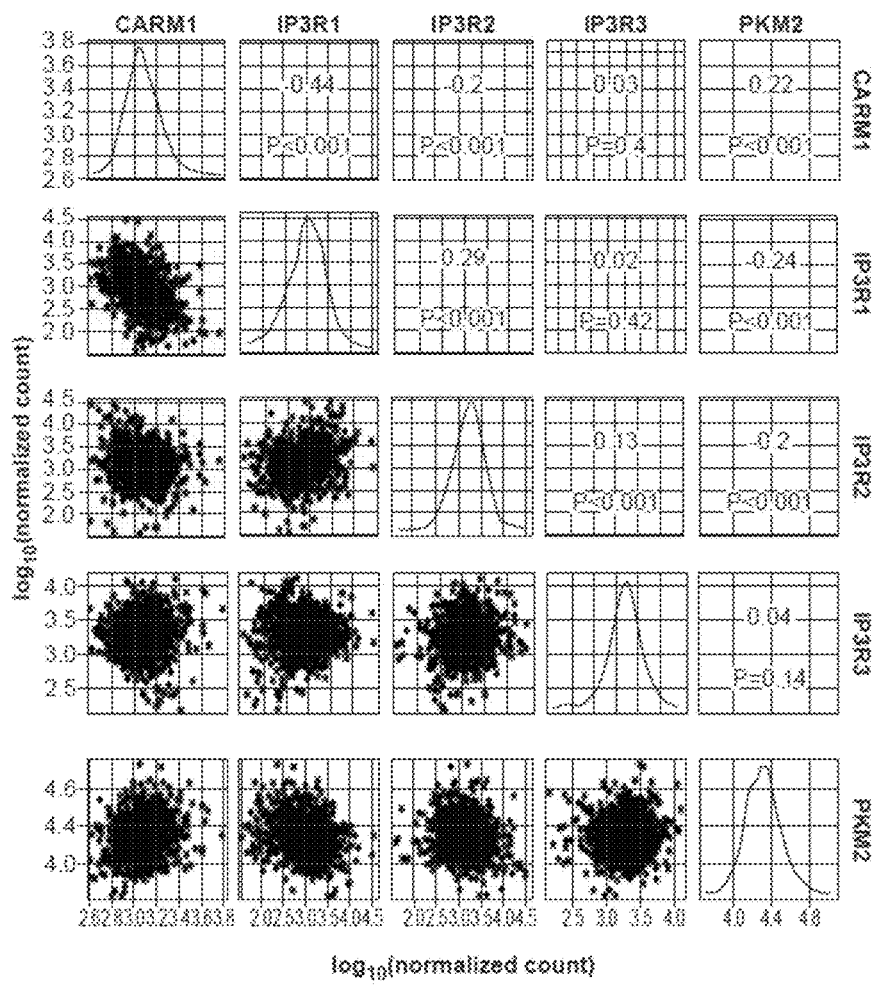
(FIG. 11D) mRNA correlation of CARM1, IP3R1, IP3R2, IP3R3 and PKM2 in 1093 primary breast tumor samples of TCGA.
Figure 11E:
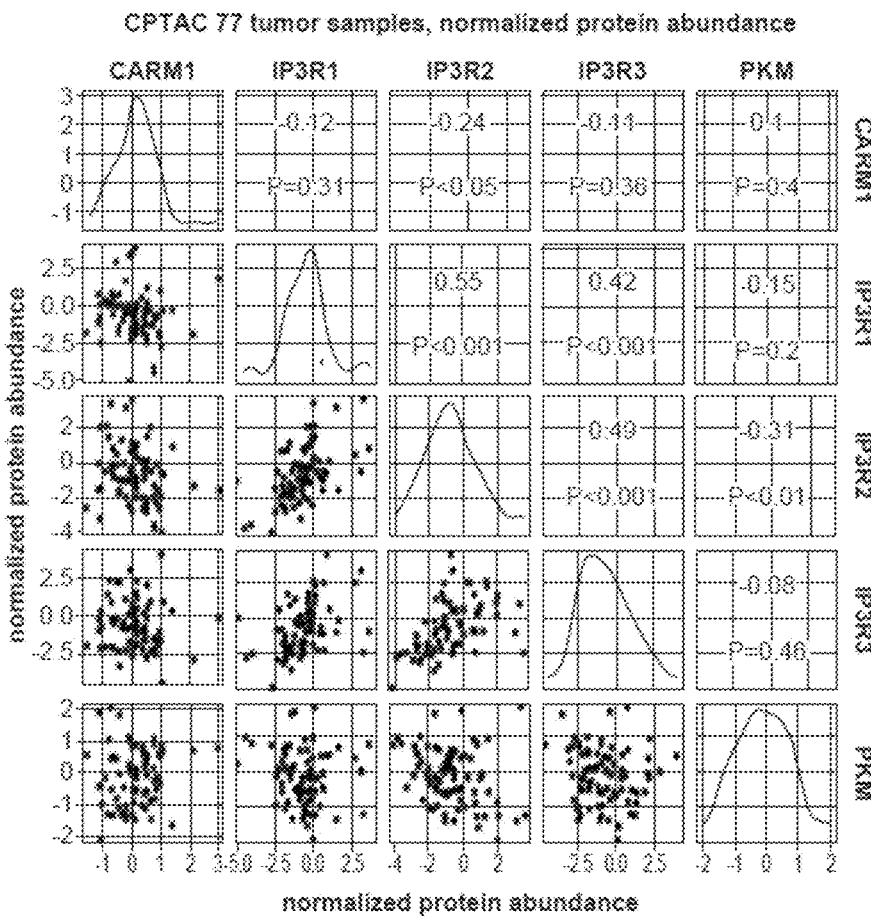
(FIG. 11E) Protein correlation of CARM1, IP3R1, IP3R2, IP3R3 and PKM in 77 breast tumor samples of CPTAC collection.

Example 7: Methylated PKM2 Restrains Mitochondrial $Ca^{2+}$ Uptake Through Interacting with and Suppressing IP3Rs Expression A previous study reported detection of PKM2 protein in mitochondria. The presence of PKM2 in the mitochondrial fraction was confirmed by subcellular fractionation (FIG. 10A) and a portion of PKM2 co-localizing with HSPA9 in mitochondrial outer membrane was observed (FIG. 10B). However, the mitochondrial localization of PKM2 appeared not to be affected by its methylation status (FIG. 10C). To elucidate the molecular mechanism by which methylated PKM2 modulates mitochondrial oxidative phosphorylation, Flag-tagged PKM2$^{wt}$ or PKM2$^{mut}$ was overexpressed in HEK293T cells, and then MS analyses on Flag-PKM2 co-immunoprecipitated proteins was performed to identify the differentially interacted proteins. A large number of the interacting proteins were identical between PKM2$^{wt}$ and PKM2$^{mut}$ (not shown); however, ER calcium releasing proteins IP3R1, 2, 3 showed the most notable difference between PKM2$^{wt}$ and PKM2$^{mut}$ (FIG. 10D). Interestingly, IP3R1 and IP3R3 are not only putative PKM2-interacting protein, but also their expression levels increased in PKM2 KO MCF7 cells (FIG. 6C and FIG. 10E). To confirm the proteomics results, the IP3R1 and IP3R3 expression levels were detected by Western blotting in different PKM2 KO clones derived from MCF7 and MDA-MB-231 cells. As shown in FIG. 11A, both IP3R1 and IP3R3 were significantly elevated in three different PKM2 KO clones in both cell lines. As a negative control, the protein level of HSPA9, another PKM2-interacting protein, was insensitive to PKM2 KO. To discern that increase of IP3Rs does not result from the increase of PKM1 protein in PKM2 KO cells, the kinetics of protein changes in the immortalized, tamoxifen-inducible PKM2 KO MEF (PKM2$^{fl/fl}$, Cre-estrogen receptor) cells were measured. Consistent with a previous report, PKM1 expression is elevated after a two-day 4-hydroxytamoxifen (4-OHT) treatment and reached plateau after four-day treatment (FIG. 11B). However, the increased expression of IP3R1 and IP3R3 was detected at later, and not earlier, time points when PKM2 level was substantially declined (FIG. 11B). Moreover, overexpression of PKM1 failed to increase IP3Rs expression (FIG. 10F), reinforcing that IP3Rs are regulated by PKM2 not PKM1. Co-immunoprecipitation showed that, PKM2, but not PKM1, interacted with the endogenous IP3R1 and IP3R3 in breast cancer cells (FIG. 11C and FIG. 10G). These data imply that the elevated IP3Rs in PKM2 KO cells is likely the consequence of loss of PKM2 rather than gain of PKM1. The reversed expression of IP3Rs with PKM2 was also observed in The Cancer Genome Atlas (TCGA) breast tumor specimens. By analyzing the transcript levels of CARM1, PKM2, and IP3Rs in 1093 primary breast tumors in TCGA, a positive correlation was observed between CARM1 and PKM2. However, both negatively correlated with IP3R1 and IP3R2 expression (FIG. 11D). Similar observation was made at the protein levels in the CPTAC 77 breast tumor proteogenomics database, where all IP3Rs protein levels were negatively correlated with CARM1 or PKM (FIG. 11E).

Figure 10H:
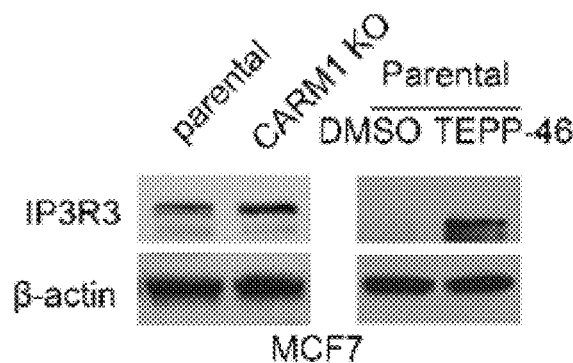
(FIG. 10H) Western blot analyses of IP3R3 protein levels in parental MCF7, CARM1 KO, or parental MCF7 treated with DMSO or TEPP-46.
Figure 10I:
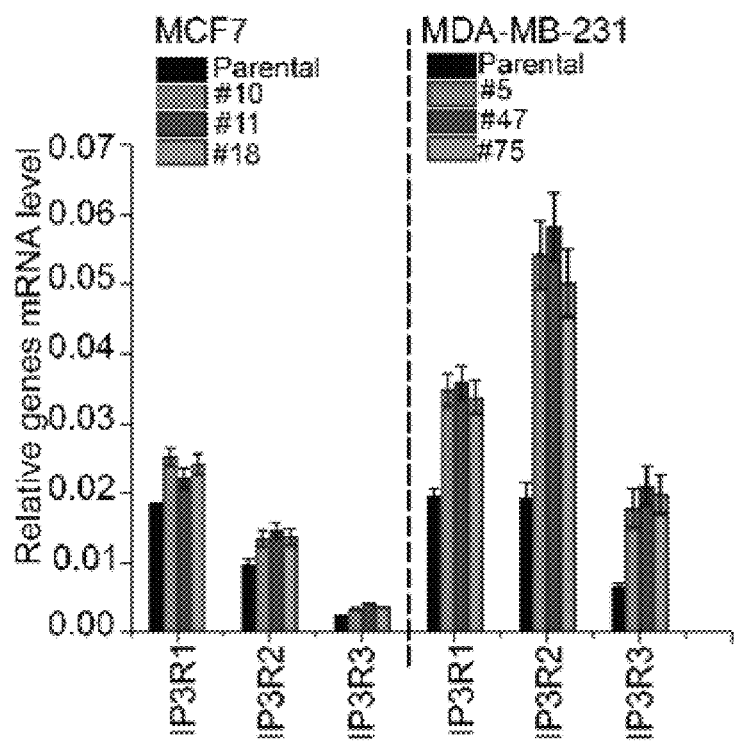
(FIG. 10I) Q-PCR analyses of mRNA levels of IP3R1, IP3R2 and IP3R3 in parental MCF7 and MDA-MB-231 cells and their respective PKM2 KO clones (n=3).
Figure 10J:
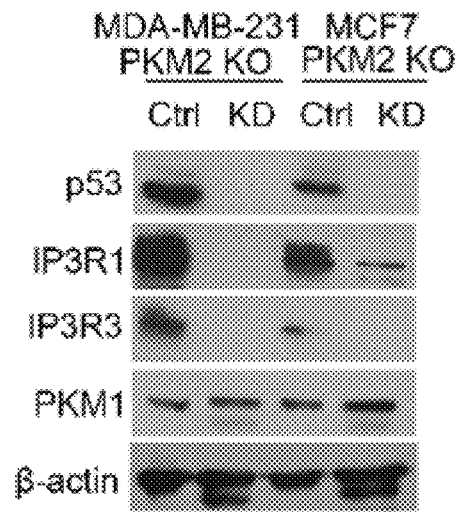
(FIG. 10J) Western blot analyses of p53, IP3R1, IP3R3 and PKM1 in MCF7 PKM2 KO and MDA-MB-231 PKM2 KO cells expressing control shRNA and p53 shRNA.
Figure 10K:
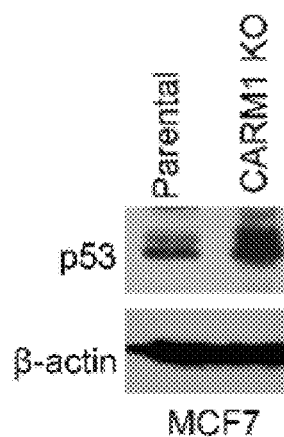
(FIG. 10K) Western blot analyses of p53 in parental MCF7 and CARM1 KO cells.
Figure 10L:
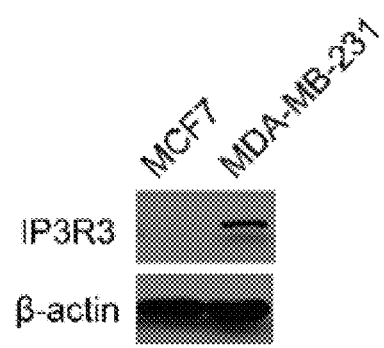
(FIG. 10L) Western blot analysis of relative IP3R3 in MCF7 and MDA-MB-231 cells.
Figure 10M:
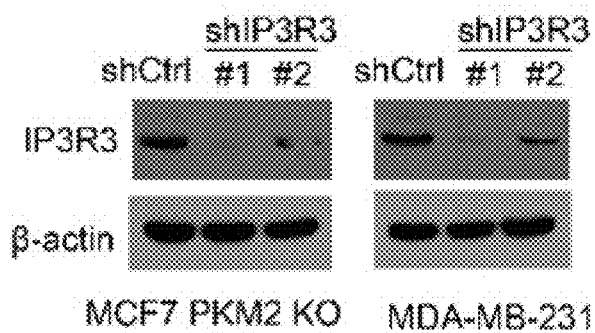
(FIG. 10M) Western blot analysis of IP3R3 knockdown efficiency in MCF7 PKM2 KO and MDA-MB-231 cells.
Figure 10N:
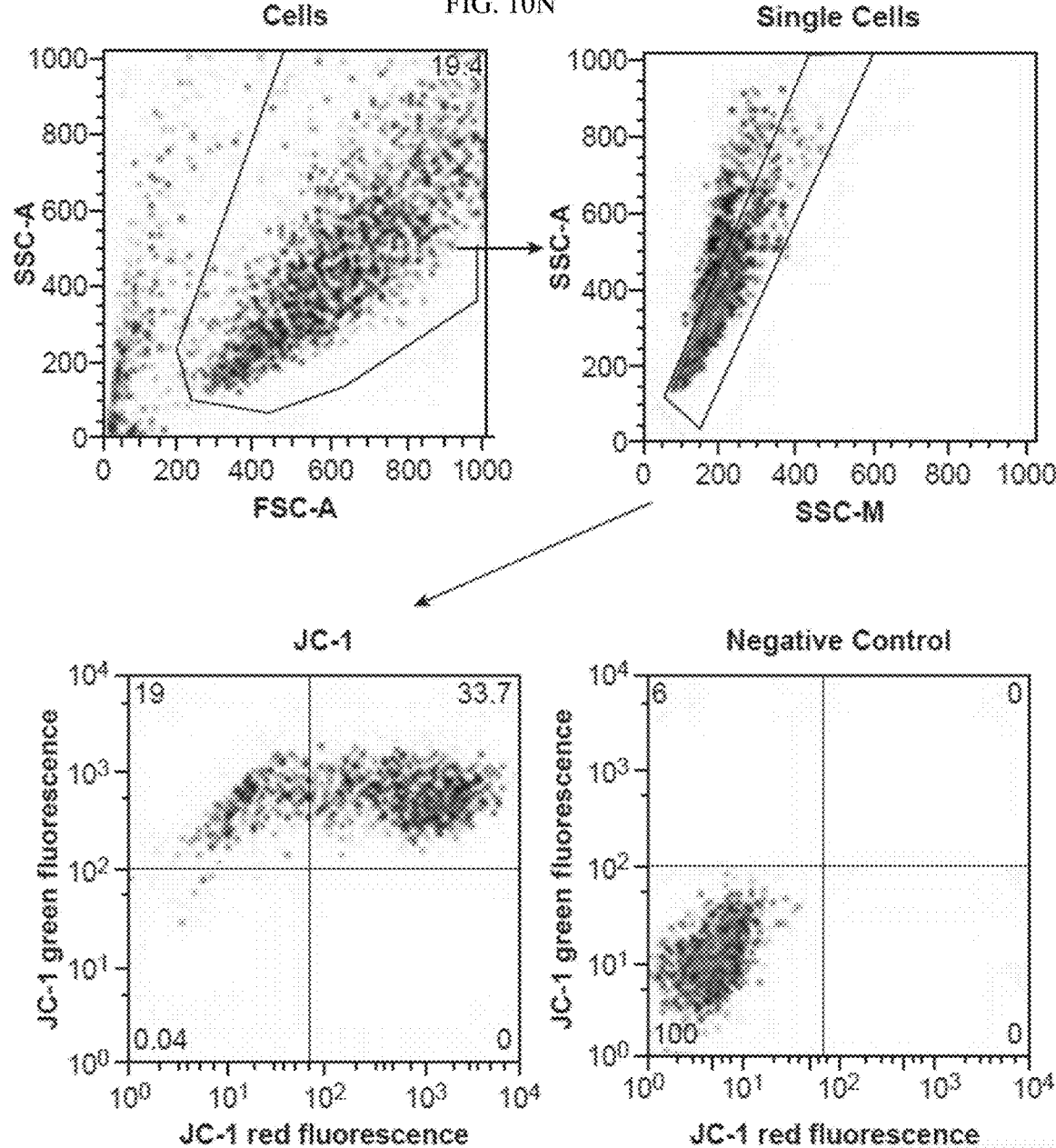
Figure 11F:
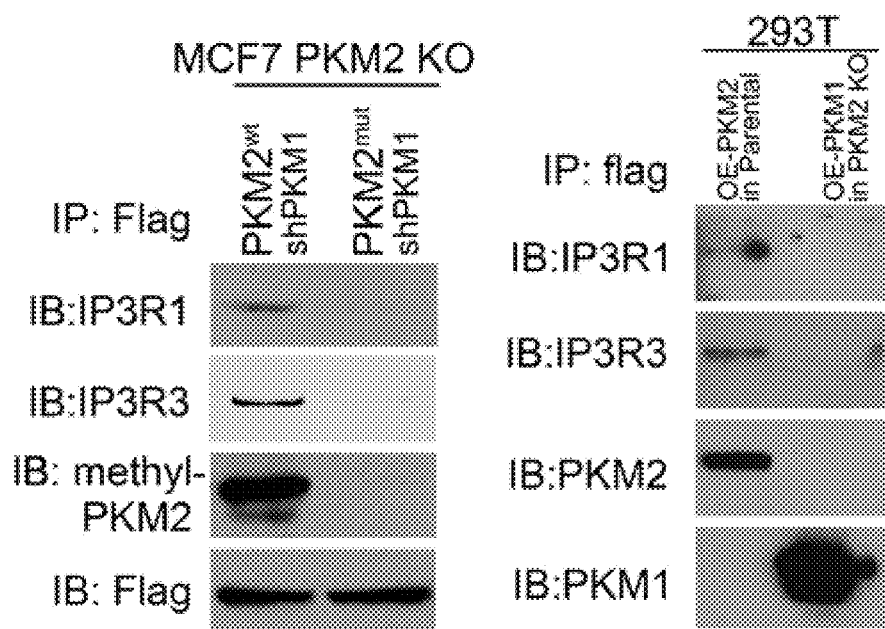
(FIG. 11F) Co-immunoprecipitation of IP3R1 and IP3R3 with PKM2$^{wt}$ but not PKM2$^{mut}$ in MCF7 (left panel) and overexpressed PKM1 in HEK293T PKM2 KO cells (right panel). IP3R1, IP3R3, PKM1, PKM2 and methyl-PKM2 are detected by Western blot in Flag-PKM1/2 immunoprecipitates using corresponding antibodies.
Figure 11G:
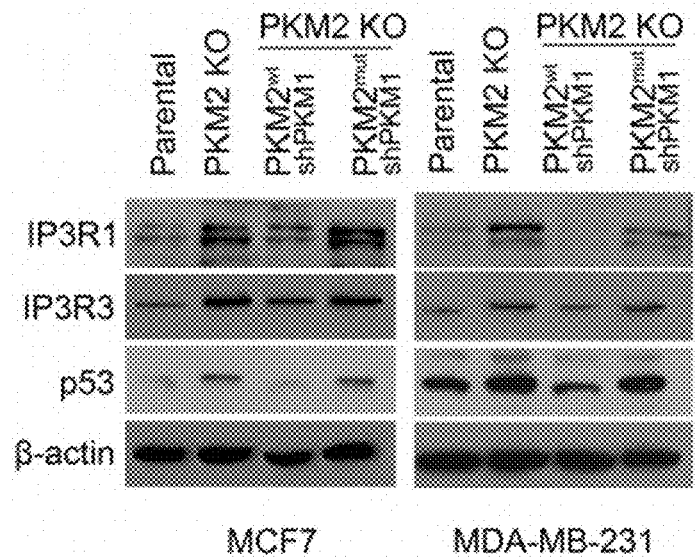
(FIG. 11G) Expression of IP3Rs and p53 by Western blot analysis in parental MCF7 (or MDA-MB-231), PKM2 KO, PKM2$^{wt}$/shPKM1 and PKM2$^{mut}$/shPKM1 cells.
Figure 11H:
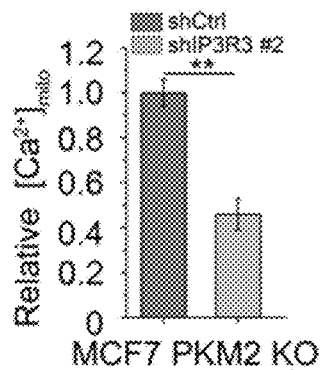
(FIGS. 11H-11I) Relative basal [Ca$^{2+}$]$_{mito}$ levels in MCF7 PKM2 KO and MDA-MB-231 cells with ctrl shRNA or IP3R3 shRNA knockdown (n=3).
Figure 11I:
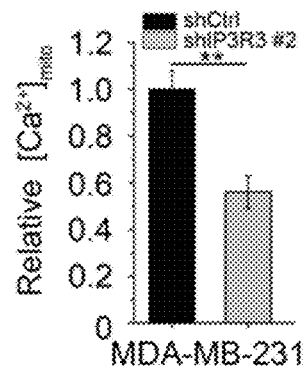
Figure 11J:
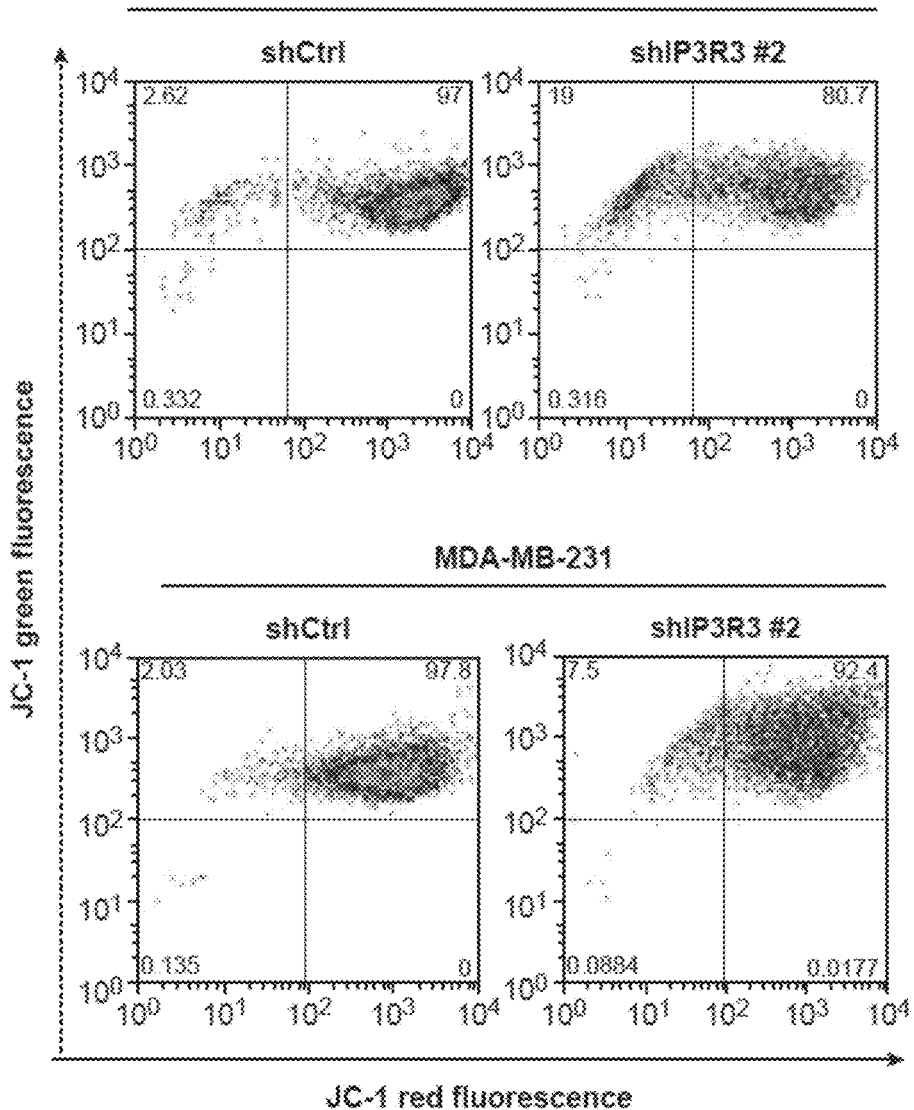
(FIG. 11J) ΔΨ measurement in MCF7 PKM2 KO and MDA-MB-231 cells with ctrl shRNA or IP3R3 shRNA knockdown.
Figure 11K:
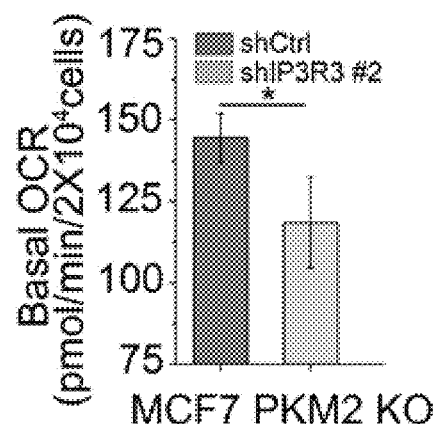
(FIGS. 11K-11L) Normalized basal OCR values in MCF7 PKM2 KO and MDA-MB-231 cells with ctrl shRNA or IP3R3 shRNA knockdown (n=6).
Figure 11L:
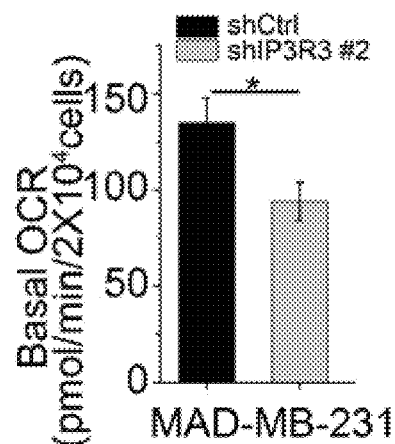
Figure 11M:
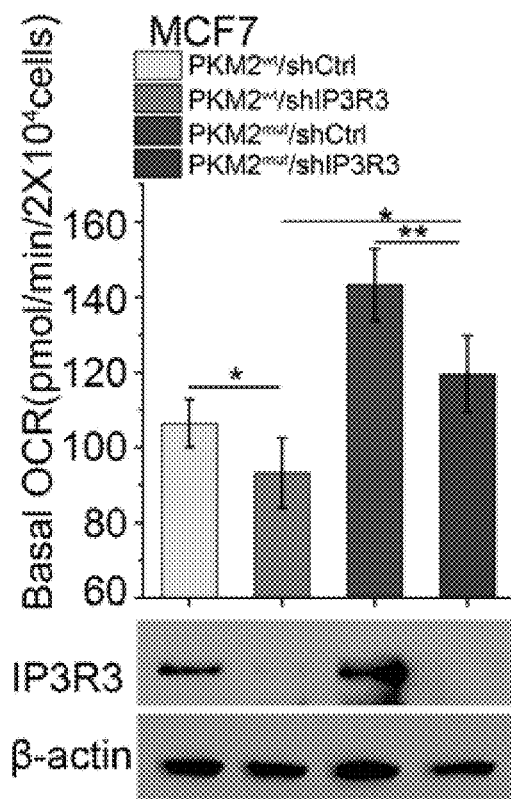
Figure 11N:
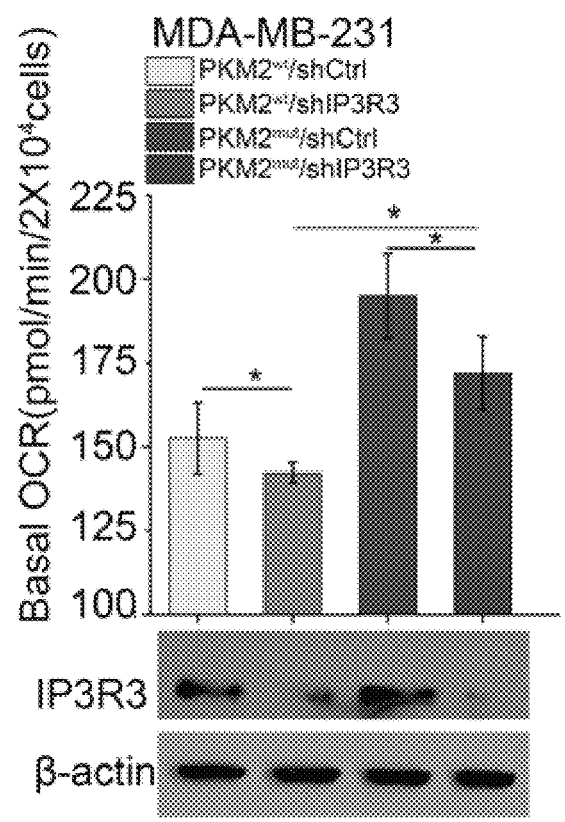

To determine if PKM2 and IP3Rs interaction is affected by PKM2 methylation, PKM2 was precipitated from MCF7 cells stably expressing Flag-tagged PKM2$^{wt}$ or PKM2$^{mut}$ using the anti-Flag M2 resin. The results showed that the interaction of PKM2 with IP3Rs could be detected in PKM2$^{wt}$ but not PKM2$^{mut}$ expressing cells (FIG. 11F, left panel). Even when Flag-PKM1 was overexpressed in HEK293T-PKM2 KO cells, no interaction between PKM1 and IP3Rs could be detected (FIG. 11F, right panel). The data suggests that PKM2 methylation is required for this interaction (FIG. 11F). Interestingly, the IP3Rs expression appears to be sensitive to PKM2 methylation since restoration of PKM2$^{wt}$, but not PKM2$^{mut}$, abrogated the elevated expression of IP3Rs in PKM2 KO cells (FIG. 11G). Furthermore, blocking PKM2 methylation by knocking out CARM1 or by treating with TEPP-46 resulted in elevated IP3R3 expression (FIG. 10H). The results suggest that IP3Rs expression is reversely correlated with methylated PKM2. ChIP-seq data have revealed p53 binding to IP3Rs promoters, indicating that IP3Rs could be p53 direct target genes. See Sanchez, Y. et al., "Genome-wide analysis of the human p53 transcriptional network unveils a lncRNA tumour suppressor signature," *Nat Commun* 5, 5812 (2014). It is noted that the mRNA levels of IP3Rs were increased by PKM2 KO, particularly in MDA-MB-231 cells (FIG. 10I), which is consistent with increased p53 protein levels in PKM2 KO clones of MCF7, MDA-MB-231 and MEF cells (FIGS. 11A-11B). Knocking down p53 using shRNAs significantly decreased IP3Rs proteins levels (FIG. 10J). The p53 protein level appears to be sensitive to PKM2 methylation status as restoration of PKM2$^{wt}$ but not PKM2$^{mut}$ reduced p53 expression (FIG. 11G). Conversely, knockout of CARM1 induced p53 expression (FIG. 10K). These data support that methylated PKM2, via down-regulating p53, is at least one means to control IP3Rs levels. Thus, while not being limited to a particular theory, it is possible that methylated PKM2 regulates mitochondrial functions through modulating the levels of IP3Rs which sustain mitochondria functions. To test this hypothesis, (KD) IP3R3 was stably knocked down in MCF7 PKM2 KO and MDA-MB-231 cell lines, which express high levels of IP3R3 (FIGS. 10L-10M). The results showed that IP3R3 KD reduced basal $[Ca^{2+}]_{mito}$ level (FIGS. 11H-11I) and $\Delta\Psi_m$ (FIG. 11J). Consistent with these results, the OCR was decreased by knocking down IP3R3 in MCF7 PKM2 KO cells (FIG. 11K) and MDA-MB-231 cells (FIG. 11I). To delineate the role of IP3Rs in PKM2 modulated mitochondrial activity, IP3R3 was knocked down in PKM2$^{wt}$ or PKM2$^{mut}$ expressing cells. The results showed that IP3R3 KD significantly reduced OCR in PKM2$^{wt}$ or PKM2$^{mut}$ cells. The basal OCR in PKM2$^{mut}$/shIP3R3 cells was higher than that in PKM2$^{wt}$/shIP3R3 cells, possibly due to contribution of other IP3Rs (IP3R1 and 2) that remain abundant in PKM2$^{mut}$ cells (FIGS. 11M-11N). Together, these findings demonstrated that methylated PKM2 repressed mitochondrial $Ca^{2+}$ uptake via interacting with and suppressing the expression of IP3Rs.

Figure 12A:
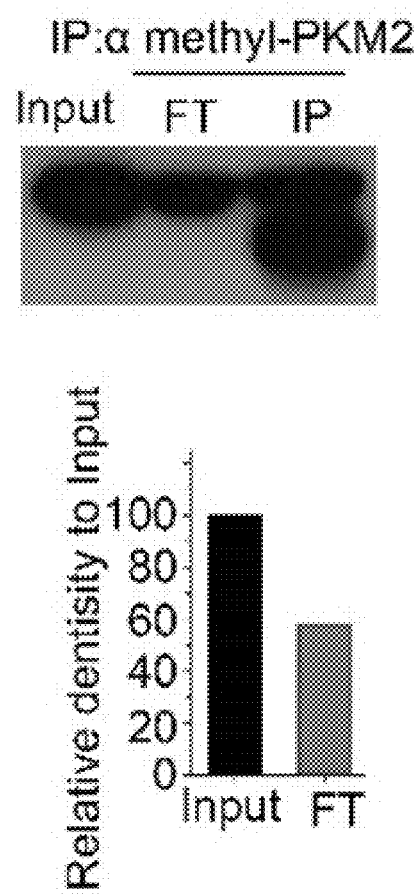
FIGS. 12A-12I show that cellular PKM2 methylation can be inhibited by unimolecular nanoparticle (UMNP) loaded with non-methyl-PKM2 peptide (SEQ ID NO: 1).
Figure 12B:
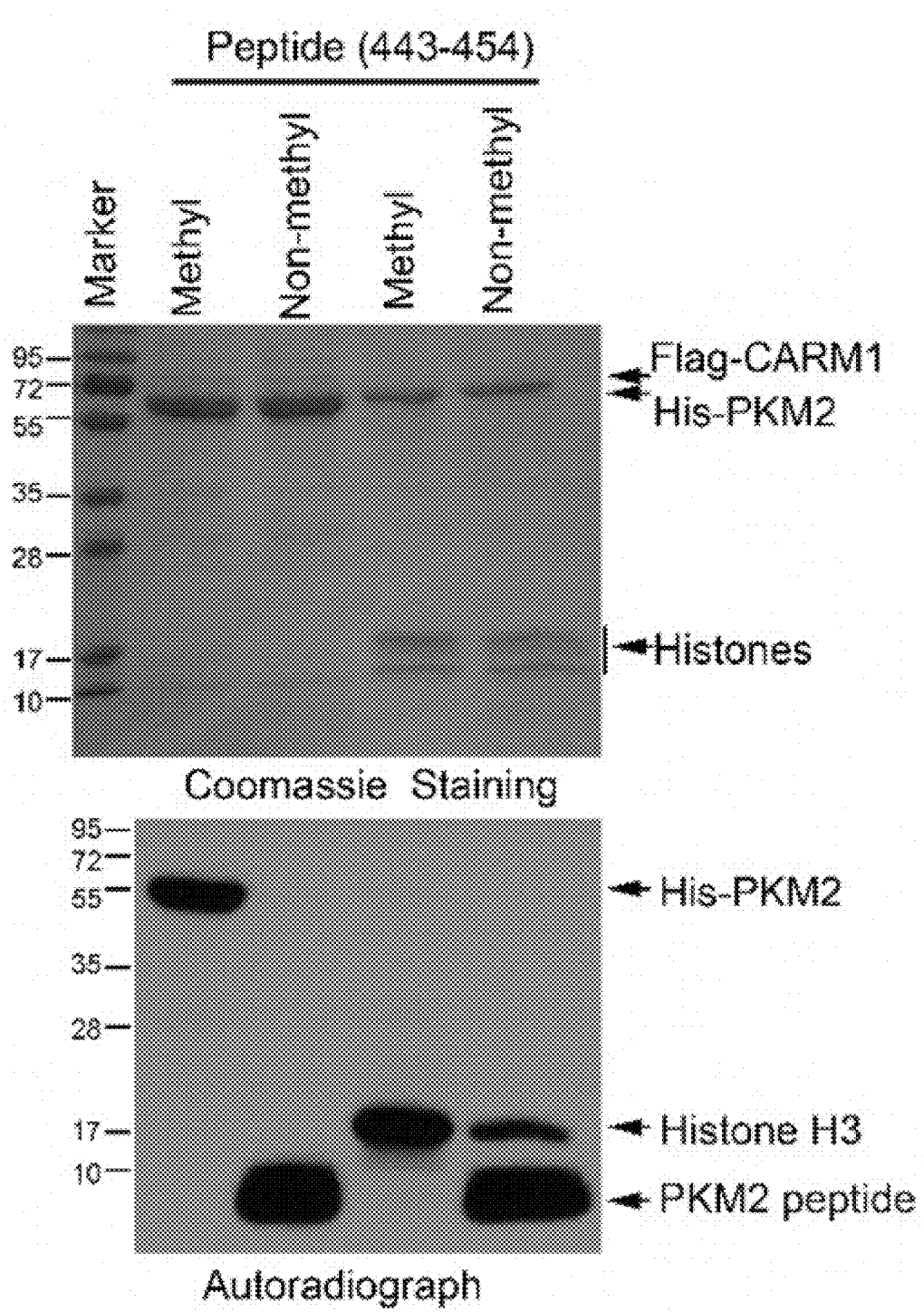
Figure 12C:
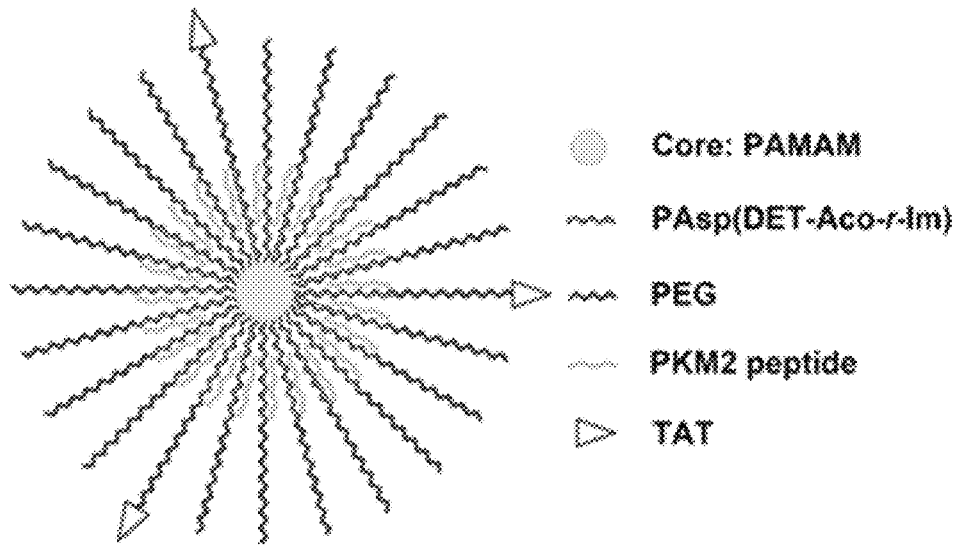
Figure 12D:
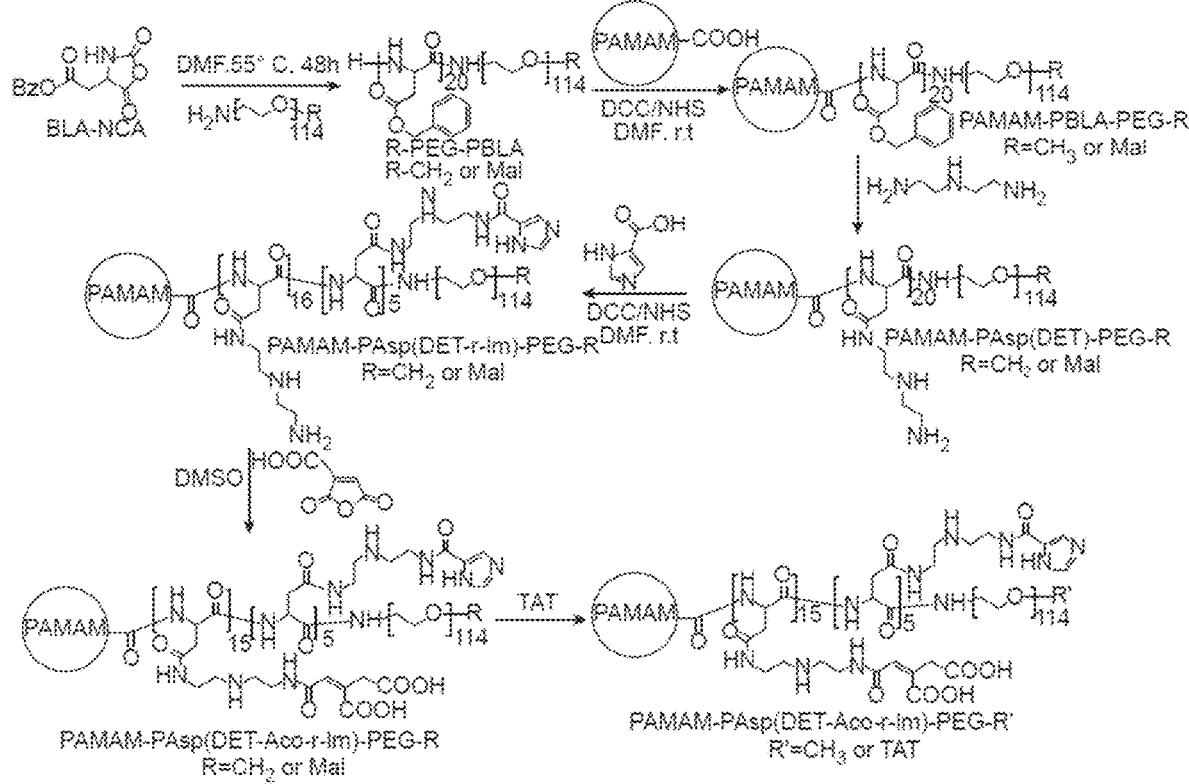
Figure 12E:
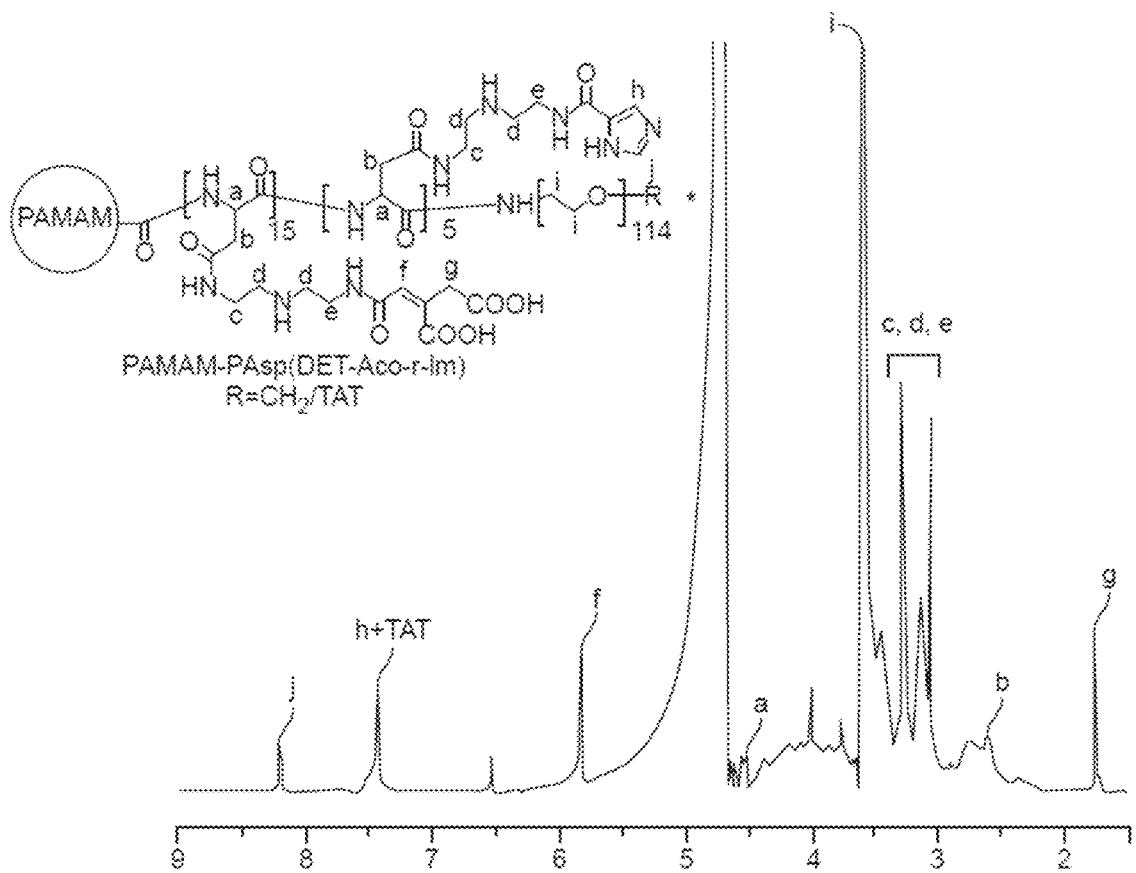
Figure 12F:
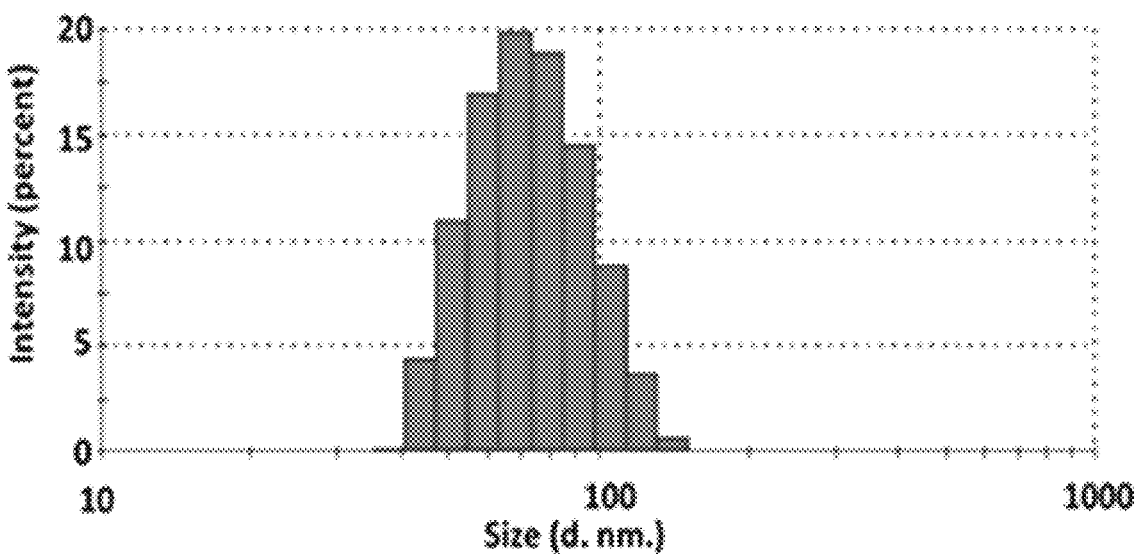

Example 8: Inhibition of PKM2 Methylation with a Competitive Peptide Delivered by Nanoparticle Blocks Cancer Cell Metastasis In Vivo Having established the role of PKM2 methylation in controlling ER-mitochondrial $Ca^{2+}$ signaling and promoting breast cancer cell proliferation and migration, whether PKM2 methylation can be therapeutically targeted was determined. To assess the dynamics of PKM2 methylation, the extent of endogenous PKM2 methylation was estimated in cancer cells. The excess amount of methyl-PKM2 antibody was used for immunoprecipitation and the proportion of PKM2 in the supernatant and pellets (i.e., in methylated form) in MCF7 cells was measured. The result showed that approximately 40% of the endogenous PKM2 was methylated (FIG. 12A) in MCF7 cells. The partial methylation of PKM2 in cancer cells implicates that PKM2 methylation is dynamic and regulatable. Peptide drugs have had a huge impact on cancer treatment and diagnosis. PKM2 methylation was inhibited with a competitive, non-methylated PKM2 peptide (SEQ ID NO:1) encompassing the methylation sites and whether cellular uptake of the peptide could inhibit endogenous PKM2 methylation was evaluated, leading to the reversal of aerobic glycolysis to oxidative phosphorylation. As a negative control, a corresponding peptide with R445 and R447 asymmetrically di-methylated was also synthesized. In the in vitro methylation assay, the non-methyl-peptide, but not the control methyl-peptide, abrogated CARM1-mediated methylation of PKM2 (FIG. 12B). In contrast, the peptides partially inhibited methylation of histone H3, the control substrate of CARM1, suggesting that PKM2 is the primary target of inhibition by this peptide.

Figure 12G:
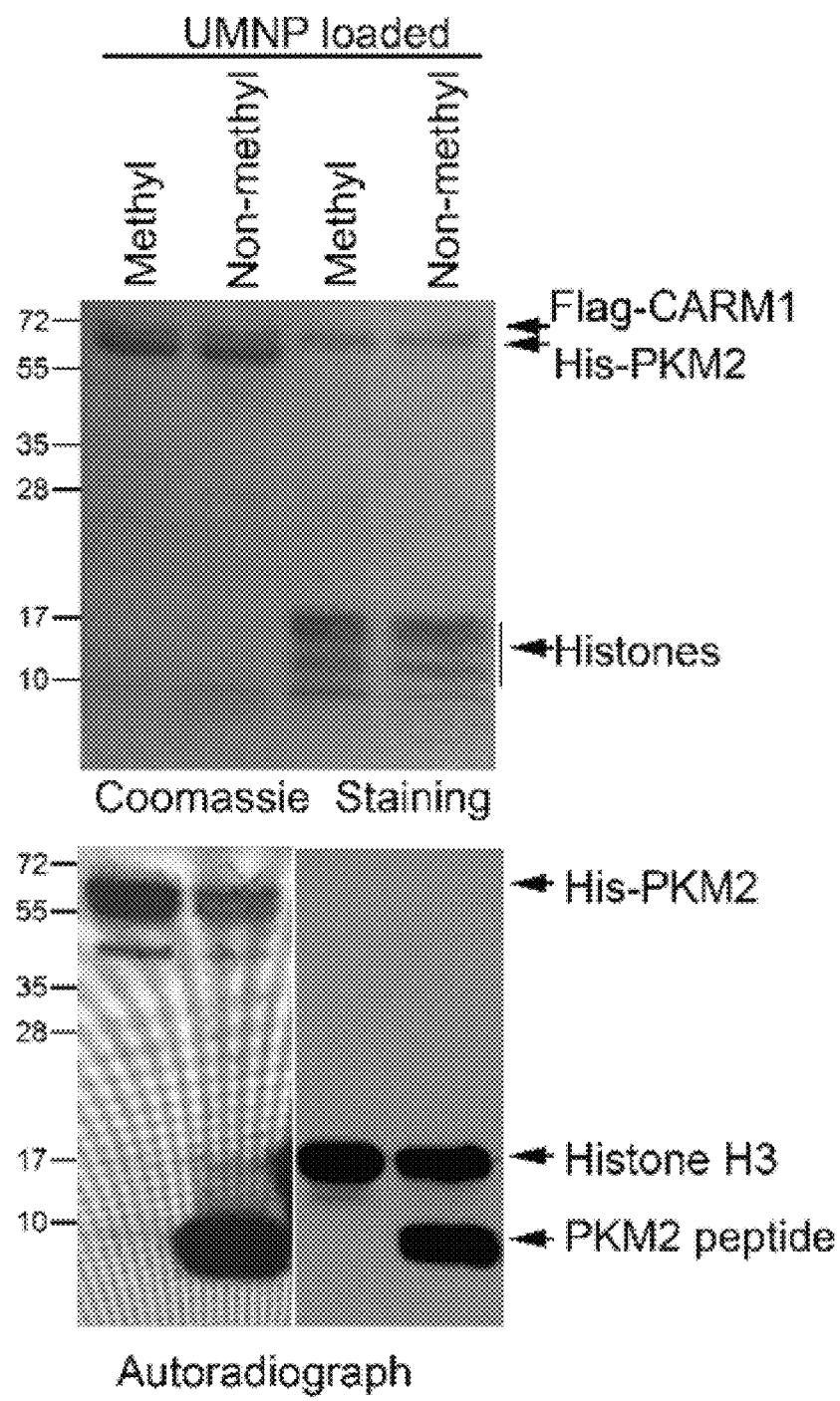
Figure 12H:
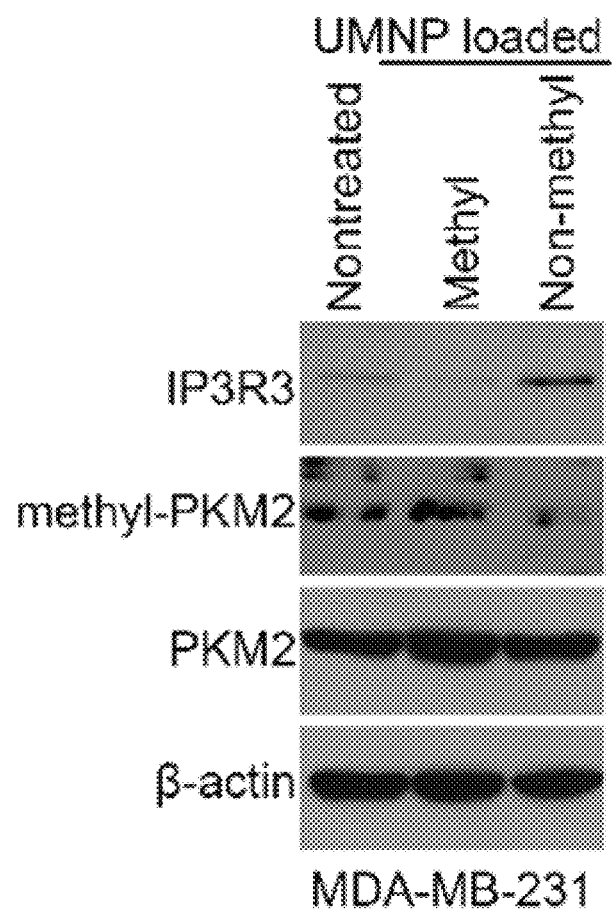
Figure 12I:
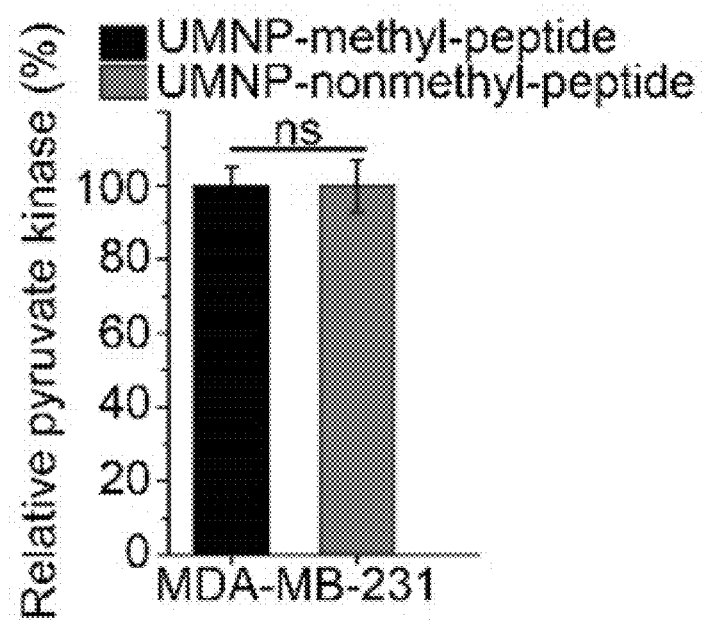
Figure 14A:
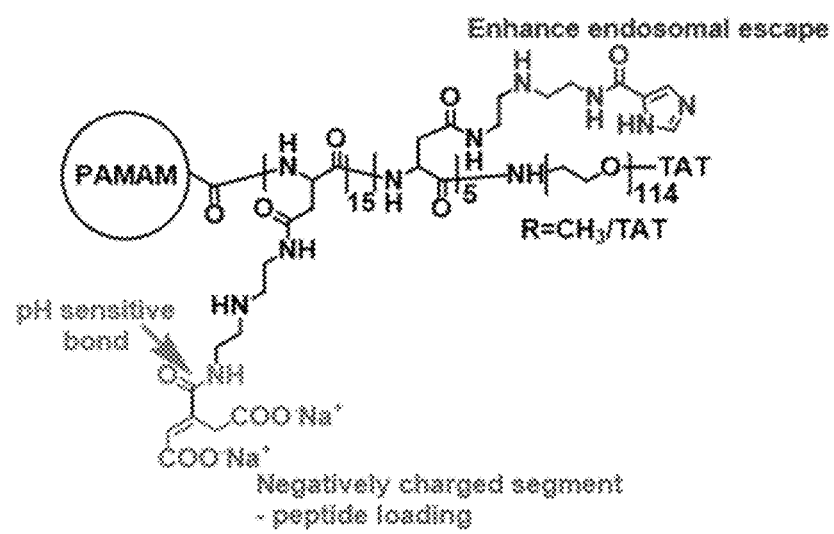
FIGS. 14A-14I show that inhibition of PKM2 methylation using a competitive PKM2 peptide reduces proliferation, migration, and lung metastasis of cancer cells due to increased oxidative phosphorylation.
Figure 14B:
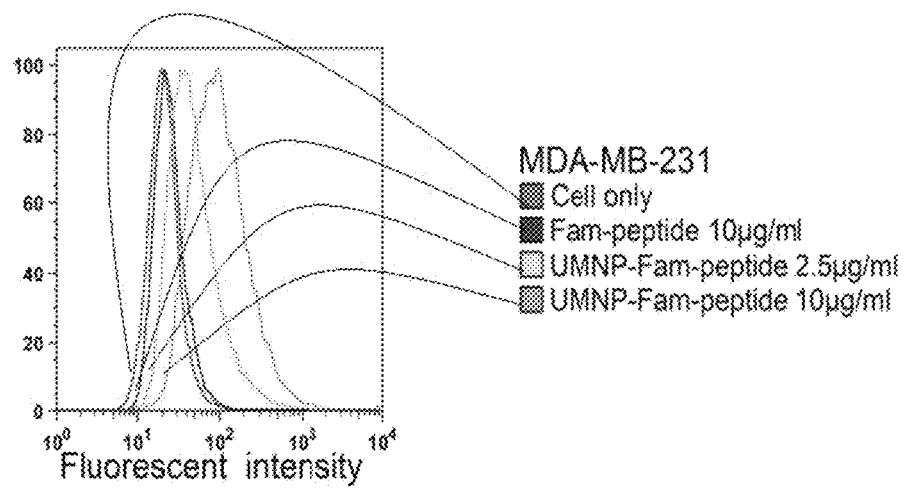
Figure 14C:
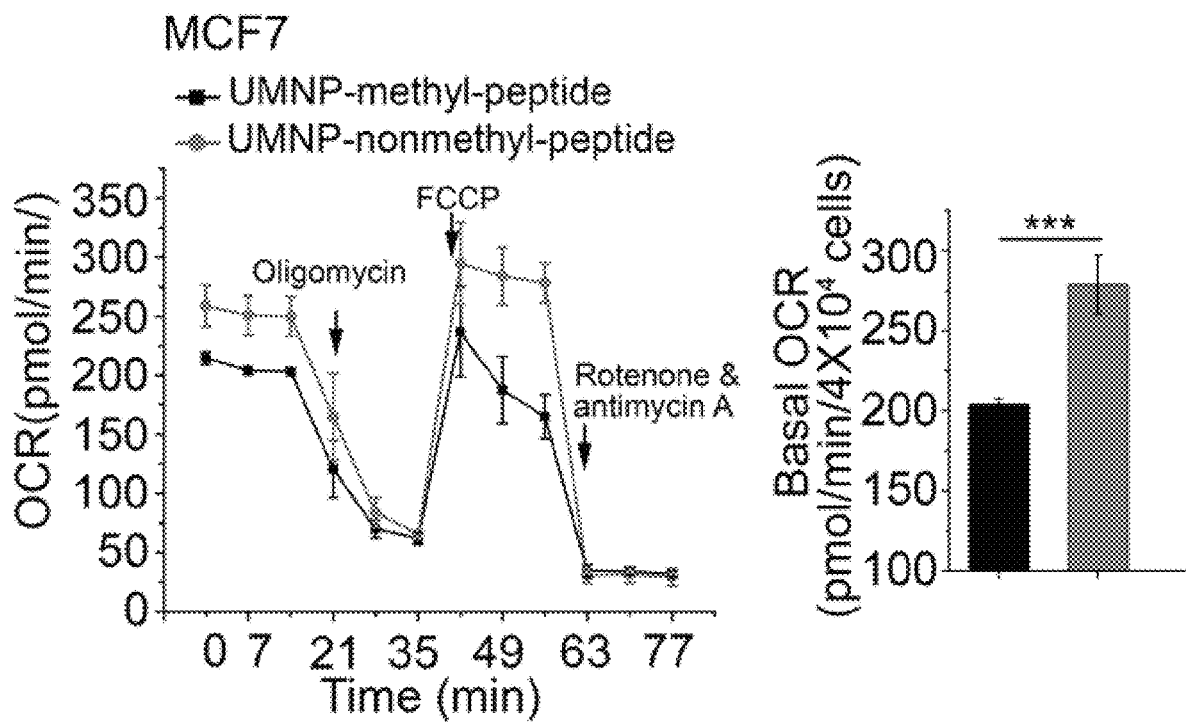
Figure 14D:
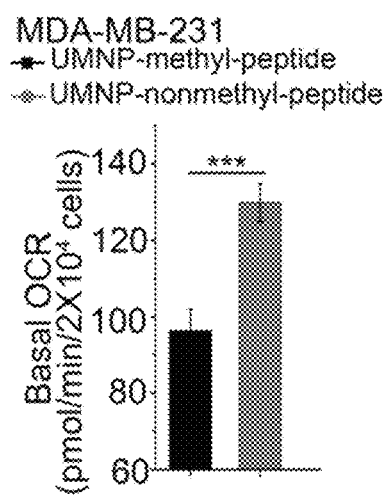
Figure 14E:
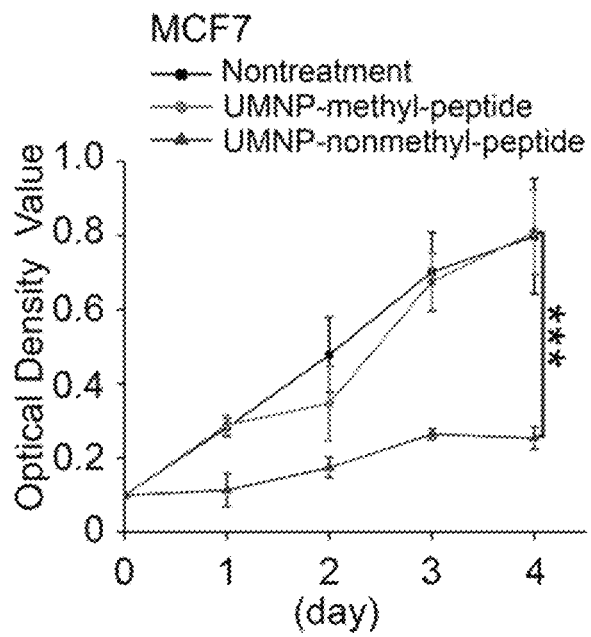
Figure 14F:
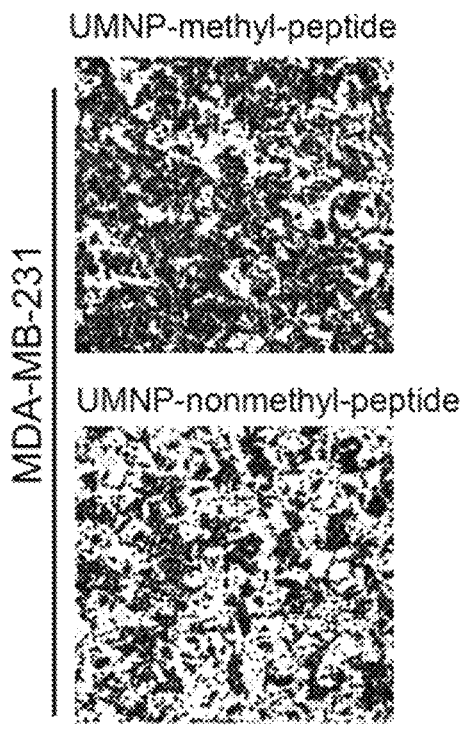
Figure 14G:
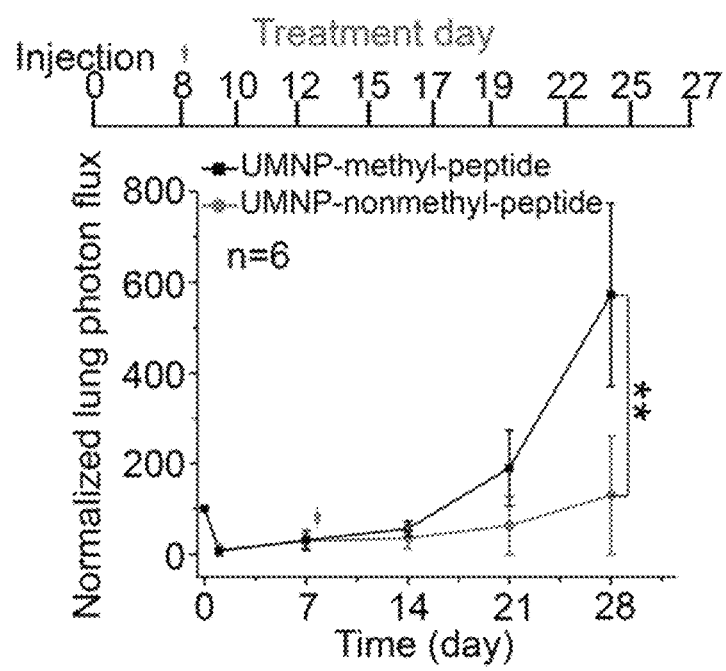
Figure 14H:
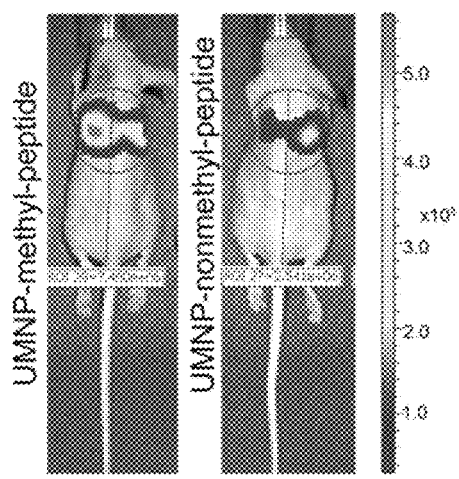
Figure 14I:
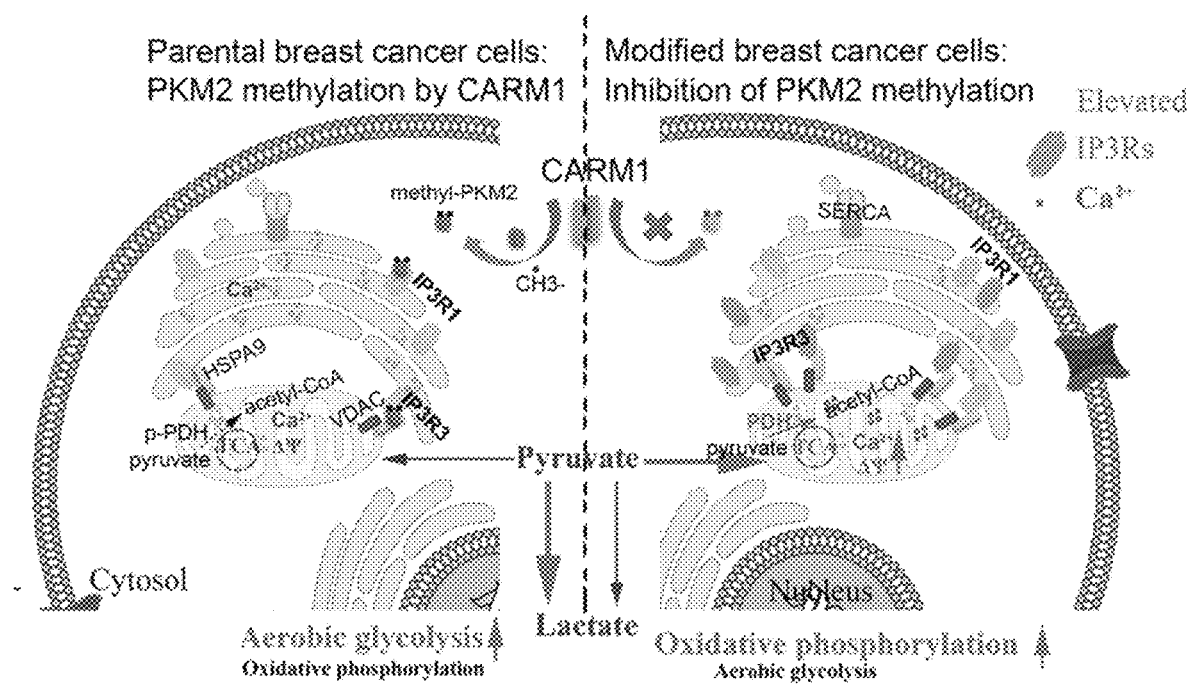

To test the biological effects of the PKM2 methylation peptide in vivo, a unique unimolecular nanoparticle (UMNP) made of multi-arm star block copolymer PAMAM-PAsp(DET-Aco-r-Im)-PEG was designed for delivery of PKM2 peptides (FIG. 14A and FIGS. 12C-12F). As shown in FIG. 14B, MDA-MB-231 cells efficiently uptook the 6-carboxyfluorescein-conjugated peptide of SEQ ID NO:1 (FAM-peptide) loaded UMNPs in a dose-dependent manner. To ensure that encapsulation of the PKM2 peptide inside UMNP did not alter its inhibitory activity, a PKM2 in vitro methylation assay was performed in the presence of non-methyl-peptide loaded UMNP or methyl-peptide loaded UMNP. The results showed that UMNP-non-methyl-peptide, but not UMNP-methyl-peptide, inhibited CARM1-mediated methylation of PKM2 (FIG. 12G). Under this condition, histone H3 methylation was not inhibited. The results imply that UMNP-non-methyl-peptide, similar to expressing PKM2$^{mut}$ and TEPP-46, selectively inhibited PKM2 methylation relative to other CARM1 substrates. Upon treatment with UMNP-non-methyl peptide, the OCR was significantly increased in the MCF7 and MDA-MB-231 cells in comparison with the UMNP-methyl-peptide control (FIGS. 14C-14D). In addition, only UMNP-non-methyl peptide could inhibit endogenous PKM2 methylation, leading to an increase in the IP3R3 protein level (FIG. 12H). Consistent with the finding that CARM1 KO did not affect the pyruvate kinase activity (FIG. 5C), inhibiting PKM2 methylation by UMNP-non-methyl-peptide did not alter the PKM2 pyruvate kinase activity either (FIG. 12I). Next, whether UMNP-non-methyl-peptide affects cell proliferation and migration was investigated. The results showed that non-methyl-peptide, but not methyl-peptide, inhibited proliferation of the MCF7 cells (FIG. 14E) and migration of MDA-MB-231 cells (FIG. 14F). To test whether the competitive PKM2 peptide inhibits breast cancer lung metastasis in vivo, LM2 cells (Minn et al., 2005), a MDA-MB-231 derivative clone selected for high lung metastasis tendency, were injected via tail vein into nude mice. While the majority of cells did not survive one day after injection, the remaining cells colonized in the lungs and reached 30-40% of the initial cell numbers by day 7. The mice were treated with UMNPs loaded with either methyl-peptide or non-methyl-peptide on day 8 and continued for 3-week treatment at the indicated time interval. LM2 colonization and outgrowth in the lungs of the two cohorts were monitored by bioluminescence imaging over time (Wang et al., 2014). The bioluminescence intensities in the UMNP-non-methyl peptide treated group were significantly decreased compared to those in the UMNP-methyl-peptide treated group, indicating that non-methyl peptide inhibited LM2 cell colonization in lungs (FIGS. 14G-14H). These results demonstrate the feasibility of targeting PKM2 methylation as a therapeutic strategy to reverse oncogenic processes.

Discussion. The results show that reversible PKM2 methylation can reprogram cancer metabolism from oxidative phosphorylation to aerobic glycolysis. PKM2 methylation by CARM1 inhibits $Ca^{2+}$ influx from ER to mitochondria. In breast cancer cells examined, herein, the mitochondrial oxidative phosphorylation dramatically increased upon loss of CARM1, or PKM2, or PKM2 methylation, which leads to the increased basal mitochondrial $[Ca^{2+}]$ and higher $\Delta\Psi_m$. Therefore, the results provide mechanistic insights into the metabolic reprogramming controlled by the CARM1-PKM2 axis in breast cancer cells and indicate that inhibiting PKM2 methylation has therapeutic application.

It has been recognized that PKM2 plays an important role in aerobic glycolysis by distributing glycolytic intermediates for anabolic and catabolic purposes in cancer cells. Several post-translational modifications of PKM2 have been reported to modulate PKM2 function, including phosphorylation of Tyr 105 and oxidation of Cys358 which inhibit its pyruvate kinase activity. However, a recent study challenged PKM2-catalyzed reaction as a rate-limiting step in cancer cell glycolysis. Consistent with this, PKM2 pyruvate kinase activity was not affected by knocking out CARM1 (FIG. 5C), or by inhibiting PKM2 methylation using non-methyl PKM2 peptide (FIG. 12H), suggesting that PKM2 methylation may have little effect on its pyruvate kinase activity. The mitochondrial oxidative phosphorylation was increased in CARM1 KO, PKM2 KO or PKM2$^{mut}$ expressing breast cancer cells, suggesting that non-glycolytic function of PKM2 regulates aerobic glycolysis rather than pyruvate kinase activity. In contrast, PKM2 methylation shows effects on energy production by altering mitochondrial oxidative phosphorylation. The shift of energy production controlled by PKM2 methylation in MCF7 cells is notable since restoration of PKM1 in PKM2 knockdown MCF7 cells failed to alter lactate production or oxygen consumption, even though PKM1 expression is sufficient to increase oxidative phosphorylation in other cancer types. While not being limited to a particular theory, it is possible that the remaining PKM2 in MCF7 PKM2 knockdown cells partially executed its non-glycolytic function. Mitochondria have a well-recognized role in the production of ATP and intermediates needed for macromolecule biosynthesis in many normal and cancerous cells may act as promising chemotherapeutic targets. In breast cancer cells, knockdown of mitochondrial p32, a critical regulator of tumor metabolism via maintenance of oxidative phosphorylation, shifted metabolism from oxidative phosphorylation to glycolysis, yet tumorigenesis was impaired, suggesting that high levels of glycolysis without adequate oxidative phosphorylation does not always benefit tumor growth. Thus, our results support the theory that the balance between aerobic glycolysis and mitochondrial respiration is essential for tumor progression.

Cancer cells rely on mitochondria for metabolic intermediates production from the tricarboxylic acid (TCA) cycle to fuel lipid, nucleic acid, and protein biosynthesis essential for rapid growth. The TCA cycle is critically regulated by mitochondrial $Ca^{2+}$, which activates several matrix dehydrogenases including pyruvate-, α-ketoglutarate- and isocitrate-dehydrogenases, to promote oxidative phosphorylation and ATP production. Mitochondrial $Ca^{2+}$ has two resources. It is primarily taken from endoplasmic reticulum (ER) at proximal contact site of two organelles known as mitochondria-associated ER membrane (MAM). A minor fraction is from cytosol through low-affinity mitochondrial calcium uniporters (MCUs). Both processes are tightly controlled by IP3Rs, the ubiquitous family of $Ca^{2+}$ release channels located primary in ER of all cell types. There are three types of IP3Rs, among which IP3R1 and IP3R3 are best studied and show distinct effect on $Ca^{2+}$ signaling. IP3R3 at MAM selectively mediates $Ca^{2+}$ release from ER to mitochondria, while IP3R1 mainly mediates $Ca^{2+}$ release from cytosol. Because cytosolic $Ca^{2+}$ concentration is usually low and inadequate to activate MCUs, it is postulated that $Ca^{2+}$ released from ER via IP3R3 generate a high-density calcium gradient at MAM to activate MCUs and facilitate $Ca^{2+}$ transport from cytosol to mitochondria. Thus, IP3R1 and IP3R3 cooperate to play important roles in supplying released $Ca^{2+}$ to mitochondria. IP3R3 mediated $Ca^{2+}$ release from ER to mitochondria activates MCUs; activated MCUs, in turn, takes up $Ca^{2+}$ released by IP3R1. Both IP3R1 and IP3R3 expression levels are reversely associated with PKM2 expression, moreover, their levels are sensitive to PKM2 methylation status, i.e., high IP3Rs in PKM2 methylation defective cells. As a consequence, mitochondrial $Ca^{2+}$ uptake increases in PKM2 methylation defective cells, which leads to activation of PDH and increase of oxidative phosphorylation. PKM2 methylation, on the contrary, decreases IP3Rs expression and $[Ca^{2+}]_{mito}$, which result in increased PDH phosphorylation and inactivation, decrease of $\Delta\Psi_m$, and the switch of energy homeostasis from mitochondrial respiration to aerobic glycolysis. The exact mechanism by which methylated PKM2 suppress the expression of IP3Rs is unknown and warrants further studies. In addition to control IP3R expression, methylated PKM2 can be co-precipitated with IP3R1 and IP3R3 (FIG. 11F). Whether such interaction is direct or indirect is unknown. It has been reported that Sigma-1 receptor, an ER chaperone, is enriched at MAM and forms a complex with BIP (GRP78, also known as HSPA5). Upon activation of IP3Rs, Sigma-1 receptor dissociates from BiP and binds to IP3R3 at MAM, thereby preventing IP3R3 (not IP3R1) degradation and sustaining $Ca^{2+}$ uptake by mitochondria. A portion of PKM2 was found to be localized in mitochondria and interacts with HSPA5/BIP.

Mitochondrial $Ca^{2+}$ addiction was recently identified as a feature of cancer cells (Cardenas et al., 2016). While inhibition of ER-to-mitochondria $Ca^{2+}$ transfer creates a bioenergetic crisis to normal and tumor cells, normal cells trigger autophagy to sustain survival, whereas the same autophagy response in tumor cells is insufficient for maintenance of survival. Tumor cell survival uniquely depends on the constitutive ER-to-mitochondria $Ca^{2+}$ transfer, which is regulated by IP3Rs, since inhibition of IP3R activity reduces the proliferative potential of cancer cell lines in vitro and impair tumor growth in vivo. In alignment with this finding, increased IP3R expression and/or activity have been associated with cancer cell proliferation, survival and invasiveness. All three IP3R subtypes are expressed in breast cancer cells at various levels to regulate intracellular $Ca^{2+}$ release, which is essential for growth control of these cells (Cardenas et al., 2016). Although inhibiting PKM2 methylation reduces tumor cell growth, migration and metastasis in various breast cancer cell lines, inhibiting PKM2 methylation alone is insufficient to alter cell survival (FIG. 5J), whereas inhibiting both PKM2 methylation and IP3Rs activity are lethal to cancer cells (FIGS. 9C-9F). The results underscore gain-of-dependence of cancer cells to IP3R-mediated $Ca^{2+}$ transport for maintaining cell viability. The acquired mitochondrial addition to $Ca^{2+}$ renders susceptibility of cancer cells to therapies based on inhibition of IP3R activities (e.g., XeB). Thus, combinatory inhibition of IP3R activity and PKM2 methylation may elicit synergistic therapeutic effects. Targeting cancer-specific metabolism pathways (i.e., aerobic glycolysis and ER-to-mitochondria $Ca^{2+}$ transfer) may provide new therapeutic revenue for cancer treatment, as exemplified by the UMNP peptide delivery system of the present technology.

EQUIVALENTS

While certain embodiments have been illustrated and described, a person with ordinary skill in the art, after reading the foregoing specification, can effect changes, substitutions of equivalents and other types of alterations to the conjugates and nanoparticles of the present technology or derivatives, prodrugs, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conjugates, reagents, compounds, compositions, labeled compounds or biological systems, which can, of course, vary. All methods described herein can be performed in any suitable order unless otherwise indicated herein or otherwise clearly contradicted by context. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the technology. This includes the generic description of the technology with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, and each separate value is incorporated into the specification as if it were individually recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A composition comprising a peptide or a pharmaceutically acceptable salt thereof and a pharmaceutically acceptable carrier, wherein the peptide comprises an amino acid sequence having at least about 85% sequence identity to RYRPRAPIIAVT (SEQ ID NO: 1), (i) wherein the amino acid sequence does not vary at residues RPRAP (SEQ ID NO: 6), and (ii) wherein the peptide has a length of from 12 to 26 amino acids.

2. The composition of claim 1, wherein the peptide has a length selected from the group consisting of:

(i) 12 amino acids;
(ii) 14 amino acids;
(iii) 15 amino acids;
(iv) 19 amino acids; and
(v) 26 amino acids.

3. The composition of claim 1, wherein the amino acid sequence has at least about 90% identity to SEQ ID NO: 1.

4. The composition of claim 1, wherein the amino acid sequence has 100% sequence identity to SEQ ID NO: 1.

5. The composition of claim 4, wherein the peptide has a length of 12 amino acids.

6. A peptide consisting of the amino acid sequence RYRPRAPIIAVT (SEQ ID NO: 1).

* * * * *

SEQUENCE LISTING

```
<160> NUMBER OF SEQ ID NOS: 71

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Tyr Arg Pro Arg Ala Pro Ile Ile Ala Val Thr
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Ala Arg Tyr Arg Pro Arg Ala Pro Ile Ile Ala Val Thr
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Tyr Arg Pro Arg Ala Pro Ile Ile Ala Val Thr Arg Asn Pro
1               5                   10                  15

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

```
Arg Ser Ala His Gln Val Ala Arg Tyr Arg Pro Arg Ala Pro Ile Ile
1               5                   10                  15

Ala Val Thr

<210> SEQ ID NO 5
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Gly Arg Ser Ala His Gln Val Ala Arg Tyr Arg Pro Arg Ala Pro
1               5                   10                  15

Ile Ile Ala Val Thr Arg Asn Pro Gln Thr
            20                  25

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Pro Arg Ala Pro
1               5

<210> SEQ ID NO 7
<211> LENGTH: 12
<212> TYPE: PRT
<213> ORGANISM: Human immunodeficiency virus

<400> SEQUENCE: 7

Gly Arg Lys Lys Arg Arg Gln Arg Arg Arg Pro Gln
1               5                   10

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Leu Ala Leu Lys Leu Ala Leu Lys Ala Leu Lys Ala Ala Leu Lys
1               5                   10                  15

Leu Ala

<210> SEQ ID NO 9
<211> LENGTH: 15
<212> TYPE: PRT
<213> ORGANISM: Drosophila sp.

<400> SEQUENCE: 9

Arg Gln Ile Lys Trp Phe Gln Asn Arg Arg Met Lys Trp Lys Lys
1               5                   10                  15

<210> SEQ ID NO 10
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 10

Arg Gln Ile Arg Ile Trp Phe Gln Asn Arg Arg Met Arg Trp Arg Arg
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Ser Ile Pro Pro Glu Val Lys Phe Asn Lys Pro Phe Val Tyr Leu
1               5                   10                  15

Ile

<210> SEQ ID NO 12
<211> LENGTH: 13
<212> TYPE: PRT
<213> ORGANISM: Rana temporaria

<400> SEQUENCE: 12

Phe Val Gln Trp Phe Ser Lys Phe Leu Gly Arg Ile Leu
1               5                   10

<210> SEQ ID NO 13
<211> LENGTH: 10
<212> TYPE: PRT
<213> ORGANISM: Maurus palmatus

<400> SEQUENCE: 13

Gly Asp Cys Leu Pro His Leu Lys Leu Cys
1               5                   10

<210> SEQ ID NO 14
<211> LENGTH: 18
<212> TYPE: PRT
<213> ORGANISM: Mus sp.

<400> SEQUENCE: 14

Leu Leu Ile Ile Leu Arg Arg Arg Ile Arg Lys Gln Ala His Ala His
1               5                   10                  15

Ser Lys

<210> SEQ ID NO 15
<211> LENGTH: 24
<212> TYPE: PRT
<213> ORGANISM: Homo sapiens

<400> SEQUENCE: 15

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 16
<211> LENGTH: 30
<212> TYPE: PRT
<213> ORGANISM: Unknown
```

```
<220> FEATURE:
<223> OTHER INFORMATION: Description of Unknown:
      Neurturin sequence

<400> SEQUENCE: 16

Gly Ala Ala Glu Ala Ala Ala Arg Val Tyr Asp Leu Gly Leu Arg Arg
1               5                   10                  15

Leu Arg Gln Arg Arg Arg Leu Arg Arg Glu Arg Val Arg Ala
            20                  25                  30

<210> SEQ ID NO 17
<211> LENGTH: 18
<212> TYPE: PRT
<213> ORGANISM: Drosophila sp.

<400> SEQUENCE: 17

Arg Gln Ile Lys Ile Trp Phe Gln Asn Arg Arg Met Lys Trp Lys Lys
1               5                   10                  15

Gly Gly

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Arg Arg Arg Gln Arg Arg Lys Lys Arg Gly Gly Asp Ile Met Gly Glu
1               5                   10                  15

Trp Gly Asn Glu Ile Phe Gly Ala Ile Ala Gly Phe Leu Gly
            20                  25                  30

<210> SEQ ID NO 19
<211> LENGTH: 11
<212> TYPE: PRT
<213> ORGANISM: Human immunodeficiency virus

<400> SEQUENCE: 19

Tyr Gly Arg Lys Lys Arg Arg Gln Arg Arg Arg
1               5                   10

<210> SEQ ID NO 20
<211> LENGTH: 18
<212> TYPE: PRT
<213> ORGANISM: Unknown
<220> FEATURE:
<223> OTHER INFORMATION: Description of Unknown:
      SynB1 sequence

<400> SEQUENCE: 20

Arg Gly Gly Arg Leu Ser Tyr Ser Arg Arg Arg Phe Ser Thr Ser Thr
1               5                   10                  15

Gly Arg

<210> SEQ ID NO 21
<211> LENGTH: 10
<212> TYPE: PRT
<213> ORGANISM: Unknown
<220> FEATURE:
<223> OTHER INFORMATION: Description of Unknown:
      SynB3 sequence

<400> SEQUENCE: 21
```

```
Arg Arg Leu Ser Tyr Ser Arg Arg Phe
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Ile Arg Arg Arg Lys Lys Leu Arg Arg Leu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Arg Gln Arg Arg Thr Ser Lys Leu Met Lys Arg
1               5                   10

<210> SEQ ID NO 24
<211> LENGTH: 15
<212> TYPE: PRT
<213> ORGANISM: Flock house virus

<400> SEQUENCE: 24

Arg Arg Arg Arg Asn Arg Thr Arg Arg Asn Arg Arg Arg Val Arg
1               5                   10                  15

<210> SEQ ID NO 25
<211> LENGTH: 19
<212> TYPE: PRT
<213> ORGANISM: Brome mosaic virus

<400> SEQUENCE: 25

Lys Met Thr Arg Ala Gln Arg Arg Ala Ala Ala Arg Arg Asn Arg Trp
1               5                   10                  15

Thr Ala Arg

<210> SEQ ID NO 26
<211> LENGTH: 13
<212> TYPE: PRT
<213> ORGANISM: Human T-cell leukemia virus II

<400> SEQUENCE: 26

Thr Arg Arg Gln Arg Thr Arg Arg Ala Arg Arg Asn Arg
1               5                   10

<210> SEQ ID NO 27
<211> LENGTH: 13
<212> TYPE: PRT
<213> ORGANISM: Human immunodeficiency virus

<400> SEQUENCE: 27

Gly Arg Lys Lys Arg Arg Gln Arg Arg Arg Pro Pro Gln
1               5                   10
```

-continued

```
<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Arg Arg Arg Arg Arg Arg Arg Arg Pro Pro Gln
1               5                   10

<210> SEQ ID NO 29
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Leu Ala Leu Lys Leu Ala Leu Lys Leu Ala Leu Ala Leu Lys Leu
1               5                   10                  15

Ala

<210> SEQ ID NO 31
<211> LENGTH: 27
<212> TYPE: PRT
<213> ORGANISM: Homo sapiens

<400> SEQUENCE: 31

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 32
<211> LENGTH: 27
<212> TYPE: PRT
<213> ORGANISM: Unknown
<220> FEATURE:
<223> OTHER INFORMATION: Description of Unknown:
      FBP sequence

<400> SEQUENCE: 32

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 33
```

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 34
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(17)
<223> OTHER INFORMATION: This sequence may encompass 4-17 residues
```

```
<400> SEQUENCE: 37

Arg Arg Arg Arg Arg Arg Arg Arg Arg Arg Arg Arg Arg Arg Arg
1               5                   10                  15

Arg

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(17)
<223> OTHER INFORMATION: This sequence may encompass 4-17 residues

<400> SEQUENCE: 38

Lys Lys Lys Lys Lys Lys Lys Lys Lys Lys Lys Lys Lys Lys Lys
1               5                   10                  15

Lys

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminocaproic acid
<220> FEATURE:
<221> NAME/KEY: MOD_RES
<222> LOCATION: (4)..(4)
<223> OTHER INFORMATION: Aminocaproic acid
<220> FEATURE:
<221> NAME/KEY: MOD_RES
<222> LOCATION: (6)..(6)
<223> OTHER INFORMATION: Aminocaproic acid
<220> FEATURE:
<221> NAME/KEY: MOD_RES
<222> LOCATION: (8)..(8)
<223> OTHER INFORMATION: Aminocaproic acid
<220> FEATURE:
<221> NAME/KEY: MOD_RES
<222> LOCATION: (10)..(10)
<223> OTHER INFORMATION: Aminocaproic acid
<220> FEATURE:
<221> NAME/KEY: MOD_RES
<222> LOCATION: (12)..(12)
<223> OTHER INFORMATION: Aminocaproic acid

<400> SEQUENCE: 39

Arg Xaa Arg Xaa Arg Xaa Arg Xaa Arg Xaa Arg Xaa Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminobutyric acid
<220> FEATURE:
<221> NAME/KEY: MOD_RES
```

```
<222> LOCATION: (4)..(4)
<223> OTHER INFORMATION: Aminobutyric acid
<220> FEATURE:
<221> NAME/KEY: MOD_RES
<222> LOCATION: (6)..(6)
<223> OTHER INFORMATION: Aminobutyric acid
<220> FEATURE:
<221> NAME/KEY: MOD_RES
<222> LOCATION: (8)..(8)
<223> OTHER INFORMATION: Aminobutyric acid
<220> FEATURE:
<221> NAME/KEY: MOD_RES
<222> LOCATION: (10)..(10)
<223> OTHER INFORMATION: Aminobutyric acid
<220> FEATURE:
<221> NAME/KEY: MOD_RES
<222> LOCATION: (12)..(12)
<223> OTHER INFORMATION: Aminobutyric acid

<400> SEQUENCE: 40

Arg Xaa Arg Xaa Arg Xaa Arg Xaa Arg Xaa Arg Xaa Arg
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Gly Arg Gly Arg Gly Arg Gly Arg Gly Arg Gly Arg
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Met Arg Met Arg Met Arg Met Arg Met Arg Met Arg
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Thr Arg Thr Arg Thr Arg Thr Arg Thr Arg Thr Arg
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ser Arg Ser Arg Ser Arg Ser Arg Ser Arg Ser Arg
1               5                   10
```

```
<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Arg Arg Arg Arg Arg Arg Arg Arg Arg
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ala Arg Ala Arg Ala Arg Ala Arg Ala Arg Ala Arg
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Arg Arg Arg Arg Arg Arg
1               5

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tcccctagat tgcccgtgag                                              20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
attgttcaat ggactgctcc c                                            21

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
```
agaacttgtg cgagcctcaa                                                20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gacgagctgt ctggggattc                                                20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gtgatgtggc caatgcagtc                                                20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
caagtggtag atggcagcct                                                20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cacccaagaa cagggtttgt                                                20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tggccatggg tatgttgtta                                                20

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgctgtctcc atgtttgatg tatct					25

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tctctgctcc ccacctctaa gt					22

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Tyr Arg Pro Arg Ala Pro Ile Ile Ala Val Thr Cys
1               5                   10

<210> SEQ ID NO 59
<211> LENGTH: 12
<212> TYPE: PRT
<213> ORGANISM: Human immunodeficiency virus

<400> SEQUENCE: 59

Cys Tyr Gly Arg Lys Lys Arg Arg Gln Arg Arg Arg
1               5                   10

<210> SEQ ID NO 60
<211> LENGTH: 21
<212> TYPE: PRT
<213> ORGANISM: Unknown
<220> FEATURE:
<223> OTHER INFORMATION: Description of Unknown:
      PKM2 sequence

<400> SEQUENCE: 60

Val Ala Arg Tyr Arg Pro Arg Ala Pro Ile Ile Ala Val Thr Arg Asn
1               5                   10                  15

Pro Gln Thr Ala Arg
            20

<210> SEQ ID NO 61
<211> LENGTH: 12
<212> TYPE: PRT
<213> ORGANISM: Unknown
<220> FEATURE:
<223> OTHER INFORMATION: Description of Unknown:
      PKM2 sequence

<400> SEQUENCE: 61

Tyr Arg Pro Arg Ala Pro Ile Ile Ala Val Thr Arg
1               5                   10

<210> SEQ ID NO 62
<211> LENGTH: 14
<212> TYPE: PRT
<213> ORGANISM: Unknown
<220> FEATURE:
<223> OTHER INFORMATION: Description of Unknown:
      PKM2 sequence

<400> SEQUENCE: 62

Ala Pro Ile Ile Ala Val Thr Arg Asn Pro Gln Thr Ala Arg
1               5                   10

<210> SEQ ID NO 63
<211> LENGTH: 31
<212> TYPE: DNA
<213> ORGANISM: Homo sapiens

<400> SEQUENCE: 63
agccaccgcc gtgggtgccg tggaggcctc c                                          31

<210> SEQ ID NO 64
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
agccaccgcc gtgggtgccg tgggaggcct cc                                         32

<210> SEQ ID NO 65
<211> LENGTH: 32
<212> TYPE: DNA
<213> ORGANISM: Homo sapiens

<400> SEQUENCE: 65
agccaccgcc gtgggtgccg tggaggcctc ct                                         32

<210> SEQ ID NO 66
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
agccaccgcc gtgggtgccc gtggaggcct cct                                        33

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
agccaccgct gcccgtggag gcctcct                                               27

<210> SEQ ID NO 68
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
agccaccgcc gtgggtg                                                          17

```
<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
agccaccgcc gtgggtggg                                              19

<210> SEQ ID NO 70
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
agccaccgcc gtgtgccgtg gaggcctcc                                   29

<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
agccaccgcc gtgggtgaac cgtggaggcc tcc                              33
```